US012740953B2

(12) United States Patent
Wan et al.

(10) Patent No.: US 12,740,953 B2
(45) Date of Patent: Sep. 22, 2026

(54) COMPOSITIONS COMPRISING HDAC INHIBITORS AND RETINOIDS

(71) Applicant: The Regents of The University of California, Oakland, CA (US)

(72) Inventors: Yu-Jui Yvonne Wan, Davis, CA (US); Kit S. Lam, Davis, CA (US); Ruiwu Liu, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 1180 days.

(21) Appl. No.: 17/522,405

(22) Filed: Nov. 9, 2021

(65) Prior Publication Data

US 2022/0241227 A1 Aug. 4, 2022

Related U.S. Application Data

(63) Continuation of application No. PCT/US2020/033247, filed on May 15, 2020.

(60) Provisional application No. 62/848,906, filed on May 16, 2019.

(51) Int. Cl.

| | |
|---|---|
| ***A61K 31/19*** | (2006.01) |
| ***A61K 31/167*** | (2006.01) |
| ***A61K 31/192*** | (2006.01) |
| ***A61K 31/203*** | (2006.01) |
| ***A61K 31/351*** | (2006.01) |
| ***A61K 31/4436*** | (2006.01) |
| ***A61K 47/58*** | (2017.01) |
| ***A61K 47/69*** | (2017.01) |
| ***A61P 3/00*** | (2006.01) |
| ***A61P 35/00*** | (2006.01) |
| ***A61P 43/00*** | (2006.01) |

(52) U.S. Cl.

CPC ............ *A61K 31/19* (2013.01); *A61K 31/167* (2013.01); *A61K 31/192* (2013.01); *A61K 31/203* (2013.01); *A61K 31/351* (2013.01); *A61K 31/4436* (2013.01); *A61K 47/58* (2017.08); *A61K 47/6907* (2017.08); *A61P 3/00* (2018.01); *A61P 35/00* (2018.01); *A61P 43/00* (2018.01)

(58) Field of Classification Search

None

See application file for complete search history.

(56) References Cited

U.S. PATENT DOCUMENTS

| | | | | |
|---|---|---|---|---|
| 9,872,918 B2 * | 1/2018 | Yurkovetskiy | ..... | A61K 47/6851 |
| 2009/0227674 A1 * | 9/2009 | Richon | .................. | A61P 35/02 514/545 |
| 2016/0041166 A1 | 2/2016 | Jablonski et al. | | |

FOREIGN PATENT DOCUMENTS

| | | |
|---|---|---|
| WO | 2014/093640 A1 | 6/2014 |
| WO | 2017/031084 A1 | 2/2017 |
| WO | 2018/089861 A1 | 5/2018 |
| WO | 2019/217907 A1 | 11/2019 |
| WO | 2020/232399 A1 | 11/2020 |

OTHER PUBLICATIONS

Li et al. ((2015), Critical determinant of intestinal permeability and oral bioavailability of pegylated all trans-retinoic acid prodrug-based nanomicelles: Chain length of poly (ethylene glycol) corona, Colloids and Surfaces B: Biointerfaces, 130, 133-140) (Year: 2015).*

* cited by examiner

*Primary Examiner* — Juliet C Switzer
*Assistant Examiner* — Dawanna Shar-Day White
(74) *Attorney, Agent, or Firm* — Kilpatrick Townsend & Stockton LLP

(57) ABSTRACT

The present invention provides compositions and methods comprising conjugates with a polymeric backbone, e.g., polyvinyl alcohol (PVA), covalently linked histone deacetylase (HDAC) inhibitors, such as butyrate or propionate, and covalently linked retinoids, such as all-trans retinoic acid (RA). The methods and compositions of the invention are useful for the treatment or prevention of cancer or metabolic diseases in tissues such as the colon or liver.

25 Claims, 21 Drawing Sheets

Specification includes a Sequence Listing.

PVA backbone

FXR
ALDH1A1
CYP26A1
bcoA
Relative expression levels
***
p<0.0001
p<0.0001
*
p=0.0156
p<0.05
N
T
GPR41
GPR43
GPR109A
buk
Relative abundance
**
p=0.0036
p<0.002
p<0.05

PVA Control

PRORA100

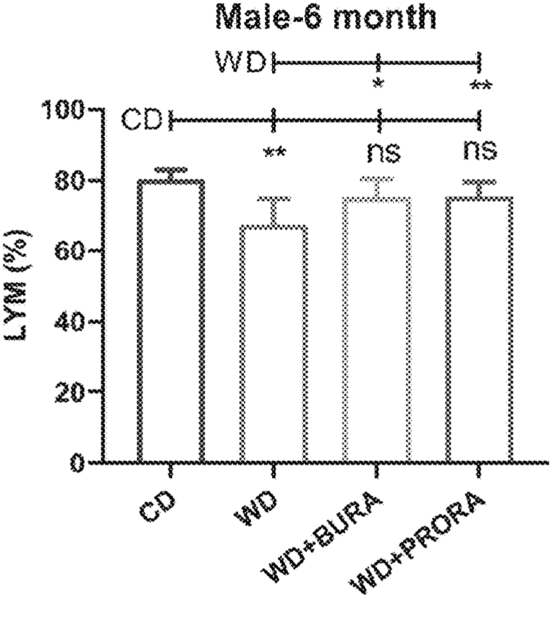
FIG. 18A
FIG. 18B
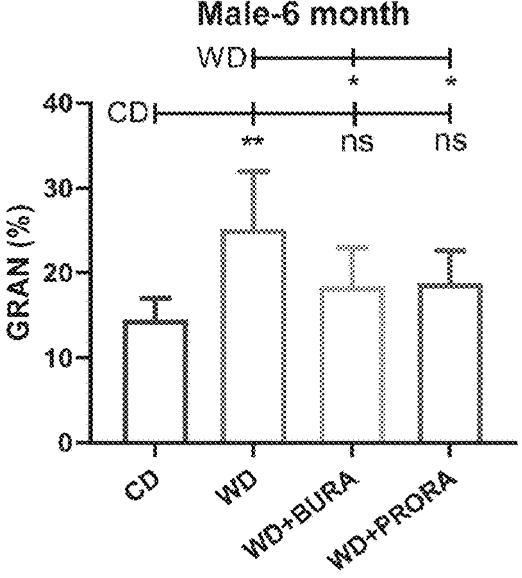
FIG. 18C
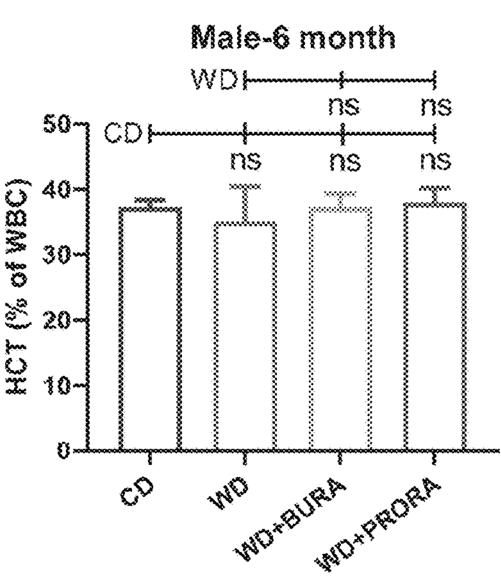
FIG. 18D

COMPOSITIONS COMPRISING HDAC INHIBITORS AND RETINOIDS

CROSS REFERENCE TO RELATED APPLICATIONS

The present application is a continuation of International Application No. PCT/US2020/033247, filed May 15, 2020, which claims priority to U.S. Provisional Pat. Appl. No. 62/848,906, filed on May 16, 2019, which are incorporated herein by reference in their entirety.

REFERENCE TO A SEQUENCE LISTING

The Sequence Listing written in file 070772-228510US-1271673_SL.txt created on May 15, 2020, 612 bytes, machine format IBM-PC, MS-Windows operating system, is hereby incorporated by reference in its entirety for all purposes.

BACKGROUND OF THE INVENTION

Despite advances in therapy over the years, cancer remains a prominent medical problem and is one of the leading causes of death worldwide. In 2012, there were approximately 14 million new cases of cancer, and approximately 8.2 deaths caused by cancer worldwide. It is expected that the number of new cases of cancer will increase from approximately 14 million in 2012 to approximately 30 million by the year 2030.

Furthermore, metabolic diseases such as diabetes, obesity, non-alcoholic steatohepatitis (NASH) and non-alcoholic fatty liver disease (NAFLD) pose prominent threats to health worldwide and are expected to continue to become more prominent. In 2015, nearly 10% of the American population had diabetes. In addition, more than one-third of American adults have obesity.

Accordingly, there is a need for new treatments for cancer and metabolic diseases such as diabetes, obesity, and fatty liver syndromes. The present invention satisfies this need and provides related advantages as well.

BRIEF SUMMARY OF THE INVENTION

The present invention provides compositions and methods comprising conjugates with a polymeric backbone and covalently linked histone deacetylase (HDAC) inhibitors, such as butyrate or propionate, and retinoids, such as all-trans retinoic acid (RA), and which are useful for the treatment or prevention of cancer or metabolic diseases, particularly in tissues such as the colon or liver.

In one aspect, the present disclosure provides a conjugate comprising: (a) a histone deacetylase (HDAC) inhibitor; (b) a retinoid; and (c) a polymer containing a plurality of hydroxyl groups, wherein the HDAC inhibitor and the retinoid are covalently attached to the polymer via the plurality of hydroxyl groups.

In some embodiments, the HDAC inhibitor is a short-chain fatty acid (SCFA). In some embodiments, the SCFA is selected from the group consisting of butyrate, propionate, isobutyrate, valerate, isovalerate, and a combination thereof. In some embodiments, the SCFA is butyrate. In some embodiments, the SCFA is propionate. In some embodiments, the retinoid is selected from the group consisting of retinoic acid (RA), retinol, retinal, isotretinoin, alltretinoin, etretinate, acitretin, tazarotene, bexarotene, adapalene, seletinoid G, a retinyl ester, fenretinide, derivatives thereof, and a combination thereof. In one embodiment, the retinoid is RA. In some embodiments, the polymer is polyvinyl alcohol (PVA). In some embodiments, the polymer is a copolymer of serine and one or more other kinds of amino acids. In one embodiment, the copolymer is a serine-glycine copolymer or a serine-phenylalanine copolymer.

In some embodiments, the HDAC inhibitor and the retinoid are covalently attached to the polymer at a molar ratio of from about 50:1 to about 1000:1 HDAC inhibitor:retinoid. In some embodiments, the molar ratio is about 50:1 or about 100:1 HDAC inhibitor:retinoid. In some embodiments, the HDAC inhibitor is butyrate, the retinoid is RA, the polymer is PVA, and the butyrate and the RA are covalently attached to the PVA at a molar ratio of about 50:1 or about 100:1 butyrate:RA. In some embodiments, the HDAC inhibitor is propionate, the retinoid is RA, the polymer is PVA, and the propionate and the RA are covalently attached to the PVA at a molar ratio of about 50:1 or about 100:1 propionate:RA.

In some embodiments, the conjugate forms nanomicelles. In some embodiments, the nanomicelles are about 20 nm in diameter.

In another aspect, the present disclosure provides a method for treating or preventing cancer or a metabolic disease in a subject, the method comprising administering to the subject a therapeutically effective amount of any of the herein-disclosed conjugates.

In some embodiments, the cancer is colon cancer or liver cancer. In some embodiments, the administration of the conjugate to the subject improves one or more symptoms of cancer in the subject. In some embodiments, the administration of the conjugate increases the recruitment of B or T cells to tumors in the subject. In some embodiments, the T cells comprise $CD3^+$ lymphocytes, $CD4^+$ helper cells, $CD8^+$ T cells, or combinations thereof. In some embodiments, the administration of the conjugate leads to a decrease in the number of tumors in the subject.

In some embodiments, the metabolic disease is selected from the group consisting of alcoholic steatohepatitis (ASH), non-alcoholic steatohepatitis (NASH), non-alcoholic fatty liver disease (NAFLD), diabetes, obesity, dyslipidemia, and a combination thereof. In some embodiments, the administration of the conjugate to the subject leads to an increase in insulin sensitivity and/or a decrease in fasting blood glucose level in the subject.

In some embodiments, the conjugate is administered orally. In some embodiments, the administration of the conjugate to the subject leads to a change in expression or activity of a gene, protein, or molecule targeted by a retinoid and/or an HDAC inhibitor selected from the group consisting of Rarβ, Cyp26b1, Gpr109a, miR-22, HOX A5, AMPK, and combinations thereof. In some embodiments, the administration of the conjugate to the subject leads to an increase in expression and/or activity of PDL-1. In some embodiments, the administration of the conjugate to the subject leads to a downregulation of a gene or protein selected from the group consisting of CYCLIN A2, HDAC1, HDAC4, SIRT1, HDAC6, HDAC8, HDAC11, a protein deacetylase, and combinations thereof. In some embodiments, the administration of the conjugate to the subject leads to the export of nuclear NUR77 to the cytosol.

In another aspect, the present disclosure provides a method for reversing one or more effects of a Western diet in a subject, the method comprising administering to the subject a therapeutically effective amount of any of the herein-described conjugates.

In some embodiments, the one or more effects comprise an effect selected from the group consisting of increased body weight, increased liver/body weight ratio, increased fat weight, increased fat/body weight, increased splenomegaly, decreased lymphocyte percentage in the blood, increased monocyte percentage in the blood, increased granulocyte percentage in the blood, increased mean corpuscular hemoglobin, and increased mean platelet volume.

In another aspect, the present disclosure provides a pharmaceutical composition comprising any of the herein-disclosed conjugates and a pharmaceutically acceptable carrier.

In another aspect, the present disclosure provides a kit for treating or preventing cancer or a metabolic disease in a subject, the kit comprising any of the herein-disclosed pharmaceutical compositions.

Numerous embodiments of the present invention, including compositions and methods for their preparation and administration, are presented herein.

BRIEF DESCRIPTION OF THE DRAWINGS

FIG. 14A shows a timeline of the method used for colon cancer treatment using BURA100 or PRORA100. FIGS. 14B-14D show PRORA100 in treating colon tumors using azoxymethane (AOM) and dextran sodium sulfate (DSS) mouse models.

FIG. 14B shows exemplary images of control and PRORA100-treated tumors, FIG. 14C shows tumor burden, and FIG. 14D shows colon length.

or a Western diet (WD) after weaning at 3 weeks of age. When Western diet-fed mice were 5-months old, they were randomly assigned into control or treatment group. The treated group received BURA100 or PRORA100 (134 mg/g, daily gavage, 4 weeks). All the mice were euthanized when they were 6 months old. FIG. 15A shows body weight, FIG. 15B shows body weight change, FIG. 15C shows liver/body weight, FIG. 15D shows food intake, FIG. 15E shows fat weight, and FIG. 15F shows fat/body weight.

FIGS. 18A-18D. The effect of Western diet intake as well as BURA100 and PRORA100 treatment on blood count. Mice were given a Control diet (CD) or Western diet (WD) and then treated with BURA100 or PRORA100 as described in FIGS. 15A-15F. Percentages of different blood cell types were determined, including the percentage of blood that is lymphocytes (FIG. 18A; normal range: 61.26-87.18%), monocytes (FIG. 18B, normal range: 2.18-11.02%), granulocytes (FIG. 18C, normal ranges: EOS: 0.13-4.42%; BASO: 0.01-1.24%, NEUT: 7.36-28.59%), and red blood cells (hematocrit test) (FIG. 18D, normal range: 37.3-62.0%).

DETAILED DESCRIPTION OF THE INVENTION

1. Introduction

Figure 1:
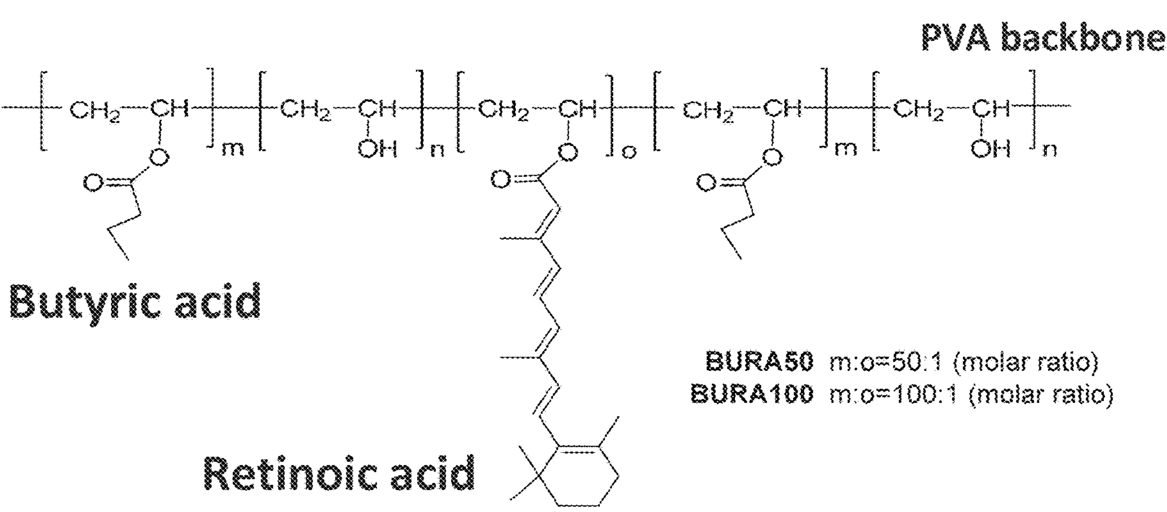
FIG. 1. The structures of BURA and PRORA. BURA and PRORA are novel nano-formulations of short-chain fatty acids and retinoic acid that are covalently linked to a polyvinyl alcohol (PVA) backbone. BURA50 and BURA100 were produced with a molar ratio of butyric acid:retionic acid at 50:1 and 100:1, respectively. PRORA100 was produced with a molar ratio of butyric acid:propionic acid at a molar ratio of 100:1. The ratio can be altered by choice.
Figure 1:
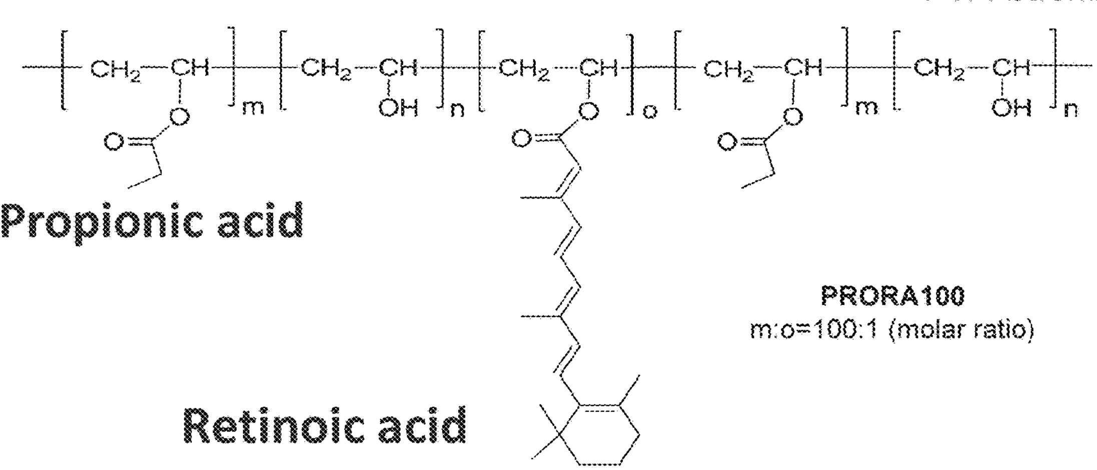

The present invention provides compositions and methods comprising conjugates with a polymeric backbone and covalently linked histone deacetylase (HDAC) inhibitors, such as butyrate or propionate, and retinoids, such as all trans retinoic acid (RA), and which are useful for the treatment or prevention of cancer or metabolic diseases, particularly in tissues such as the colon or liver. The conjugates of the invention assemble into nanomicelles and release the HDAC inhibitors and retinoids gradually and simultaneously, thereby ensuring maximum efficacy in patients. The conjugates of the invention are small in size (~20 nm) and release the HDAC inhibitors and retinoids through slow hydrolysis, resulting in long-acting efficacy, which is different from and an improvement over the free drugs, i.e., RA and butyrate. In addition, the conjugates of the invention are orally deliverable, which is preferred by patients and in low-resource settings since oral administration saves dispensing and administrative cost. The present formulations are effective in both the colon and the liver, showing the significance of the studied pathway in both organs via the gut-liver axis. Thus, the herein-described treatment strategy can be used for both colon and liver cancer, as well as metabolic disease associated with both organs.

2. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" as used herein shall generally mean an acceptable degree of error for the quantity measured given the nature or precision of the measurements. Typically, exemplary degrees of error are within 20 percent (%), preferably within 10%, and more preferably within 5% of a given value or range of values. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

The term "cancer" refers to any of various malignant neoplasms characterized by the proliferation of anaplastic cells that tend to invade surrounding tissue and metastasize to new body sites. Non-limiting examples of different types of cancer suitable for treatment using the method and compositions of the present invention include colorectal cancer, colon cancer, anal cancer, liver cancer, ovarian cancer, breast cancer, lung cancer, bladder cancer, thyroid cancer, pleural cancer, pancreatic cancer, cervical cancer, prostate cancer, testicular cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, skin cancer, oral squamous cell carcinoma, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma. In particular methods of the invention, the cancer is liver cancer or colon cancer.

The term "metabolic disease" refers to any disease or disorder that disrupts normal metabolism, including any disease that disrupts or dysregulates biochemical reactions that function to convert food into energy, process or transport amino acids, proteins, carbohydrates (e.g., sugars, starches), or lipids (e.g., fatty acids), etc. In some embodiments, a metabolic disease results in the abnormal processing or regulation of sugars, lipids, cholesterol, and/or the metabolism of drugs (e.g., by the liver). Non-limiting examples of metabolic diseases include obesity, insulin resistance, type 2 diabetes, hyperlipidemia, non-alcoholic fatty liver disease (NAFLD), alcoholic steatohepatitis (ASH), and non-alcoholic steatohepatitis (NASH), as well as the sequelae of such diseases. Metabolic diseases also comprise the inflammatory states or conditions that frequently accompany such diseases. As such, in some embodiments, methods provided to treat or prevent metabolic diseases can ameliorate or reduce an inflammatory state or condition associated with the metabolic disease.

The term "retinoid" refers to a class of compounds that are vitamers of vitamin A (i.e., compounds that generally have a similar structure to vitamin A) or are chemically related to vitamin A. Retinoids include, any natural or synthetic derivative of retinol. Non-limiting examples of retinoids as used in the present invention include trans retinoic acid (RA), retinol, retinal, isotretinoin, alltretinoin, etretinate, acitretin, tazarotene, bexarotene, adapalene, seletinoid G, a retinyl ester, and fenretinide.

The term "histone deacetylase" or "HDAC" refers to a class of enzymes (Enzyme Commission number 3.5.1.98) that remove acetyl groups from proteins, including ε-N-acetyl lysine amino acids on histones. Histone deacetylation allows histones to wrap and compact DNA more tightly within chromatin, which is associated with gene silencing. Class I HDACs include HDAC1, HDAC2, HDAC3, and HDAC8. Class IIA HDACs include HDAC4, HDAC5, HDAC7, and HDAC9. Class IIB HDACs include HDAC6 and HDAC10. Class III HDACs include SIRT1, SIRT2, SIRT3, SIRT4, SIRT5, SIRT6, and SIRT7 in mammals and Sir2 in yeast. Class IV HDACs include HDAC11.

In humans, HDAC1 is encoded by the HDAC1 gene. A non-limiting example of a human HDAC1 amino acid sequence is set forth under GenBank Accession number NM_004964.2→NP_004955.2. In humans, HDAC4 is encoded by the HDAC4 gene. A non-limiting example of a human HDAC4 amino acid sequence is set forth under GenBank Accession number NM_006037.3→NP_006028.2. In humans SIRT1 is encoded by the SIRT1 gene. Non-limiting examples of human SIRT1 amino acid sequences are set forth under GenBank Accession number NM 001142498.1→NP 001135970.1, NM_00131-4049.1→NP_001300978.1, and NM_012238.4→NP_036370.2.

The term "histone deacetylase inhibitor" of "HDAC inhibitor" refers to any natural or synthetic compound or agent that decreases or suppresses the activity and/or expression of an HDAC. In some embodiments, an HDAC inhibitor (e.g., an HDAC inhibitor present within a conjugate of the invention) decreases or suppresses the mRNA expression of an HDAC (e.g., transcription from a gene encoding an HDAC is decreased or suppressed). In some embodiments, an HDAC inhibitor (e.g., an HDAC inhibitor present within a conjugate of the invention) decreases or suppresses the protein expression of an HDAC (e.g., translation of an mRNA expressed from an HDAC gene is decreased or suppressed). In some embodiments, an HDAC inhibitor (e.g., an HDAC inhibitor present within a conjugate of the invention) decreases or suppresses the enzymatic activity of an HDAC. In some embodiments, an HDAC inhibitor (e.g., an HDAC inhibitor present within a conjugate of the invention) decreases or suppresses the ability of an HDAC to deacetylate a protein, e.g., a histone.

Non-limiting examples of HDAC inhibitors include short-chain fatty acids (e.g., propionate, butyrate, isobutyrate, valerate, isovalerate), suberanilohydroxamic acid (SAHA), entinostat, panobinostat, trichostatin A, Scriptaid, mocetinostat, chidamide, TMP195, citarinostat, belinostat, depsipeptide, MC1568, tubastatin, givinostat, dacinostat, CUDC-101, JNJ-26481585, pracinostat, PCI-34051, PCI-34051, droxinostat, abexinostat, RGFP966, AR-42, ricolinostat, valproic acid, tacedinaline, CUDC-907, curcumin, M344, tubacin, RG2833, resminostat, divalproex, sodium phenylbutyrate, TMP269, CAY10683, tasquinimod, BRD73954, splitomicin, HPOB, LMK-235, nexturastat A, (−)-parthenolide, CAY10603, 4SC-202, BG45, and ITSA-1.

The term "microRNA" or "miR" refers to a small non-coding RNA molecule (e.g., containing about 22 nucleotides) found in plants, animals, and some viruses, that functions in RNA silencing and post-transcriptional regulation of gene expression. A non-limiting example is miR-22 (SEQ ID NO:1).

The "miR-22" family, belonging to gene family number MIPF0000053, contains about 50 sequences across various species (see, e.g., www.mirbase.org/cgi-bin/mirna_summary.pl?fam=MIPF0000053). The coding sequence for human miR-22 (hsa-miR-22) is located on chromosome 17. Non-limiting examples of human miR-22 sequences include hsa-miR-22-3p (miRBASE accession number MIMAT0000077; SEQ ID NO:1), hsa-miR-22-5p (miRBASE accession number MIMAT0004495), and the hsa-miR-22 stem loop sequence (miRBASE accession number MI0000078).

The term "miR-22 inhibitor" refers to any agent that inhibits or decreases the expression, stability, or activity of miR-22. In some embodiments, a miR-22 inhibitor decreases or abolishes the expression (e.g., transcription) of miR-22. In some embodiments, a miR-22 inhibitor decreases the stability of a miR-22 RNA molecule or promotes the degradation of a miR-22 RNA molecule. In some embodiments, a miR-22 inhibitor decreases or prevents the binding of a miR-22 RNA molecule (e.g., to a binding target). In some embodiments, a miR-22 inhibitor is an oligonucleotide (e.g., an antisense oligonucleotide), which can, as a non-limiting example, comprise the nucleic acid sequence set forth in SEQ ID NO:2. In some embodiments, a miR-22 inhibitor is a small molecule compound that binds to miR-22 and decreases or abolishes its activity.

"BURA" and "PRORA" refer to conjugates comprising a polyvinyl alcohol (PVA) polymer backbone, all trans retinoic acid (RA) conjugated to a portion of the hydroxyl groups on the polymer backbone, and either butyrate (in "BURA") or propionate (in "PRORA") conjugated to other hydroxyl groups on the polymer backbone. BURA and PRORA conjugates can comprise any relative proportions of butyrate or propionate, respectively, with respect to the RA within the conjugate and/or the individual PVA monomers and/or the hydroxyl groups on the polymer. When BURA or PRORA is followed by a number, e.g., BURA50, BURA100, PRORA50, PRORA100, etc., the number refers to the molar ratio of butyrate or propionate within the conjugate to RA. For example, BURA50 is a conjugate in which the molar ratio of butyrate to RA is 50:1.

The term "metabolism-enhancing agent" refers to a compound or composition that promotes or maintains normal metabolism, or ameliorates the causes or sequelae of a metabolic disease. In some embodiments, a metabolism-enhancing agent prevents or treats, either alone or in combination with one or more additional agents, a metabolic disease. In some embodiments, a metabolism-enhancing agent is a compound or composition that increases or promotes FGF21 and/or FGFR1 expression or activity (e.g., FGF21 signaling). In some embodiments, a metabolism-enhancing agent is a compound or composition that functions as a histone deacetylase inhibitor. In some embodiments, a metabolism-enhancing agent is a compound or composition (e.g., metformin) that increases or promotes 5' adenosine monophosphate-activated protein kinase (AMPK) expression or activity (e.g., AMPK signaling). In some embodiments, a metabolism-enhancing agent is a compound or composition that increases or promotes sirtuin 1 (SIRT1) expression or activity (e.g., SIRT1 signaling). In some embodiments, a metabolism-enhancing agent is a compound or composition that increases or promotes Beta-klotho expression or activity (e.g., Beta-klotho signaling). In some embodiments, a metabolism-enhancing agent is a compound or composition that increases or promotes bile acid receptor (FXR) expression or activity (e.g., FXR signaling).

A "Western diet" as used herein refers to a diet comprising high levels of fat, e.g., saturated fat and sugar, e.g., sucrose. Western diet can also comprise high levels of cholesterol, and/or low levels of fiber. For example, a Western diet may contain high amounts of red meat, processed meat, pre-packaged foods, butter, fried food, high-fat dairy products, eggs, refined grains, corn, candy and other sweets, including sweetened beverages, potatoes, alcohol, salt, high fructose and/or corn syrup. A Western diet often comprises inadequate amounts of foods such as fruit, vegetables, whole grains, legumes, fish, and/or low-fat dairy products. In some embodiments, a Western diet comprises at least 20% fat, at least 30% sucrose, and at least 0.2% cholesterol.

The term "delivery-enhancing agent" refers to any compound or composition that promotes delivery, stability, availability, or effectiveness of an active agent (e.g., a conjugate of the invention). In some embodiments, a delivery-enhancing agent increases the ability of an active agent to reach a target cell or tissue. In some embodiments, a delivery-enhancing agent increases the stability of an active agent or protects an active agent from degradation or metabolism. As a non-limiting example, a delivery-enhancing agent may protect an active agent from digestion in the gut until the active agent reaches the desired target cell or tissue. In some embodiments, a delivery-enhancing agent reduces the amount of an active agent that is needed in order to achieve the desired effect (e.g., therapeutic effect). In some embodiments, a delivery-enhancing agent increases the solubility of an active agent. In some embodiments, a delivery-enhancing agent increases the bioavailability of an active agent or increases the retention time of an active agent (e.g., within a subject following administration).

The terms "subject," "individual," and "patient" are used interchangeably herein to refer to a vertebrate, preferably a mammal, more preferably a human. Mammals include, but are not limited to, murines, rats, simians, humans, farm animals, sport animals, and pets. Tissues, cells and their progeny of a biological entity obtained in vivo or cultured in vitro are also encompassed.

As used herein, the term "administering" includes oral administration, topical contact, administration as a suppository, intravenous, intraperitoneal, intramuscular, intralesional, intrathecal, intranasal, intraosseous, or subcutaneous administration to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, intraosseous, and intracranial. Other modes of delivery include, but are not limited to, the use of liposomal formulations, intravenous infusion, transdermal patches, etc.

The term "treating" refers to an approach for obtaining beneficial or desired results including, but not limited to, a therapeutic benefit and/or a prophylactic benefit. By therapeutic benefit is meant any therapeutically relevant improvement in or effect on one or more diseases, conditions, or symptoms under treatment. Therapeutic benefit can also mean to effect a cure of one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "therapeutically effective amount" or "sufficient amount" refers to the amount of an agent, e.g., a conjugate of the invention, that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other compounds, timing of administration, and the physical delivery system in which it is carried.

For the purposes herein an effective amount is determined by such considerations as may be known in the art. The amount must be effective to achieve the desired therapeutic effect in a subject suffering from cancer or a metabolic disease. The desired therapeutic effect may include, for example, improvement in or amelioration of undesired symptoms associated with cancer or the metabolic disease, prevention of the manifestation of such symptoms before they occur, slowing down the progression of symptoms associated with cancer or the metabolic disease, slowing down or limiting any irreversible damage caused by the cancer or the metabolic disease, lessening the severity of or curing cancer or the metabolic disease, or improving the survival rate or providing more rapid recovery from cancer or the metabolic disease. Further, in the context of prophylactic treatment the amount may also be effective to prevent the development of the cancer or the metabolic disease, including in patients who have previously had cancer or metabolic disease, i.e., the agent prevents the recurrence of the disease in question.

The term "pharmaceutically acceptable carrier" refers to a substance that aids the administration of an active agent to a cell, an organism, or a subject. "Pharmaceutically acceptable carrier" refers to a carrier or excipient that can be included in the compositions of the invention and that causes no significant adverse toxicological effect on the patient. Non-limiting examples of pharmaceutically acceptable carrier include water, NaCl, normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The carrier may also be substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor, etc. In some instances, the carrier is an agent that facilitates the delivery of a conjugate of the invention to a target cell or tissue. One of skill in the art will recognize that other pharmaceutical carriers are useful in the present invention.

The term "nucleic acid" as used herein refers to a polymer containing at least two deoxyribonucleotides or ribonucleotides in either single- or double-stranded form and includes DNA, RNA, and hybrids thereof. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. RNA may be in the form of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogs of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res., 19:5081 (1991); Ohtsuka et al., J. Biol. Chem., 260:2605-2608 (1985); Rossolini et al., Mol. Cell. Probes, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

3. Structure and Synthesis of the Conjugates

In one aspect, the present invention provides compositions and methods for preventing or treating cancer or metabolic diseases in a subject (e.g., a subject in need thereof, e.g., a subject with colon or liver cancer, or a metabolic disease). The present compounds comprise a conjugate comprising a histone deacetylase (HDAC) inhibitor, a retinoid, and a polymer containing a plurality of hydroxyl groups, in which the HDAC inhibitor and retinoid are covalently linked to the hydroxyl groups of the polymer. In some embodiments, the methods comprise administering to the subject a therapeutically effective amount of a conjugate of the invention.

As non-limiting examples, the HDAC inhibitors that can be included in the conjugates of the invention include short-chain fatty acids (SCFA). In some embodiments, the SCFA is propionate, butyrate, isobutyrate, isovalerate, or a combination thereof. In particular embodiments, the HDAC inhibitor is butyrate or propionate.

As non-limiting examples, the retinoids that can be included in the conjugates of the invention include all trans retinoic acid (RA), retinol, retinal, isotretinoin, alltretinoin, etretinate, acitretin, tazarotene, bexarotene, adapalene, seletinoid G, a retinyl ester, fenretinide, derivatives thereof, and combinations thereof. In particular embodiments, the retinoid is RA.

As non-limiting examples, the polymers with hydroxyl groups that can be used to covalently attach the HDAC inhibitors and retinoids of the invention include polyvinyl alcohol (PVA) and polymers comprising serine and one or more other kinds of amino acids such as glycine and/or phenylalanine. In particular embodiments, the polymer is PVA.

In particular embodiments of the invention, the compounds comprise PVA, RA, and either butyrate (in which case the conjugate is referred to as BURA) or propionate (in which case the conjugate is referred to as PRORA).

BURA has the structure as shown below and in FIG. 1, where m is butyrate conjugated to the PVA backbone, n is PVA with an unreacted hydroxyl group, and o is retinoic acid conjugated to the PVA backbone. It will be understood that the arrangement of the butyrate and RA moieties on the PVA polymer is not necessarily as shown in the schematic below: whereas the schematic shows the butyrate and RA moieties occurring regularly and in an alternating fashion on the polymer backbone, in the present invention the butyrate and RA moieties may in fact be in any order or arrangement, e.g., with multiple butyrate moieties or RA moieties occurring in succession, with irregular spacing between the butyrate and/or RA moieties, etc., so long as the overall molar ratio of the conjugate in question is maintained (e.g., 50:1 molar ratio of butyrate to RA in BURA50, 100:1 molar ratio of butyrate to RA in BURA100, etc.).

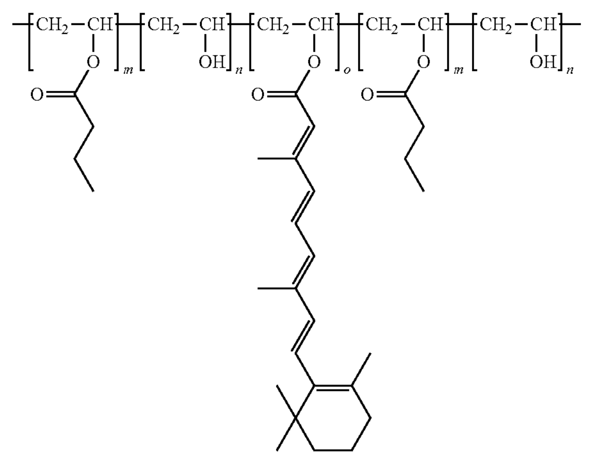

BURA50 m:o = 50:1 (molar ratio)
BURA100 m:o = 100:1 (molar ratio)

PRORA has the structure shown below and in FIG. 1. It will be understood that the arrangement of the propionate and RA moieties on the PVA polymer is not necessarily as shown below: whereas the schematic shows the propionate and RA moieties occurring regularly and in an alternating fashion on the polymer backbone, in the present invention the propionate and RA moieties may in fact be in any order or arrangement, e.g., with multiple propionate moieties or RA moieties occurring in succession, with irregular spacing between the propionate and/or RA moieties, etc., so long as the overall molar ratio of the conjugate in question is maintained (e.g., 50:1 molar ratio of proprionate to RA in PRORA50, 100:1 molar ratio of propionate to RA in PRORA100, etc.).

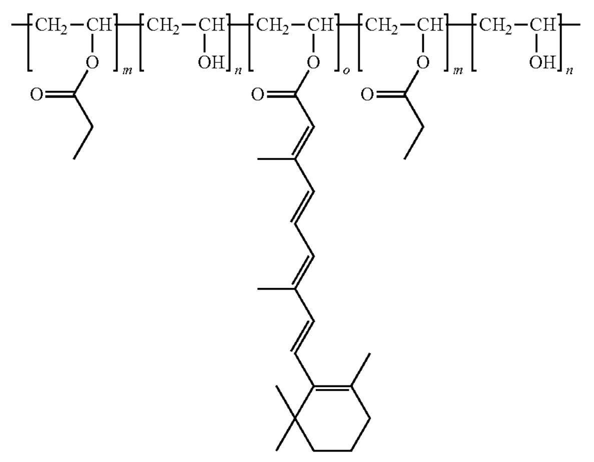

PRORA100
m:o = 100:1 (molar ratio)

The molar ratio of the HDAC inhibitor in the conjugate, e.g., butyrate or propionate, to the retinoid in the conjugate, e.g., RA, can be any of a wide range of ratios, e.g., 1:1, 2:1, 3:1, 4:1, 5:1, 10:1, 20:1, 30:1, 40:1, 50:1, 60:1, 70:1, 80:1, 90:1, 100:1, 150:1, 200:1, 250:1, 300:1, 400:1, 500:1, 600;1, 700:1, 800:1, 900:1, 1000:1, 1300:1, 1500:1, 2000:1, 2500:1, 3000:1, 3500:1, 4000:1, 4500:1, 5000:1, or higher. In particular embodiments, the molar ratio of the HDAC inhibitor to the retinoid, e.g., butyrate or propionate to RA, is 50:1, 100:1, 500:1, or 1000:1. In one embodiment, the ratio of butyrate or propionate to RA is 58.83 to 1.17 moles. In another embodiment, the ratio of butyrate or propionate to RA is 59.4 to 0.6 moles.

In some embodiments, the molar ratio of the HDAC inhibitor in the conjugate, e.g., butyrate or propionate, to the retinoid in the conjugate, e.g., RA, is 1:5000, 1:4500, 1:4000, 1:3500, 1:3000, 1:2500, 1:2000, 1:1500, 1:1000, 1:900, 1:800, 1:700, 1:600, 1:500, 1:400, 1:300, 1:250, 1:200, 1:150, 1:100, 1:90, 1:80, 1:70, 1:60, 1:50, 1:40, 1:30, 1:20, 1:10, 1:5, 1:4, 1:3, or 1:2.

The conjugates can be prepared with any relative proportion of the monomer subunits of the polymer, e.g., PVA, conjugated with an HDAC inhibitor such as butyrate or proprionate or with a retinoid such as RA. For example, conjugates can be used in which 5%, 10%, 15%, 20%, 25%, 30%, 35%, 40%, 45%, 50%, 55%, 60%, 65%, 70%, 75%, 80%, 85%, 90%, 95%, or 100% of the monomers within the polymer have conjugated HDAC inhibitor or retinoid moieties. In some embodiments, 60% of the monomers are conjugated, such that the ratio of m+o units (hydroxyl groups with butyrate or propionate) in the drawings above to the n units (unreacted hydroxyl groups) is about 3:2. In other embodiments, a molar ratio of about 10%, 20%, 30%, 40%, 50%, 60%, 70%, 80%, or 90% of butyrate or propionate to the total hydroxyl groups of PVA is used.

BURA, PRORA, and the other conjugates of the invention can assemble into nanomicelles, and release the covalently linked HDAC inhibitor, e.g., butyrate or propionate, and retinoid, e.g., RA, both simultaneously and gradually in vivo through slow hydrolysis. This simultaneous, gradual release of the compounds in vivo ensures optimal efficacy based upon their interactive combined effects. The nanomicelles can be any of a range of sizes, e.g., 5, 10, 15, 20, 25, 30, 35, 40, 45, or 50 nm in diameter. In particular embodiments the nanomicelles are 15-30 nm in diameter. In some embodiments, the nanomicelles are about 20 nm in diameter.

Synthesis of the conjugates of the invention can be performed using standard organic chemistry methods, e.g., DMAP-catalyzed conjugation of butyryl chloride, propionyl chloride, or RA to the hydroxyl groups of the hydroxyl group-containing backbone, e.g., PVA. For example, in one embodiment, PVA is dissolved in anhydrous dimethyl sulfoxide (DMSO), followed by the addition of 4-dimethylaminopyridine (DMAP) to the DMSO solution. Once the DMAP has dissolved, butyryl or propionyl chloride is added dropwise while stirring. The resulting solution is then stirred for, e.g., 2-5 hours. All trans-retinoic acid (RA) is dissolved in a mixture of N,N-dimethylformamide (DMF) and dichloromethane, and then N,N'-dicyclohexylcarbodiimide (DCC) is added. This mixture is then added to the PVA-butyrate or PVA-propionate DMSO solution, and additional DMAP is then added. Under argon gas atmosphere and in the dark, the resulting solution is stirred for, e.g., 2 days, and the BURA or PRORA is then precipitated and washed with acetonitrile. The precipitate is suspended in water and filtered, e.g., through a 0.2 μm filter. The water solution is then dialyzed against a large quantity of water (molecular cut off size of, e.g., 6000-8000) for, e.g., 2-3 days, and the solution is lyophilized to generate the final product.

Any of a number of methods known in the art can be used to characterize the conjugates, e.g., BURA or PRORA, prior to use. For example, they can be characterized by matrix-assisted laser desorption/ionization time of flight mass spectrometry (MALDI-TOF MS) and/or gel permeation chromatography, and their particle size, zeta potential, and the stability of micelles can be analyzed using a dynamic light scattering (DLS) particle sizer (e.g., Mastersizer 3000). Further, the critical micelle concentration can be determined, e.g., by fluorescent techniques using, e.g., pyrene or nile red as the optical probe. Further, the conjugated HDAC inhibitor and retinoid can be quantified, e.g., by hydrolysis, acidification, and extraction, followed by quantification, e.g., by gas chromatography with a GC flame ionization detector (GC-FID; e.g., from Agilent; e.g., for butyrate and/or propionate) or by triple-quadruple LC/MS/MS (e.g., for RA).

4. Methods for Preventing or Treating Diseases

In one aspect, the present invention provides methods of treating or preventing diseases comprising administering to a subject (e.g., a subject in need thereof) a therapeutically effective amount of a conjugate of the invention, i.e., a conjugate comprising a histone deacetylase (HDAC) inhibitor, a retinoid, and a polymer containing a plurality of hydroxyl groups, in which the HDAC inhibitor and retinoid are covalently linked to the hydroxyl groups of the polymer.

In some embodiments, the HDAC inhibitor of the conjugate is a short chain fatty acid. In particular embodiments, the short chain fatty acid is butyrate or propionate. In particular embodiments, the retinoid of the conjugate is all trans retinoic acid (RA). In particular embodiments, the polymer is polyvinyl alcohol (PVA).

The methods of the invention can be used to treat or prevent any of a number of diseases or conditions. In some embodiments, the disease or condition is cancer, e.g. liver or colon cancer. In some embodiments, the disease or condition is a metabolic disease, e.g., obesity, type 2 diabetes, metabolic syndrome, or other disease or condition involving the colon or liver, including inflammation associated with a metabolic disease. In some embodiments, the metabolic disease is the result of prolonged consumption of a Western diet.

Methods of the present invention for preventing or treating cancer in a subject (e.g., a subject in need thereof) are suitable for any type of cancer, including but not limited to liver cancer or colon cancer. In some embodiments, the subject has one or more colon polyps.

In some of embodiments, the cancer is an advanced stage cancer (e.g., advanced stage liver or colon cancer). In some embodiments, the cancer is metastatic (e.g., metastatic liver or colon cancer). In some embodiments, treating the subject comprises inhibiting cancer cell growth; inhibiting cancer cell migration; inhibiting cancer cell invasion; ameliorating the symptoms of cancer; reducing the size of a cancer tumor; reducing the number of cancer tumors; reducing the number of cancer cells; inducing cancer cell necrosis, pyroptosis, oncosis, apoptosis, autophagy, or other cell death; or enhancing the therapeutic effects of another anti-cancer agent.

As used herein, the phrase "ameliorating the symptoms of cancer" includes alleviating or improving the symptoms or condition of a patient having cancer (e.g., liver or colon cancer). Ameliorating the symptoms includes reducing the pain or discomfort associated with cancer. Ameliorating the symptoms also includes reducing the markers of cancer, e.g., reducing the number of cancer cells or reducing the size or number of cancer tumors.

In one embodiment, a conjugate of the invention is co-administered with miR-22 or a mimic thereof to a subject. In one such embodiment, the subject has cancer, e.g., colon or liver cancer. In some embodiments, administration of a conjugate of the invention leads to the recruitment of B or T cells, e.g., $CD3^+$ lymphocytes, $CD4^+$ helper T cells, or $CD8^+$ T cells, to tumors or to cancerous tissue in a subject, e.g., liver or colon cancer. In some embodiments, administration of a conjugate of the invention leads to a decrease in the number of tumors in the subject.

Methods of the present invention are useful for preventing or treating any number of metabolic diseases. In some embodiments, a method or composition of the present invention is used to prevent or treat obesity. In some embodiments, a method or composition of the present invention is used to prevent or treat diabetes (e.g., type 2 diabetes). In some embodiments, a method or composition of the present invention is used to reverse one or more effects of a Western diet. In particular embodiments, a method or composition of the present invention is used to increase insulin sensitivity. In some embodiments, a method or composition of the present invention is used to prevent or treat NAFLD or NASH. In some embodiments, a method or composition of the present invention is used to prevent or treat an inflammatory condition or state associated with a metabolic disease.

Fatty liver disease (FLD), also known simply as fatty liver or hepatic steatosis, is a condition wherein large vacuoles of triglyceride fat accumulate in hepatocytes via the process of steatosis (i.e., infiltration of liver cells with fat). FLD can occur in individuals who consume little or no alcohol, in which case the disease is known as non-alcoholic fatty liver disease (NAFLD). The accumulation of fat in the liver leads to inflammation and the development of fibrosis within the liver. As the extent of liver fibrosis increases, the development of more severe non-alcoholic steatohepatitis (NASH) occurs. Accompanying the progression of liver fibrosis due to NAFLD and NASH is a progressive deterioration of liver function, possibly leading to liver failure. FLD is estimated to affect about 10 to 20 percent of Americans, with an additional about 2 to 5 percent being affected by the more severe NASH. NASH is often first suspected in an individual who is found to have elevated levels of one or more biomarkers of liver disease (e.g., ALT and AST), particularly when there is no other apparent reason for liver disease (e.g., heavy alcohol intake, medication, or infection such as hepatitis). A suspicion of NASH may also occur when X-ray or other imaging studies show evidence of fatty liver. The gold standard for distinguishing NASH from more benign FLD is to perform a liver biopsy. Suitable biomarkers for the detection and monitoring of liver disease, including NAFLD and NASH, include but are not limited to aspartate aminotransferase (AST), alanine aminotransferase (ALT), the ratio of AST to ALT (i.e., the AST/ALT ratio is often greater than 2 in progressive NASH), gamma-glutamyl transferase (GGT), the aspartate to platelet ratio index (APRI), alkaline phosphatase (AP), bilirubin, and ferritin.

As used herein, the phrase "ameliorating the symptoms of a metabolic disease" includes alleviating or improving the symptoms or condition of a patient having a metabolic disease (e.g., metabolic syndrome, obesity, type 2 diabetes). Ameliorating the symptoms includes reducing the pain or discomfort associated with the disease or condition. Ameliorating the symptoms also includes reducing the markers of the disease or condition, e.g., increasing insulin sensitivity or decreasing fasting blood glucose levels. Ameliorating the symptoms also includes reducing or alleviating an inflammatory condition or state associated with a metabolic disease.

In some embodiments, administration of a conjugate of the invention leads to the reversal, improvement, or slowing of one or more effects of a Western diet in a subject, such as increased body weight, increased liver/body weight ratio, increased fat weight, increased fat/body weight, increased splenomegaly, decreased lymphocyte percentage in the blood, increased monocyte percentage in the blood, increased granulocyte percentage in the blood, increased mean corpuscular hemoglobin, and increased mean platelet volume.

In one embodiment, a conjugate of the invention is co-administered with a miR-22 inhibitor to a subject. In one such embodiment, the subject has a metabolic disease. In another embodiment, co-administration of the conjugate and miR-22 inhibitor to a subject having a metabolic disease improves insulin sensitivity and/or reduces fasting blood glucose level.

In some embodiments, the administration of the conjugate of the invention in a subject leads to the activation or inhibition of a gene or protein associated with, e.g., cancer or metabolic disease. In one embodiment, the administration of the conjugate of the invention in a subject leads to the upregulation of miR-22 in the liver or colon, e.g., in liver or colon cancer cells. In one embodiment, administration of the conjugate of the invention leads to the activation of AMPK in the liver or colon, e.g., in liver or colon cancer cells. In one embodiment, administration of the conjugate of the invention leads to a change in the expression or activity of a gene or protein targeted by a retinoid or HDAC inhibitor, e.g., Rarβ, Cyp26b1, Gpr109a, or HOX A5 in the liver or colon, e.g., in liver or colon cancer cells. In one embodiments, administration of the conjugate of the invention leads to an increase in the expression of PDL1 (Programmed death-ligand 1, or CD274; see, e.g., NCBI Gene ID 29126) in the liver or colon, e.g., in liver or colon cancer cells. In one embodiment, administration of the conjugate of the invention leads to a downregulation of a gene or protein such as CYCLIN A2, HDAC1, HDAC4, SIRT1, HDAC6, HDAC8, or HDAC11 in the liver or colon, e.g., in liver or colon cancer cells. In one embodiment, administration of the conjugate of the invention leads to the export of nuclear NUR77 to the cytoplasm in the liver or colon, e.g., in liver or colon cancer cells.

In particular embodiments, a test sample is obtained from the subject. The test sample can be obtained before and/or after the conjugate or pharmaceutical composition is administered to the subject. Non-limiting examples of suitable samples include blood, serum, plasma, cerebrospinal fluid, tissue, saliva, urine or any combination thereof. In some instances, the sample comprises normal tissue. In other instances, the sample comprises cancer tissue. The sample can also be made up of normal and/or cancer cells. Tissue samples can be obtained by biopsy or surgical resection.

In some embodiments, a reference sample is obtained. The reference sample can be obtained, for example, from the subject and can comprise normal tissue. The reference sample can be also be obtained from a different subject and/or a population of subjects. In some instances, the reference sample is either obtained from the subject, a different subject, or a population of subjects before and/or after the conjugate or pharmaceutical composition is administered to the subject and comprises normal tissue. However, in some instances the reference sample comprises cancer tissue and is obtained from the subject and/or from a different subject or a population of subjects.

In some embodiments, the level of one or more biomarkers is determined in the test sample and/or reference sample. Non-limiting examples of suitable biomarkers include miR such as miR-22. In some embodiments, at least one of the biomarkers is a miR. Other non-limiting examples of suitable biomarkers include FGF21, FGFR1c, Beta-klotho, blood glucose, aspartate aminotransferase (AST), alanine aminotransferase (ALT), the ratio of AST to ALT, gamma-glutamyl transferase (GGT), the aspartate to platelet ratio index (APRI), alkaline phosphatase (AP), bilirubin, ferritin, alpha-smooth muscle actin (αSMA), procollagen α1 (procol1), transforming growth factor-β (TGFβ), monocyte chemoattractant protein-1 (MCP1), interleukin-1β (IL-1b), tumor necrosis factor alpha (TNFα), connective tissue growth factor (CTGF), and platelet derived growth factor receptor beta (PDGFRβ). Any combination of biomarkers, including those described herein and others that will readily be known to one of skill in the art, can be used.

Typically, the level of the one or more biomarkers in one or more test samples is compared to the level of the one or more biomarkers in one or more reference samples. As a non-limiting example, levels of one or biomarkers in test samples taken before and after the conjugate or pharmaceutical composition is administered to the subject are compared to the level of the one or more biomarkers in a reference sample that is either normal tissue obtained from the subject, or normal tissue that is obtained from a different subject or a population of subjects. In some instances, the biomarker in a test sample obtained from the subject before the subject is treated is lower than the level of the biomarker in the reference sample. In other instances, the level of biomarker in a test sample obtained from the subject after the subject is treated is increased relative to the level of the biomarker in a test sample obtained prior to administration.

The differences between the reference sample or value and the test sample need only be sufficient to be detected. In some embodiments, a decreased level of a biomarker in the test sample, and hence the presence of cancer or increased risk of cancer, or the presence of a metabolic disease or the risk of a metabolic disease, is determined when the biomarker levels are at least, e.g., 10%, 25%, 50% or more lower in comparison to a negative control. In some embodiments, an increased level of a biomarker in the test sample, and hence the presence of cancer or increased risk of cancer, or the presence of a metabolic disease or the risk of a metabolic disease, is determined when the biomarker levels are at least, e.g., 10%, 25%, 50% or more greater in comparison to a negative control.

The biomarker levels can be detected using any method known in the art, including the use of antibodies specific for the biomarkers. Exemplary methods include, without limitation, western blot, dot blot, enzyme-linked immunosorbent assay (ELISA), radioimmunoassay (RIA), immunoprecipitation, immunofluorescence, FACS analysis, electrochemiluminescence, and multiplex bead assays (e.g., using Luminex or fluorescent microbeads).

In some embodiments, the antibody or plurality thereof used to detect the biomarker(s) can be immobilized on a solid support. The solid support can be, for example, a multiwell plate, a microarray, a chip, a bead, a porous strip, or a nitrocellulose filter. In some instances, the bead comprises chitin. The immobilization can be via covalent or non-covalent binding.

Labeled secondary antibodies can be used to detect binding between antibodies and biomarkers. Secondary antibodies bind to the constant or "C" regions of different classes or isotypes of immunoglobulins IgM, IgD, IgG, IgA, and IgE. Usually, a secondary antibody against an IgG constant region is used in the present methods. Secondary antibodies against the IgG subclasses, for example, IgG1, IgG2, IgG3, and IgG4, also find use in the present methods. Secondary antibodies can be labeled with any directly or indirectly detectable moiety, including a fluorophore (e.g., fluorescein, phycoerythrin, quantum dot, Luminex bead, fluorescent bead), an enzyme (e.g., peroxidase, alkaline phosphatase), a radioisotope (e.g., $^{3}H$, $^{32}P$, $^{125}I$) or a chemiluminescent moiety. Labeling signals can be amplified using a complex of biotin and a biotin binding moiety (e.g., avidin, streptavidin, neutravidin). Fluorescently labeled anti-human IgG antibodies are commercially available from Molecular Probes, Eugene, OR. Enzyme-labeled anti-human IgG antibodies are commercially available from Sigma-Aldrich, St. Louis, MO and Chemicon, Temecula, CA.

General immunoassay techniques are well known in the art. Guidance for optimization of parameters can be found in, for example, Wu, Quantitative Immunoassay: A Practical Guide for Assay Establishment, Troubleshooting, and Clinical Application, 2000, AACC Press; Principles and Practice of Immunoassay, Price and Newman, eds., 1997, Groves Dictionaries, Inc.; The Immunoassay Handbook, Wild, ed., 2005, Elsevier Science Ltd.; Ghindilis, Pavlov and Atanassov, Immunoassay Methods and Protocols, 2003, Humana Press; Harlow and Lane, Using Antibodies: A Laboratory Manual, 1998, Cold Spring Harbor Laboratory Press; and Immunoassay Automation: An Updated Guide to Systems, Chan, ed., 1996, Academic Press.

In certain embodiments, the presence or decreased or increased presence of one or more biomarkers is indicated by a detectable signal (e.g., a blot, fluorescence, chemiluminescence, color, radioactivity) in an immunoassay. This detectable signal can be compared to the signal from a control sample or to a threshold value. In some embodiments, decreased presence is detected, and the presence or increased risk of cancer is indicated, when the detectable signal of biomarker(s) in the test sample is at least about 10%, 20%, 30%, 50%, 75% lower in comparison to the signal of antibodies in the reference sample or the predetermined threshold value. In other embodiments, an increased presence is detected, and the presence or increased risk of cancer is indicated, when the detectable signal of biomarker(s) in the test sample is at least about 1-fold, 2-fold, 3-fold, 4-fold or more, greater in comparison to the signal of antibodies in the reference sample or the predetermined threshold value.

In some embodiments, the results of the biomarker level determinations are recorded in a tangible medium. For example, the results of diagnostic assays (e.g., the observation of the presence or decreased or increased presence of one or more biomarkers) and the diagnosis of whether or not there is an increased risk or the presence of cancer or a metabolic disease can be recorded, e.g., on paper or on electronic media (e.g., audio tape, a computer disk, a CD, a flash drive, etc.).

In other embodiments, the methods further comprise the step of providing the diagnosis to the patient (i.e., the subject) and/or the results of treatment.

5. Compositions and Administration

In another aspect, the present invention provides pharmaceutical compositions. In some embodiments, the pharmaceutical composition comprises a conjugate comprising a histone deacetylase (HDAC) inhibitor, a retinoid, and a polymer containing a plurality of hydroxyl groups, in which the HDAC inhibitor and retinoid are covalently linked to the hydroxyl groups of the polymer, and a pharmaceutically acceptable carrier. In some embodiments, the HDAC inhibitor is a short-chain fatty acid.

As non-limiting examples, retinoids that can be used in the conjugates of the present invention include all trans retinoic acid (RA), retinol, retinal, isotretinoin, alltretinoin, etretinate, acitretin, tazarotene, bexarotene, adapalene, seletinoid G, a retinyl ester, fenretinide, derivatives thereof, and any combination thereof. Suitable retinyl esters include retinyl acetate, retinyl butyrate, retinyl propionate, retinyl palmitate, and any combination thereof. In particular embodiments, the retinoid is all trans retinoic acid (RA).

In some embodiments, the HDAC inhibitor that is used in the conjugate is an SCFA. Suitable SCFAs include, but are not limited to, propionate, butyrate, isobutyrate, valerate, isovalerate, and any combination thereof. In particular embodiments, the SCFA is butyrate or propionate. Any other HDAC inhibitor described herein or known to one of skill in the art can be used.

In some embodiments, the conjugate is BURA, e.g., BURA50 or BURA100. In some embodiments, the conjugate is PRORA, e.g., PRORA100.

In some embodiments, a pharmaceutical composition of the present invention further comprises a microRNA (miR) or a mimic thereof and a pharmaceutically acceptable carrier. In some embodiments, the pharmaceutical composition comprises miR-22. In some embodiments, the miR-22 comprises a nucleotide sequence having at least about 75% identity (e.g., at least about 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:1. In particular embodiments, the miR-22 comprises the nucleotide sequence set forth in SEQ ID NO:1. In some embodiments, a pharmaceutical composition comprising a conjugate of the invention and miR-22 is useful for the treatment of cancer (e.g., colon or liver cancer).

In some embodiments, a pharmaceutical composition of the present invention further comprises a microRNA (miR) inhibitor and a pharmaceutically acceptable carrier. In some embodiments, the pharmaceutical composition comprises a miR-22 inhibitor. In some embodiments, the miR-22 inhibitor is an oligonucleotide. In some embodiments, the oligonucleotide comprises a nucleic acid sequence that hybridizes to miR-22 and reduces miR-22 expression. In some embodiments, the oligonucleotide comprises unmodified and/or modified nucleotides. In some embodiments, the miR-22 inhibitor comprises a nucleotide sequence having at least about 75% identity (e.g., at least about 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity) to SEQ ID NO:2. In particular embodiments, the miR-22 inhibitor comprises the nucleotide sequence set forth in SEQ ID NO:2. In some embodiments, a pharmaceutical composition comprising a conjugate of the invention and a miR-22 inhibitor is useful for the treatment of a metabolic disease (e.g., metabolic syndrome, obesity, type 2 diabetes).

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, intravenously, parenterally, or rectally.

In some embodiments, a pharmaceutical composition described herein comprises a nanoemulsion. In some embodiments, a pharmaceutical composition of the present invention further comprises a resistant starch. In other embodiments, the pharmaceutical composition further comprises a probiotic agent. In some other embodiments, the pharmaceutical composition comprises a prebiotic agent. In some embodiments, the pharmaceutical composition further comprises both a probiotic agent and a prebiotic agent. Suitable prebiotic agents include, but are not limited to, apple pectin, inulin (or an ester thereof), and a combination thereof. In some instances, a probiotic agent is a bacterium that produces an SCFA (e.g., butyrate, propionate) such as *Roseburia hominis* or *Propionibacterium freudenreichii.*

In some embodiments, a pharmaceutical composition of the present invention further comprises a delivery-enhancing agent. In some embodiments, the delivery-enhancing agent comprises a cyclodextrin. Cyclodextrins, which are a family of compounds that comprise cyclic oligosaccharides, can take the form of alpha-cyclodextrins (having a 6-membered ring), beta-cyclodextrins (having a 7-membered ring), or gamma cyclodextrins (having an 8-membered ring). Cyclodextrins can increase the aqueous solubility of compounds and can increase bioavailability and stability. Folateconjugated amphiphilic cyclodextrins and derivatives thereof can be used for tumor targeting. Polycationic amphiphilic cyclodextrins enhance the interaction of compounds with cell membranes. Non-limiting examples of particularly useful cyclodextrins include Captisol® and Dexolve™ (sulfobutyl-ether-beta-cyclodextrin). Captisol® is useful for, among other things, improving the solubility, stability, bioavailability or compounds for administration, as well as decreasing volatility, irritation, smell, or taste.

In some embodiments, a delivery-enhancing agent comprises inactivated bacteria. Encapsulating the conjugates described herein into inactivated bacteria is especially useful for oral administration, as the retinoids and HDAC inhibitors can be delivered to the gut with increased activity. This method is further described in PCT Application Publication No. WO/2016/069740, hereby incorporated by reference for all purposes.

In some embodiments, the delivery-enhancing agent comprises an inulin. Inulins are a class of naturally occurring polysaccharides that belong to a class of dietary fibers known as fructans. In humans, inulins are indigestible, whereas bacterial fermentation can lead to the generation of butyrate and propionate from inulins. Because of their resistance to acids and human digestive enzymes, inulins find utility for oral drug delivery, in particular the delivery of drugs to the colon, where they can be readily absorbed through the gut epithelium. Inulin esters are also useful for methods and compositions of the present invention. Suitable inulin esters include, but are not limited to inulin butyrate esters, inulin propionate esters, and a combination thereof.

In some embodiments, an active agent (e.g., a conjugate of the invention) is encapsulated (e.g., nanoencapsulated). In some embodiments, the compositions of the present invention comprise active agents that are encapsulated (e.g., with glucosamine butyrate or a glucosamine butyrate-gelatin matrix). In some embodiments, an active agent is encapsulated in a matrix that comprises an emulsifier (e.g., a monoester, diester, or organic ester of a glyceride), a carbohydrate hydrocolloid, an unmodified or modified resistant starch, a pectin, a glucan, a cyclodextrin, a maltodextrin, or a protein (e.g., a casein, whey, soy).

Furthermore, one or more active agents (e.g., a conjugate of the invention) can be complexed, e.g., in a liposome, in a nanoparticle, in a supramolecular assembly, or an ion pair.

In some embodiments, a composition of the present invention comprises a Eudragit® polymer. Eudragit® is useful for protecting compounds from being dissolved in the stomach, allowing them to be available for release and in more distal regions of the GI tract. Eudragit®L, S, FS, and E polymers are available with acidic or alkaline groups that allow for pH-dependent drug release. Eudragit® RL and RS polymers (cationic groups) and Eudragit® NM polymer with neutral groups enable time-release of drugs. Eudragit® is commercially available from Evonik.

In some embodiments, targeting delivery of an active agent or compound (e.g., delivery of a conjugate of the invention) to the colon is especially desired. While useful for other routes and modes of delivery, encapsulation of active agents or compounds in polymeric micelles, inulins (and esters thereof), nanoparticles, or cross-linked chitosan microspheres are especially useful for delivery to the colon.

For inulin-based delivery (e.g., tablets and capsules), a three-component design can be used, wherein the three components include: (1) a hard gelatin enteric-coated capsule (for carrying two pulses), (2) first-pulse granules (for rapid release in intestine), and (3) second-pulse matrix tablet (for slow release in the colon).

Nanoparticles can be made with Eudragit® S100. Alternatively, mucoadhesive nanoparticles can be created with trimethylchitosan (TMC). Also, a mix of polymers (e.g., PLGA, PEG-PLGA, and PEG-PCL) can be used to obtain a sustained drug delivery.

For cross-linked chitosan microspheres, a multiparticulate system comprising pH-sensitive properties and specific biodegradability for colon-targeted delivery of agents such as a conjugate of the invention. As a non-limiting example, cross-linked chitosan microspheres can be prepared from an emulsion system using liquid paraffin as the external phase and a solution of chitosan in acetic acid as the disperse phase. The multiparticulate system is prepared by coating cross-linked chitosan microspheres exploiting Eudragit® L-100 and S-100 as pH-sensitive polymers.

Furthermore, cellulose acetate butyrate (CAB) can be used to enhance colonic delivery (e.g., of a conjugate of the invention).

In some embodiments, a composition of the present invention comprises an active agent (e.g., a conjugate of the invention) in an amount that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% by weight. In some embodiments, the active agent is between about 1%-10%, 1%-20%, 1%-30%, 1%-40%, 1%-50%, 1%-60%, 1%-70%, 1%-80%, 1%-90%, 1%-100%, 10%-20%, 10%-30%, 10%-40%, 10%-50%, 10%-60%, 10%-70, 10%-80, 10%-90, 10%-100%, 20%-30%, 20%-40%, 20%-50%, 20%-60%, 20%-70%, 20%-80%, 20%-90%, 20%-100%, 30%-40%, 30%-50%, 30%-60%, 30%-70%, 30%-80%, 30%-90%, 30%-100%, 40%-50%, 40%-60%, 40%-70%, 40%-80%, 40%-90%, 40%-100%, 50%-60%, 50%-70%, 50%-80%, 50%-90%, 50%-100%, 60%-70%, 60%-80%, 60%-90%, 60%-100%, 70%-80%, 70%-90%, 70%-100%, 80%-90%, 80%-100%, or 90%-100% by weight.

In some embodiments, a composition of the present invention comprises an active agent (e.g., a conjugate of the invention) in an amount that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% by volume. In some embodiments, the active agent is between about 1%-10%, 1%-20%, 1%-30%, 1%-40%, 1%-50%, 1%-60%, 1%-70%, 1%-80%, 1%-90%, 1%-100%, 10%-20%, 10%-30%, 10%-40%, 10%-50%, 10%-60%, 10%-70, 10%-80, 10%-90, 10%-100%, 20%-30%, 20%-40%, 20%-50%, 20%-60%, 20%-70%, 20%-80%, 20%-90%, 20%-100%, 30%-40%, 30%-50%, 30%-60%, 30%-70%, 30%-80%, 30%-90%, 30%-100%, 40%-50%, 40%-60%, 40%-70%, 40%-80%, 40%-90%, 40%-100%, 50%-60%, 50%-70%, 50%-80%, 50%-90%, 50%-100%, 60%-70%, 60%-80%, 60%-90%, 60%-100%, 70%-80%, 70%-90%, 70%-100%, 80%-90%, 80%-100%, or 90%-100% by volume.

In some embodiments, a composition of the present invention comprises an inactive agent (i.e., not a conjugate of the invention) in an amount that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% by weight. In some embodiments, the inactive agent is between about 1%-10%, 1%-20%, 1%-30%, 1%-40%, 1%-50%, 1%-60%, 1%-70%, 1%-80%, 1%-90%, 1%-100%, 10%-20%, 10%-30%, 10%-40%, 10%-50%, 10%-60%, 10%-70, 10%-80, 10%-90, 10%-100%, 20%-30%, 20%-40%, 20%-50%, 20%-60%, 20%-70%, 20%-80%, 20%-90%, 20%-100%, 30%-40%, 30%-50%, 30%-60%, 30%-70%, 30%-80%, 30%-90%, 30%-100%, 40%-50%, 40%-60%, 40%-70%, 40%-80%, 40%-90%, 40%-100%, 50%-60%, 50%-70%, 50%-80%, 50%-90%, 50%-100%, 60%-70%, 60%-80%, 60%-90%, 60%-100%, 70%-80%, 70%-90%, 70%-100%, 80%-90%, 80%-100%, or 90%-100% by weight.

In some embodiments, a composition of the present invention comprises an inactive agent (i.e., an agent or compound present in the composition that is not a conjugate of the invention) in an amount that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% by volume. In some embodiments, the inactive agent is between about 1%-10%, 1%-20%, 1%-30%, 1%-40%, 1%-50%, 1%-60%, 1%-70%, 1%-80%, 1%-90%, 1%-100%, 10%-20%, 10%-30%, 10%-40%, 10%-50%, 10%-60%, 10%-70, 10%-80, 10%-90, 10%-100%, 20%-30%, 20%-40%, 20%-50%, 20%-60%, 20%-70%, 20%-80%, 20%-90%, 20%-100%, 30%-40%, 30%-50%, 30%-60%, 30%-70%, 30%-80%, 30%-90%, 30%-100%, 40%-50%, 40%-60%, 40%-70%, 40%-80%, 40%-90%, 40%-100%, 50%-60%, 50%-70%, 50%-80%, 50%-90%, 50%-100%, 60%-70%, 60%-80%, 60%-90%, 60%-100%, 70%-80%, 70%-90%, 70%-100%, 80%-90%, 80%-100%, or 90%-100% by volume.

In pharmaceutical compositions that comprise a delivery enhancing agent, in some embodiments, the delivery-enhancing agent is present in an amount that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% by weight. In some embodiments, the delivery-enhancing agent is between about 1%-10%, 1%-20%, 1%-30%, 1%-40%, 1%-50%, 1%-60%, 1%-70%, 1%-80%, 1%-90%, 1%-100%, 10%-20%, 10%-30%, 10%-40%, 10%-50%, 10%-60%, 10%-70, 10%-80, 10%-90, 10%-100%, 20%-30%, 20%-40%, 20%-50%, 20%-60%, 20%-70%, 20%-80%, 20%-90%, 20%-100%, 30%-40%, 30%-50%, 30%-60%, 30%-70%, 30%-80%, 30%-90%, 30%-100%, 40%-50%, 40%-60%, 40%-70%, 40%-80%, 40%-90%, 40%-100%, 50%-60%, 50%-70%, 50%-80%, 50%-90%, 50%-100%, 60%-70%, 60%-80%, 60%-90%, 60%-100%, 70%-80%, 70%-90%, 70%-100%, 80%-90%, 80%-100%, or 90%-100% by weight.

In some embodiments, the delivery-enhancing agent is present in an amount that is about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% by volume. In some embodiments, the delivery-enhancing agent is between about 1%-10%, 1%-20%, 1%-30%, 1%-40%, 1%-50%, 1%-60%, 1%-70%, 1%-80%, 1%-90%, 1%-100%, 10%-20%, 10%-30%, 10%-40%, 10%-50%, 10%-60%, 10%-70, 10%-80, 10%-90, 10%-100%, 20%-30%, 20%-40%, 20%-50%, 20%-60%, 20%-70%, 20%-80%, 20%-90%, 20%-100%, 30%-40%, 30%-50%, 30%-60%, 30%-70%, 30%-80%, 30%-90%, 30%-100%, 40%-50%, 40%-60%, 40%-70%, 40%-80%, 40%-90%, 40%-100%, 50%-60%, 50%-70%, 50%-80%, 50%-90%, 50%-100%, 60%-70%, 60%-80%, 60%-90%, 60%-100%, 70%-80%, 70%-90%, 70%-100%, 80%-90%, 80%-100%, or 90%-100% by volume a. Routes of Administration Exemplary formulations and routes of administration for the delivery of conjugates of the invention are described herein.

For oral administration, a pharmaceutical formulation or a medicament can take the form of, for example, a tablet or a capsule prepared by conventional means with a pharmaceutically acceptable excipient. The present invention provides tablets and gelatin capsules comprising: a conjugate of the invention, alone or in combination with other compounds, or a dried solid powder of these drugs, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners. In some embodiments, an amorphous solid dispersion of an active agent (e.g., a conjugate of the invention) is prepared that is suitable for oral delivery.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound(s).

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral or rectal administration is also contemplated. In a particular embodiment, the formulation is for oral administration.

Suitable formulations for transdermal application include an effective amount of one or more compositions or compounds described herein, optionally with a carrier. Particular carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time and means to secure the device to the skin. Matrix transdermal formulations may also be used.

The compositions and formulations set forth herein can be formulated for parenteral administration by injection, for example by bolus injection or continuous infusion. Formulations for injection can be presented in unit dosage form, for example, in ampules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient(s) can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient(s).

For administration by inhalation, the compositions of the present invention may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound(s) and a suitable powder base, for example, lactose or starch.

The compositions set forth herein can also be formulated in rectal compositions, for example, suppositories or retention enemas, for example, containing conventional suppository bases, for example, cocoa butter or other glycerides.

Furthermore, the active ingredient(s) can be formulated as a depot preparation. Such long-acting formulations can be administered by implantation (for example, subcutaneously or intramuscularly) or by intramuscular injection. Thus, for example, one or more of the compounds described herein can be formulated with suitable polymeric or hydrophobic materials (for example as an emulsion in an acceptable oil) or ion exchange resins, or as sparingly soluble derivatives, for example, as a sparingly soluble salt.

In particular embodiments, a pharmaceutical composition or medicament of the present invention can comprise (i) a therapeutically effective amount of a conjugate of the invention, e.g., a conjugate comprising a histone deacetylase (HDAC) inhibitor; (b) a retinoid; and (c) a polymer containing a plurality of hydroxyl groups, wherein the HDAC inhibitor and the retinoid are covalently attached to the polymer via the plurality of hydroxyl groups, alone or in combination with other compounds. The therapeutic agent(s) may be used individually, sequentially, or in combination with one or more other such therapeutic agents (e.g., a first therapeutic agent, a second therapeutic agent, a compound of the present invention, etc.). Administration may be by the same or different route of administration or together in the same pharmaceutical formulation.

b. Dosage

Pharmaceutical compositions or medicaments can be administered to a subject at a therapeutically effective dose to prevent, treat, re-sensitize, or control cancer (e.g., liver or colon cancer), or prevent, treat, or control a metabolic disease (e.g., NASH, NAFLD, diabetes, or obesity), as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular formulation in a particular subject. A unit dosage for oral administration to a mammal of about 50 to about 70 kg may contain between about 5 and about 500 mg, about 25-200 mg, about 100 and about 1000 mg, about 200 and about 2000 mg, about 500 and about 5000 mg, or between about 1000 and about 2000 mg of the active ingredient. A unit dosage for oral administration to a mammal of about 50 to about 70 kg may contain about 10 mg, 20 mg, 25 mg, 50 mg, 75 mg, 100 mg, 200 mg, 300 mg, 400 mg, 500 mg, 600 mg, 700 mg, 800 mg, 900 mg, 1,000 mg, 1,250 mg, 1,500 mg, 2,000 mg, 2,500 mg, 3,000 mg, or more of the active ingredient. Typically, a dosage of the active compound(s) of the present invention is a dosage that is sufficient to achieve the desired effect. Optimal dosing schedules can be calculated from measurements of active agent accumulation in the body of a subject. In general, dosage may be given once or more of daily, weekly, or monthly. Persons of ordinary skill in the art can easily determine optimum dosages, dosing methodologies and repetition rates.

Optimum dosages, toxicity, and therapeutic efficacy of the compositions of the present invention may vary depending on the relative potency of the administered composition and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

Optimal dosing schedules can be calculated from measurements of active ingredient accumulation in the body of a subject. In general, dosage is from about 1 ng to about 1,000 mg per kg of body weight and may be given once or more daily, weekly, monthly, or yearly. Persons of ordinary skill in the art can easily determine optimum dosages, dosing methodologies and repetition rates. One of skill in the art will be able to determine optimal dosing for administration of a conjugate of the invention to a human being following established protocols known in the art and the disclosure herein.

The data obtained from, for example, animal studies (e.g. rodents and monkeys) can be used to formulate a dosage range for use in humans. The dosage of compounds of the present invention lies preferably within a range of circulating concentrations that include the $ED_{50}$ with little or no toxicity. The dosage can vary within this range depending upon the dosage form employed and the route of administration. For any composition for use in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a chimeric protein, preferably a composition is from about 1 ng/kg to about 100 mg/kg for a typical subject.

A typical composition of the present invention for oral or intravenous administration can be about 0.1 to about 10 mg of active ingredient per patient per day; about 1 to about 100 mg per patient per day; about 25 to about 200 mg per patient per day; about 50 to about 500 mg per patient per day; about 100 to about 1000 mg per patient per day; or about 1000 to about 2000 mg per patient per day. Exemplary dosages include, but are not limited to, about 10 mg, 20 mg, 25 mg, 50 mg, 75 mg, 100 mg, 200 mg, 300 mg, 400 mg, 500 mg, 600 mg, 700 mg, 800 mg, 900 mg, 1,000 mg, 1,250 mg, 1,500 mg, 2,000 mg, 2,500 mg, 3,000 mg, or more of the active ingredient per patient per day. Methods for preparing administrable compositions will be known or apparent to those skilled in the art and are described in more detail in such publications as *Remington: The Science and Practice of Pharmacy,* 21st Ed., University of the Sciences in Philadelphia, Lippencott Williams & Wilkins (2005).

Exemplary doses of the compositions described herein include milligram or microgram amounts of the composition per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a composition depend upon the potency of the composition with respect to the desired effect to be achieved. When one or more of these compositions is to be administered to a mammal, a physician, veterinarian, or researcher may, for example, prescribe a relatively low dose at first, subsequently increasing the dose until an appropriate response is obtained. In addition, it is understood that the specific dose level for any particular mammal subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

In some embodiments, a pharmaceutical composition or medicament of the present invention is administered, e.g., in a daily dose in the range from about 1 mg of compound per kg of subject weight (1 mg/kg) to about 1 g/kg. In another embodiment, the dose is a dose in the range of about 5 mg/kg to about 500 mg/kg. In yet another embodiment, the dose is about 10 mg/kg to about 250 mg/kg. In another embodiment, the dose is about 25 mg/kg to about 150 mg/kg. A preferred dose is about 2, 3, 4, 5, 6, 7, 8, 9, 10, 12, 15, 18, 20, 25, 30, 40, or 50 mg/kg. The daily dose can be administered once per day or divided into subdoses and administered in multiple doses, e.g., twice, three times, or four times per day. However, as will be appreciated by a skilled artisan, compositions described herein may be administered in different amounts and at different times. The skilled artisan will also appreciate that certain factors may influence the dosage and timing required to effectively treat a subject, including but not limited to the severity of the disease or malignant condition, previous treatments, the general health and/or age of the subject, and other diseases present. Moreover, treatment of a subject with a therapeutically effective amount of a composition can include a single treatment or, preferably, can include a series of treatments.

To achieve the desired therapeutic effect, compounds or agents described herein may be administered for multiple days at the therapeutically effective daily dose. Thus, therapeutically effective administration of compounds to treat cancer (e.g., liver or colon cancer) or a metabolic disease (e.g., obesity, diabetes, NASH, or NAFLD) in a subject may require periodic (e.g., daily) administration that continues for a period ranging from three days to two weeks or longer. Compositions set forth herein may be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week, once every two weeks, once every three weeks, once every four weeks, or even less frequently.

In some cases, the recitation of a dose "per day" refers to the amount of drug administered each day. In other cases, the "per day" dose refers to the average amount per day of drug administered over a period of time. Thus, if a drug is administered once a week at 100 mg, then the "per day" dose would be approximately equal to (100 mg/7 days=) 14.3 mg per day.

Following successful treatment, it may be desirable to have the subject undergo maintenance therapy to prevent the recurrence of the cancer (e.g., liver or colon cancer) or metabolic disease (e.g., obesity, diabetes, NASH, or NAFLD).

Determination of an effective amount is well within the capability of those skilled in the art, especially in light of the detailed disclosure provided herein. Generally, an efficacious or effective amount of an composition is determined by first administering a low dose or small amount of the composition, and then incrementally increasing the administered dose or dosages, adding a second or third medication as needed, until a desired effect of is observed in the treated subject with minimal or no toxic side effects.

Single or multiple administrations of the compositions are administered depending on the dosage and frequency as required and tolerated by the patient. In any event, the composition should provide a sufficient quantity of the compositions of this invention to effectively treat the patient. Generally, the dose is sufficient to treat, improve, or ameliorate symptoms or signs of disease without producing unacceptable toxicity to the patient.

6. Kits, Containers, Devices, and Systems

A wide variety of kits, systems, and compositions can be prepared according to the present invention, depending upon the intended user of the kit and system and the particular needs of the user. In some embodiments, the present invention provides a kit that includes a conjugate of the invention, e.g., BURA50, BURA100, or PRORA100, alone or in combination with other compounds. In some embodiments, the kit further comprises a microRNA (miR), e.g., miR-22, or an microRNA inhibitor, e.g., an miR-22 inhibitor. In some embodiments, the kit contains a pharmaceutical composition of the present invention as described herein.

In some embodiments, the present invention provides a kit that includes a container containing a conjugate of the invention. In some embodiments, the kit further includes a container containing a miR (e.g., miR-22) or an miR inhibitor (e.g., an miR-22 inhibitor).

The compositions of the present invention, including but not limited to compositions containing a conjugate of the invention, may, if desired, be presented in a bottle, jar, vial, ampoule, tube, or other container-closure system approved by the Food and Drug Administration (FDA) or other regulatory body, which may provide one or more dosages containing the active ingredient. The package or dispenser may also be accompanied by a notice associated with the container in a form prescribed by a governmental agency regulating the manufacture, use, or sale of pharmaceuticals, or the notice indicating approval by the agency. In certain aspects, the kit may include a formulation or composition as taught herein, a container closure system including the formulation or a dosage unit form including the formulation, and a notice or instructions describing a method of use as taught herein.

In some embodiments, the kit includes a container which is compartmentalized for holding the various elements of a formulation (e.g., the dry ingredients and the liquid ingredients) or composition, instructions for making the formulation or composition, and instructions for preventing, treating, or controlling cancer (e.g., liver cancer, colon cancer (e.g., colon cancer in a subject who has one or more colon polyps)) or a metabolic disease (e.g., diabetes, obesity, NASH, NAFLD). In some instances, kits of the present invention are used to treat colon cancer in a subject who has one or more colon polyps. In certain embodiments, the kit may include the pharmaceutical preparation in dehydrated or dry form, with instructions for its rehydration (or reconstitution) and administration.

Kits with unit doses of the active composition, e.g. in oral, rectal, transdermal, or injectable doses (e.g., for intramuscular, intravenous, or subcutaneous injection), are provided. In such kits, in addition to the containers containing the unit doses will be an informational package insert describing the use and attendant benefits of the composition in preventing, treating, or controlling cancer (e.g., liver cancer, colon cancer) or a metabolic disease. Suitable active compositions and unit doses are those described herein.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

7. Examples

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1. Nanoparticle-Based Oral Delivery of a miR-22 Inducer for Colon Cancer Treatment This example describes the production of a novel miR-22 inducer that is orally deliverable for colon cancer treatment. This novel compound provides benefits for colon cancer treatment as well as potential prevent reoccurrence because the targeted pathway is implicated in colon carcinogenesis. Additionally, this nano-drug is expected to have low toxicity and be cost-effective.

Abstract

A standard chemotherapy regimen for colorectal cancer (CRC) may contain a complicated combination of drugs, which have many side effects, require injection, and are high-cost. Development of a low-toxicity and oral treatment would greatly improve care for CRC patients. Emerging evidence has revealed the importance of diet, acting through gut microbiota, on CRC development. The tumor suppressor miR-22, which has a reduced expression level in human CRC, is inducible by beneficial chemicals generated directly or indirectly by the gut microbiota. Those chemicals are bile acids, retinoids, vitamin D3, and short-chain fatty acids (SCFAs). Among SCFAs, only those that have histone deacetylase (HDAC) inhibitory properties such as propionate, butyrate, and valerate induce miR-22. Moreover, miR-22 can be induced to a higher level when an HDAC inhibitor is used in combination with a retinoid. Thus, we have developed nano-drugs that can be delivered orally, aiming to induce miR-22 and combat CRC.

One of the nano-drugs that we have tested is named BURA, which is produced by covalent linking of butyric acid and all-trans retinoic acid (RA) to polyvinyl alcohol (PVA) assembling into nanomicelles. We have studied the treatment effect of BURAs at molar ratios of 50:1 and 100:1 (butyric acid:RA) and revealed very promising results in azoxymethane and dextran sodium sulfate (AOM/DSS)-induced orthotopic colon tumor mouse models. These BURA nano-formulations ensure that these two chemicals are released simultaneously and gradually to exert their interactive combined benefits, which does not occur if only one chemical is used. BURA is deliverable orally, which is preferred by patients. It also saves dispensing and administrative cost. Additionally, because butyrate is a nutrient and RA is an FDA-approved drug, the safety of the active ingredients in BURA suggests the likelihood for immediate translational potential.

Introduction

Colorectal cancer (CRC) is the leading cause of cancer death. Although the disease is treatable, a standard chemotherapy regimen for CRC may contain a complicated combination of drugs that have many side effects and require injection, which is inconvenient and costly. Development of a low-toxicity, oral, low-cost treatment would greatly improve care for CRC patients. Our strategy is to target the pathways by which cancer arises in the first place. Emerging evidence has revealed the importance of the gut microbiota on CRC development, indicating that targeting gut microbiota-derived signaling is an effective way to treat CRC.

Our published data revealed that the tumor suppressor miR-22, which has reduced expression in human CRC specimens, is inducible by beneficial chemicals generated directly or indirectly by the gut microbiota. Those chemicals are bile acids, retinoids, vitamin D3, and short-chain fatty acids (SCFAs). Among SCFAs, only butyrate, propionate, and valerate, which have histone deacetylase (HDAC) inhibitory properties, induce miR-22. Suberanilohydroxamic acid (SAHA), an FDA-approved anti-cancer HDAC inhibitor, also induces miR-22. Moreover, miR-22 can be induced to a higher level when an HDAC inhibitor is used in combination with a retinoid than as a single chemical treatment. Furthermore, we have uncovered several novel mechanisms by which miR-22 has an anti-cancer effect. Because of these promising findings, we have developed nano-drugs that can be delivered orally, aiming to induce miR-22 and combat CRC.

One of the nano-drugs that we have generated and tested is named BURA, which is produced by covalent conjugation of butyric acid and all-trans retinoic acid (RA) in polyvinyl alcohol at different molar ratios forming nanomicelles. This nano-formulation ensures that these two chemicals are released simultaneously and gradually to exert their interactive combined beneficial effects, some of which do not occur if only a single chemical is used. We have tested BURA50 and BURA100 (butyric acid:RA=50:1 or 100:1) in orthotopic colon tumor mouse models and both formulations revealed promising tumor treatment results.

Here, we describe the production of BURA250, BURA500, and BURA1000 and a comparison of their effects with existing BURA50 and BURA100 on inducing miR-22 and silencing CYCLIN A2 as well as HDACs in colon cancer cell lines. An analysis of their effects in differentiation, apoptosis, and anti-proliferation is also described. Colon cancer cell lines including Caco-2 and HCT116, which are fast-growing and differ genetically, are used.

We also describe an examination of the toxicity, bio-distribution, and anti-tumor effects of a selected BURA in mice. For this, the BURA formulation with the highest anti-cancer effect in cell cultures is studied for its toxicity and bio-distribution in mice. A pilot study is also performed to test the nano-drug's anti-cancer effect in comparison with the free chemicals at the same molar ratio in a colon cancer mouse model. We describe the use of ApcΔ14/+ mice, which develop tumors exclusively in the large intestine, covering both the proximal and distal colon. This is important because CRC is formed in the large intestine in humans. Additionally, tumors formed in different locations can be distinctively different and respond to drugs differently.

The nano-drugs described herein are effective, affordable, and can be delivered orally for CRC treatment. They can also prevent CRC reoccurrence because they target the signaling pathways involved in the occurrence of CRC. Further, since butyrate is a nutrient and RA is an FDA-approved drug, the safety of these chemicals indicates the potential for immediate commercial translation.

Significance and Rigor of Prior Research

Most CRC cases are sporadic, suggesting the importance of environmental influences. Epidemiologically, the incidence of CRC is influenced by Western diet (WD), i.e., high meat and sugar consumption [1-5]. Many studies have revealed the importance of the gut microbiota, whose composition and metabolites are largely influenced by diet, in CRC. Thus, it is particularly important to understand how diet, acting through the gut microbiota, affects CRC development. By understanding the pathways that lead to CRC, we can design treatments that alter these pathways.

Figure 9:
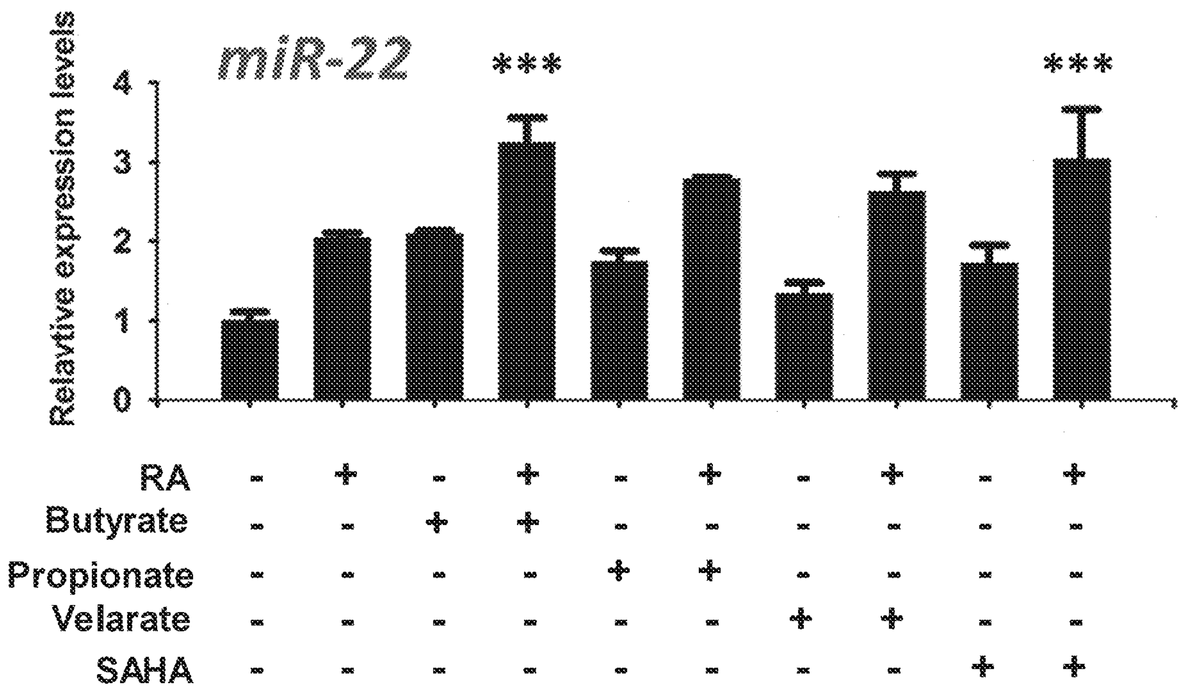
FIG. 9. The combined effect of RA (10 μM) and HDAC inhibitors SAHA (5 μM), butyrate (5 mM), propionate (10 mM), and velarate (10 mM) on inducing miR-22 in HCT116 cells. Mean±SD, *$p<0.05$; $p<0.01$; *$p<0.0001$ vs. DMSO control, #$p<0.05$ vs. single agent treatment.

The significance of miR-22 in cancer and its induction by gut signaling molecules: miR-22 is highly conserved across many vertebrate species, suggesting it has functional importance [6-10]. The role of miR-22 in cancer protection has been demonstrated in various cancers and cancer animal models [6-10]. Our published data showed that miR-22 level is reduced in human colon cancer and liver cancer specimens [11, 12]. We have uncovered for the first time that the level of miR-22 can be induced by chemicals that are normally generated in the digestive tract such as bile acids, vitamin D3, retinoids including all-trans retinoic acid (RA), and short-chain fatty acids (SCFAs) that have histone deacetylase (HDAC) inhibitory properties [11, 12] (FIG. 9). We also showed that miR-22 expression is bile acid receptor (FXR) and RA receptor (RARβ)-dependent [11, 12]. Moreover, the expression level of FXR, SCFA receptors, as well as RA-associated signaling are all coordinately reduced in human CRC specimens (FIG. 11). Together, these data strongly suggest that miR-22 is regulated by signaling derived from the gut and that miR-22 as well as its inducers potentially can be used to prevent and treat colon cancer.

The interaction between HDAC inhibitors and RA: Another novel observation we made is that miR-22 can be induced to a higher level when a retinoid is used in combination with a HDAC inhibitor as compared to single chemical treatment. Additionally, combinations of HDAC inhibitors plus retinoids potently induce apoptosis of cancer cells, but not normal cells [13]. Thus far, we have tested several HDAC inhibitors including trichostatin [13], scriptaid [13], suberanilohydroxamic acid (SAHA), an FDA-approved anti-cancer drug, as well as three SCFAs (FIG. 9).

Figure 12:
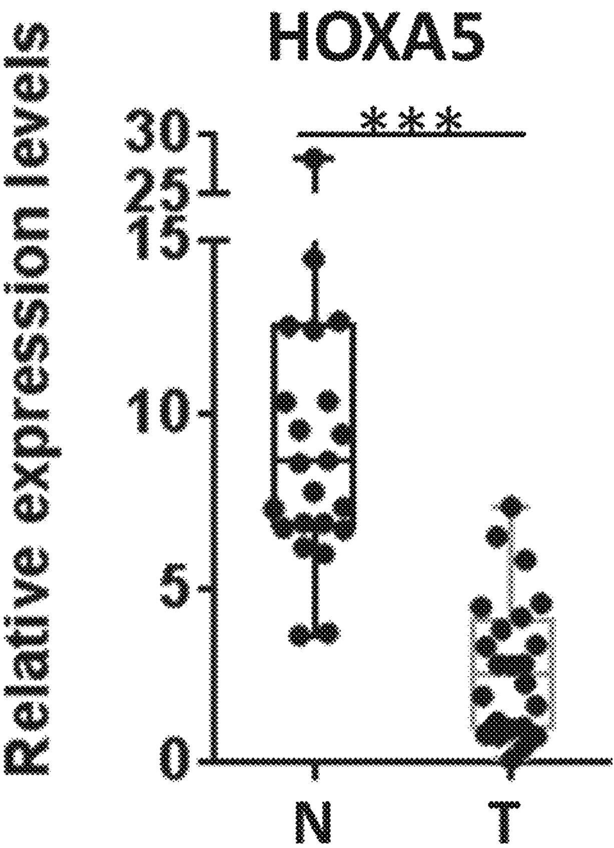
FIG. 12. HOXA5 mRNA levels in CRC (T) vs. their adjacent benign (N) specimens (n=20).

To avoid using synthetic chemicals, we are focusing on SCFAs that are produced by commensal microbiota through fermentation of indigestible fiber. One such SCFA, butyrate, promotes RA production in colon dendritic cells by inducing expression of ALDH1A1 [13-15]. Our novel data also showed that HDAC inhibitors including SAHA and butyrate induced the expression of RA receptor, i.e., RARβ (FIG. 12). Butyrate by itself can be used as an energy source to support cell growth and proliferation [16-18]. RA by itself is effective in inducing cancer cell differentiation, but not effective in inducing apoptosis [19]. However, when butyrate and RA are combined, they induce miR-22 to silence CYCLIN A2 and multiple HDACs as well as export oncogene NUR77 to the cytosol, thereby having anti-proliferative and apoptotic effects [11].

The effect of RA on cell differentiation: Due to the stem-like properties of cancer cells, the effect of chemotherapy can be transient. Depleting cancer stem cells by differentiation can have profound therapeutic implications and provide a survival benefit for patients. RA has a well-characterized effect on cell differentiation [19, 20]. The induction of HOXA5, which is reduced in CRCs shown in FIG. 11 below, is essential for RA-induced differentiation therapy [21]. Thus, it is important to retain the differentiation effect of RA.

Challenges for using RA and butyrate: RA is a very unstable chemical that is highly sensitive to light, oxygen, and high temperatures [22, 23]. Moreover, RA has side effects such as hypercalcemia, acute pancreatitis, etc. [24-26]. Butyrate, which is a food supplement, has been used to treat a variety of diseases including cancer [27]. However, clinical trials failed because of low bioavailability due to fast metabolism and clearance [28]. To overcome those issues and retain the synergism of RA plus butyrate, BURA is produced by covalent linking of butyric acid and all-trans-RA with polyvinyl alcohol (PVA) assembling into nanomicelles. We have studied the effect of BURAs at molar ratios of 50:1 and 100:1 (butyric acid:RA) and revealed promising treatment results in azoxymethane and dextran sodium sulfate (AOM/DSS)-induced colon tumor mouse models. These nano-formulations ensure that these two chemicals are released gradually and simultaneously to exert their combined interactive benefits.

The paradox of butyrate in CRC development and treatment: SCFAs have been extensively studied for their health benefits, including CRC prevention and treatment [16-18]. Ironically, supplementation with tributyrin orally or sodium butyrate via rectal instillation to antibiotic-treated APCMin+/−MSH−/− mice increases the number of proliferative cells, suggesting a tumorigenic effect [29]. This may in part be due to butyrate, which by itself is an energy source that may support the proliferation of stem cells. It is also surprising that tumor development in APCMin+/−MSH−/− mice is independent of microbial-driven inflammation or DNA damage, in contrast to many reports showing the importance of inflammatory cells and gut microbiota in promoting CRC [30-33]. It is important to note that most polyps formed in APCMin+/− or APCMin+/−MSH−/− mice are in the small intestine (>100 polyps/mouse) rather than in the colon (only about 7 polyps/mouse) [29]. Thus, the paradoxical effect of butyrate in CRCs could also in part be due to the animal models used. AOM/DSS-generated tumors are exclusively found in the distal colon. The current examples use an animal model that has tumors in both the proximal and distal colon. This is important because the tumors in the proximal colon are more likely to be adenomas than those in the distal colon, and the median lifespan is shorter after chemotherapy for patients with proximal compared to distal colon cancer [34].

The compounds of this invention target compromised gut signaling, regulated by gut microbiota-generated nutrients. This concept is supported by our data showing that polyps and CRCs have reduced abundance of bacteria that generate butyrate as well as compromised butyrate and RA signaling. Thus, it is highly likely that BURA can be used not only to treat CRC, but also to prevent cancer reoccurrence.

The nano-drugs are novel chemical entities and small in size (~20 nm). Butyric acid and RA are covalently conjugated with polyvinyl alcohol and are released from the nano-drug through slow hydrolysis, resulting in long-acting anti-cancer efficacy which is very different from the free drugs, i.e., RA and butyrate. Unlike current colon cancer treatments, BURA is orally deliverable, which is preferred by patients and in low-resource settings since oral administration saves dispensing and administrative cost. Furthermore, our data showed similar results in both the colon and liver, which suggests the significance of the studied pathway in both organs via the gut-liver axis. Thus, the disclosed treatment strategy can be used for both colon and liver cancers.

Figures 10A, 10B:
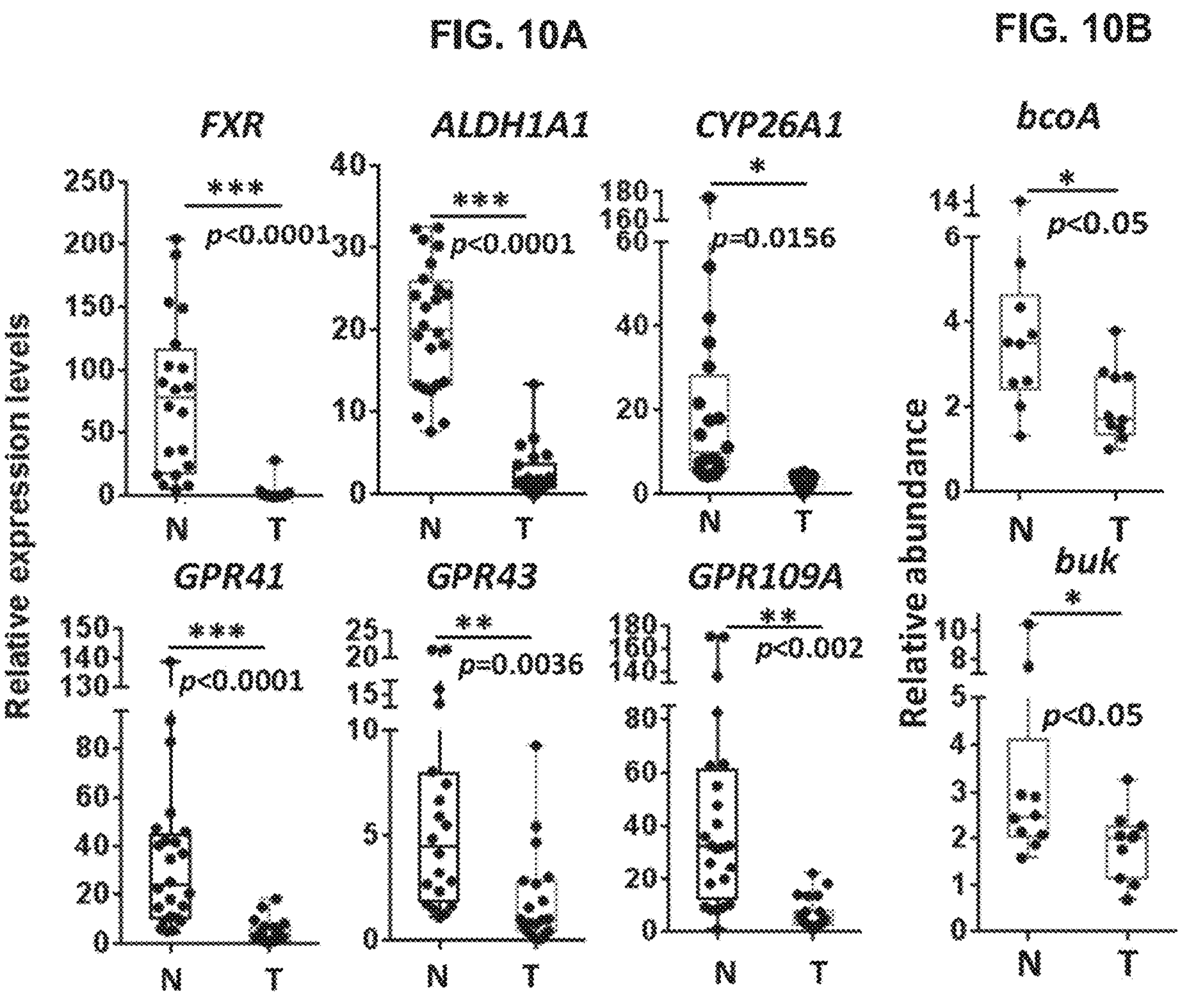
FIGS. 10A-10B. mRNA levels of FXR, ALDH1A1, and SCFA receptors (FIG. 10A) as well as the copy numbers of bcoA and buk (FIG. 10B) in CRCs (T, n=20) and their adjacent benign tissues (N). Mean±SD, *$p<0.05$; $p<0.01$; *$p<0.0001$.

Production of BURAs and Characterization of their Anti-Cancer Effects in Colon Cancer Cell Lines miR-22 is induced by chemicals naturally found in the digestive tract: We uncovered that miR-22 is consistently reduced in both human CRCs and hepatocellular carcinoma (HCCs) [11, 12]. If miR-22 can regulate both liver and gut health via the gut-liver axis, it is likely that the signaling commonly found in both organs can regulate the level of miR-22. We tested the effectiveness of chemicals present in both organs for regulating miR-22. The data showed that bile acids, SCFAs, and RA induced miR-22. Bile acids are generated by hepatic and gut bacterial enzymes, and SCFAs are produced by microbial fermentation of indigestible foods. The most abundant SCFAs in the gut are acetate, propionate, and butyrate, which constitute 95% of the SCFAs [35, 36]. Of those three SCFAs, propionate and butyrate have apparent HDAC inhibitory properties [36]. Valerate also has HDAC inhibitory properties but is present at a low concentration [35]. Our data revealed that miR-22 can be induced by RA, butyrate, propionate, valerate, and SAHA, and that combinations of RA plus HDAC inhibitors induce higher miR-22 expression than single chemical treatment (FIG. 9). In contrast, formate and acetate, which do not have HDAC inhibitory properties, were unable to induce miR-22. Due to the side effect of SAHA, it would be advantageous to use SCFAs.

miR-22 inducer signaling is reduced in CRCs and HCCs: As bile acids, SCFAs, and RA-induced miR-22 have cancer protective effects, those regulatory signals should be reduced in cancerous tissues as well. Indeed, data generated using patient specimens revealed that the mRNA levels of the bile acid receptor FXR, RA-generating enzyme ALDH1A1, RA oxidation enzyme CYP26A1, RA-regulated HOXA5, as well as SCFA receptors including GPR41, 43, and 109A were all reduced in both CRCs and HCCs compared with their adjacent benign specimens. FIG. 10A shows data generated from CRC patients (HCC data are not shown). Additionally, CRCs also had reduced copy number of bcoA, a bacterial butyrate-generating gene (FIG. 10B). Together, both butyrate-generating bacteria and host RA and SCFA signaling are reduced in CRCs.

miR-22 reduces HDACs and CYCLIN A2: We further investigated the downstream effects of miR-22 that can combat cancer. Our published data showed that miR-22 reduced HDAC1, HDAC4, and SIRT1 in liver cancer Huh7 and colon cancer HCT116 cells [11]. By sequence alignment, miR-22 also pairs with 3' UTR of the HDAC6, HDAC8, and HDAC11, suggesting a pivotal role of miR-22 in HDAC inhibition. Additionally, CYCLIN A2 is a validated miR-22 target [12]. Thus, miR-22 is likely to exhibit its anti-cancer effects by reducing protein deacetylases and CYCLIN A2, which have elevated expression in both CRCs and HCCs [12]. Other novel mechanism by which miR-22 has anti-cancer effects has been revealed by our recent publication [11].

Figure 11A:
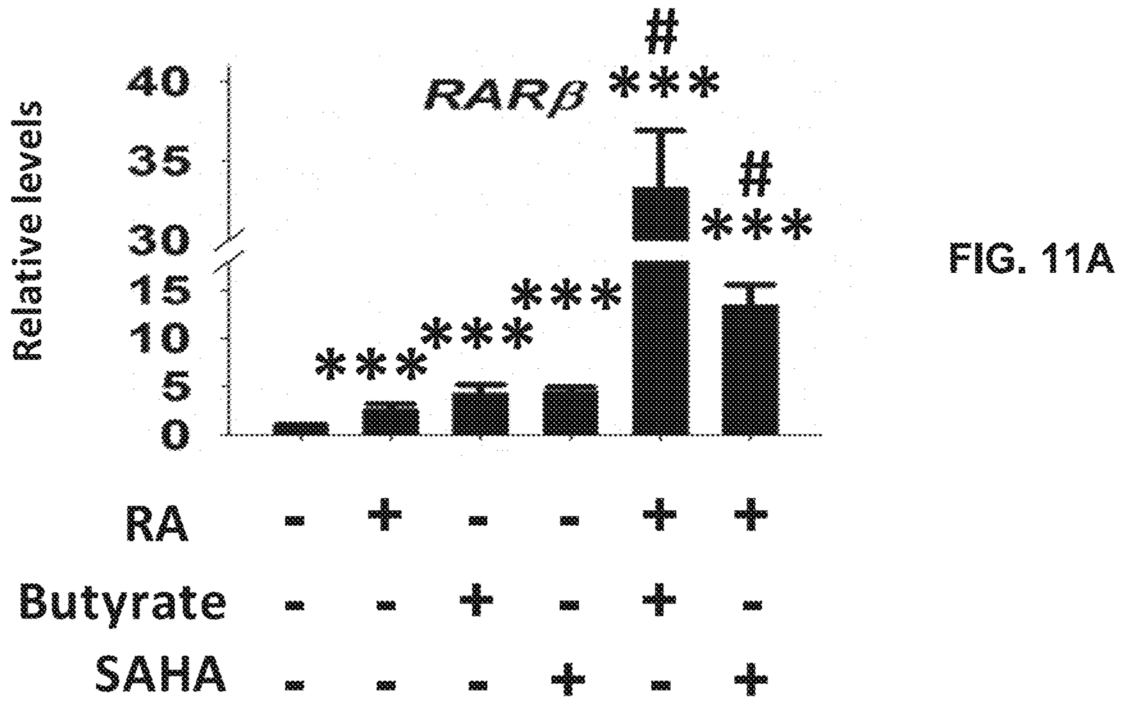
FIGS. 11A-11B. The combined effect of RA, butyrate, and SAHA on regulating the mRNA (FIG. 11A) and protein (FIG. 11B) levels of RARβ in HCT116 cells. Cells were treated with DMSO, RA (10 μM), butyrate (5 mM) and SAHA (5 μM) for 48 hrs. ***$p<0.001$ vs. DMSO control, #$p<0.05$ vs. single agent treatment.
Figure 11B:
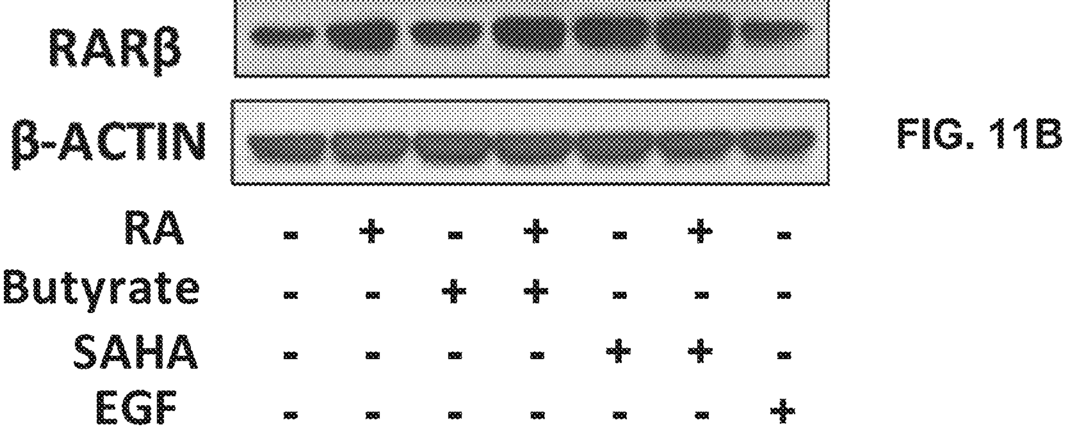

The interaction between butyrate and RA: Butyrate promotes RA production in colon dendritic cells by inducing expression of ALDH1A1 [15, 37, 38]. Our novel data revealed that SAHA and butyrate induced the expression of RA receptor, i.e., RARβ. When SAHA or butyrate and RA were used together, RARβ was expressed at a higher level compared to single chemical treatment in HCT116 colon cancer cells (FIGS. 11A-11B). In contrast, EGF, which promotes growth and does not has HDAC inhibitory effect, did not induce RARβ. Moreover, miR-22 itself as well as a combination of RA (0.025 mg/g body weight) and butyrate (1.2 mg/g body weight) are effective in treating colon tumors in xenograft models (intraperitoneal injection, 5 times/week, 2 weeks) [11]. The molar ratio of butyrate and RA used in that animal experiment was 1300:1. Thus, we propose generating BURAs with decreased RA content to reduce its potential toxicity for long-term administration.

Figure 2A:
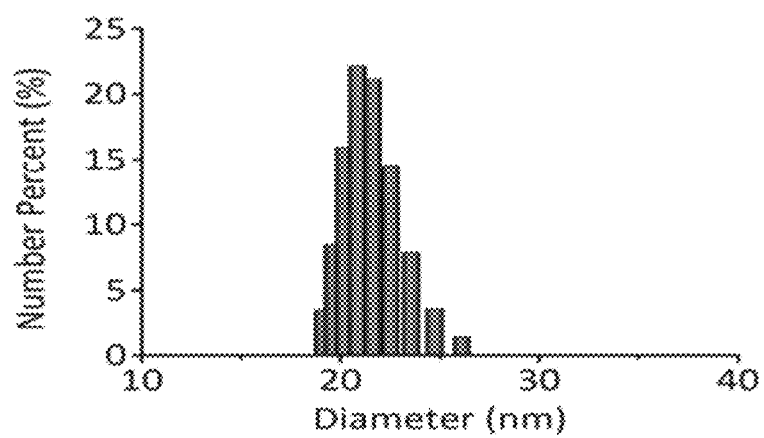
FIGS. 2A-2B. Dynamic light scattering (FIG. 2A) and transmission electron microscopy imaging (FIG. 2B) of 2 mg/mL BURA100 dissolved in saline. BURA100 was stained with uranyl acetate for transmission electron microscopy. BURA100 is small (~20 nm) and is expected to release from the nano-drug through slow hydrolysis, resulting in long-acting anti-cancer efficacy which is very different from the free drugs, i.e., retinoic acid and butyrate.
Figure 2B:
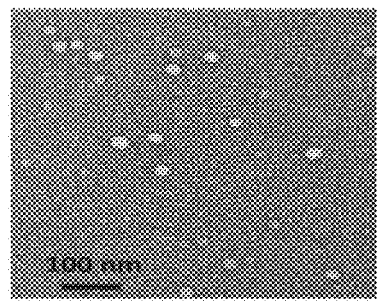
Figure 3:
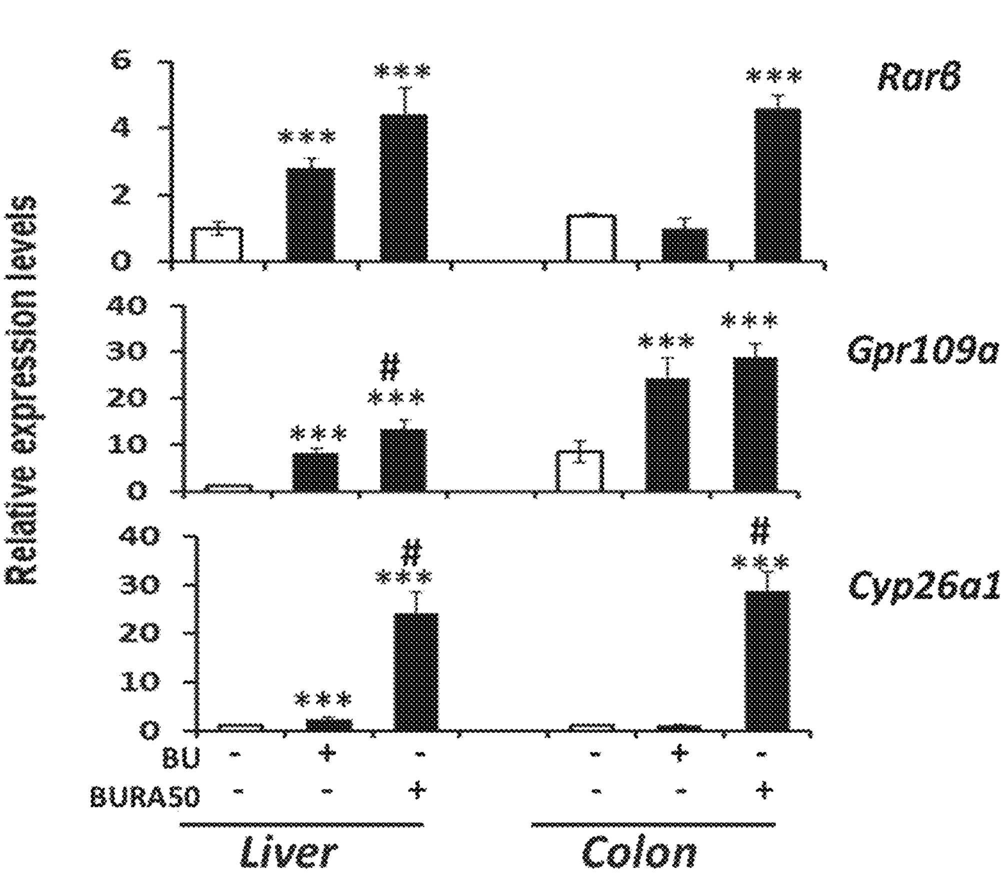
FIG. 3. BURA50 is orally deliverable and reaches the gut and liver within 2 hours to regulate gene expression. Within 2 hours post oral delivery of one dose of BURA50 (1.34 mg/g body weight), which was equivalent to 0.025 mg/g of RA and 0.6 mg/g of butyric acid, the mRNA level of retinoic acid-regulated genes, i.e., Rarβ and Cyp26b1 as well as the butyrate receptor gene Gpr109a, was highly induced in the colon and the liver. In addition, the fold induction was higher than that induced by PVA-butyric acid treatment. Mean±SD, ***$p<0.0001$, #$p<0.05$ BU vs. BURA50.
Figure 4A:
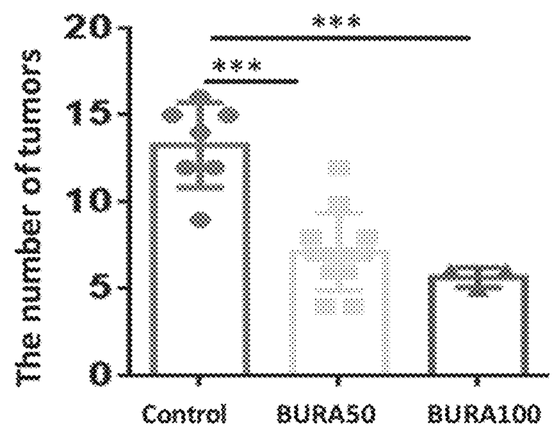
FIGS. 4A-4B. BURA50 and BURA100 are effective in treating colon tumors in azoxymethane (AOM) and dextran sodium sulfate (DSS) mouse models. The number of tumors (FIG. 4A) in AOM/DSS mouse models treated with saline (n=7), BURA50 (n=12), or BURA100 (n=3) at 1.34 mg/g body weight by daily oral gavage for 4 weeks. BURA treatment started after tumors had already formed. Exemplary images are shown in FIG. 4B. ***$p<0.001$.
Figure 4B:
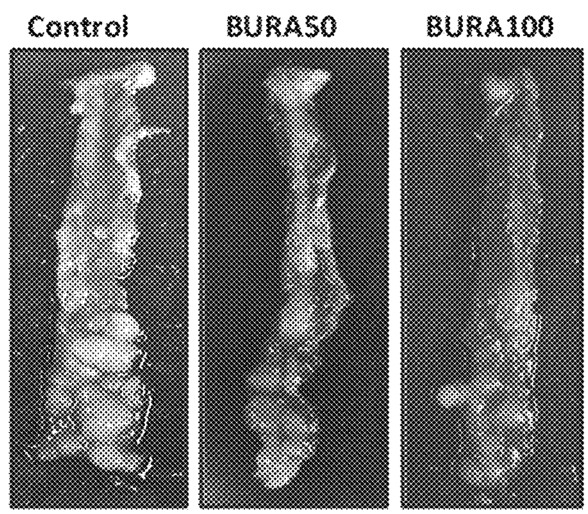
Figure 5:
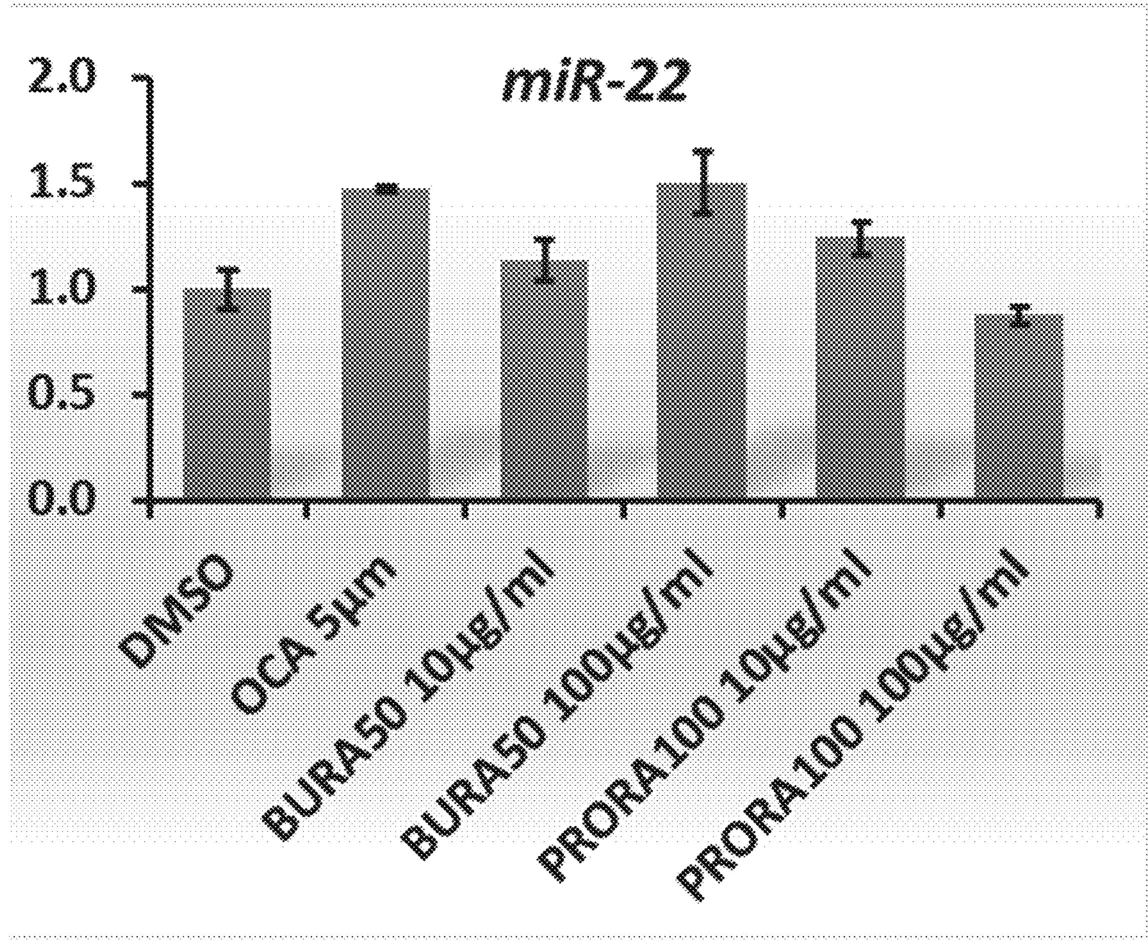
FIG. 5. BURA50 and PRORA100 induce miR-22 in human liver cancer Huh7 cells, demonstrating their tumor inhibitory effect. miR-22 levels in Huh7 cells treated with DMSO, obeticholic acid (OCA, 5 μM), BURA50 (10 and 100 μg/ml) or PRORA100 (10 and 100 μg/ml) for 48 h. *$p<0.05$.

BURA production: We generated novel nano-formulations of butyric acid and RA that covalently linked to the PVA backbone. BURA50 and BURA100 were produced with a molar ratio of butyric acid:RA at 50:1 and 100:1, respectively. Within 2 hours post oral delivery of one dose of BURA50 (1.34 mg/g body weight), which was equivalent to 0.025 mg/g of RA and 0.6 mg/g of butyric acid, the mRNA level of Rarβ, Cyp26b1, and Gpr109a was highly induced in the colon and the liver, and that the fold induction was higher than that induced by PVA-butyric acid treatment (FIG. 3). These findings suggested that orally delivered BURA50 reached the colon as well as the liver through enterohepatic circulation and exerted its transcriptional regulatory effect. BURA100 has a size of ~20 nm measured by dynamic light scattering (DLS) and transmission electron microscopy (TEM) (FIG. 2). Excitingly, our data showed that BURA50 as well as BURA100 had promising treatment effects in AOM/DSS-induced orthotopic colon tumor mouse models (FIG. 4). In addition, there was no obvious toxicity such as body weight loss and decreased activity after the treatment.

Overall Strategy: Our published data showed that combined free drugs, i.e., butyrate and RA with a molar ratio of 500:1 had a remarkable effect on inducing miR-22 and apoptosis of HCT116 colon cancer cells and at a molar ratio of 1300:1 was effective in treating colon cancer in xenograft mouse models [11]. Thus, we generate BURA250, BURA500, and BURA1000 and compare their anti-cancer effects. Their effects are studied on inducing miR-22 and silencing CYCLIN A2 as well as HDACs in colon cancer cell lines. In addition, the unique differentiation effect of RA as well as the apoptotic and anti-proliferative effects found in BURAs are analyzed in at least two colon cancer cell lines. We use the fastest growing CRC-derived Caco-2 and HCT116 (doubling time<24 hours) cell lines, which have different genetic makeup. The Caco-2 line is microsatellite stable and has wild-type KRAS, and yet HCT-116 has microsatellite instability as well as KRAS mutation [39].

Methodology: BURA production: PVA with a molecular weight of 27 kDa is dissolved in dimethyl sulfoxide (DMSO). 4-Dimethylaminopyridine (DMAP, catalytic amount), is added to the solution. Once it is dissolved, butyryl chloride (40% molar ratio to total hydroxyl groups of PVA is added dropwise while stirring. The resulting solution is stirred for 5 hours. RA is dissolved in a mixture of N,N-dimethylformamide (DMF) and dichloromethane at 4° C., followed by adding N,N'-dicyclohexylcarbodiimide (DCC). After 15 minutes, this mixture is added to PVA-butyric acid in the DMSO solution prepared above, followed by adding catalytic amount of DMAP. Under argon gas atmosphere and in the dark, the reaction mixture is stirred for 2 days. BURA is precipitated and washed with acetonitrile. The precipitate is dissolved in water and filtered through a 0.2-μm filter. The water solution is dialyzed against a large quantity of water (molecular cut-off size 6000-8000) for 2-3 days. Then, the solution is lyophilized to generate the final product. In addition, a near-infrared dye (cyanine5.5)-labeled BURA is produced using the same DCC/DMAP coupling of cyanine5.5 carboxylic acid with BURA for the cellular uptake and bio-distribution study based on our published method [40-42].

Physicochemical characterization of BURA: BURA is characterized by MALDI-TOF MS and/or Gel permeation chromatography. The particle sizes and zeta potential of BURA are analyzed by DLS particle sizer (Mastersizer 3000). The critical micelle concentration of BURA is determined by established fluorescence technique using pyrene or nile red as the optical probe [43]. The morphology of the micelles formed is visualized by TEM. The stability of the micelles upon the storage at room temperature and at 4° C. is studied using a DLS particle sizer.

Quantification of butyric acid and RA in BURAs: To quantify butyric acid and RA in BURAs, butyric acid and RA are released by hydrolysis, acidification, and extraction. Quantification of butyric acid is performed by gas chromatography with Agilent GC flame ionization detector (GC-FID) based on a published protocol [44]. RA is quantified via triple-quadrupole LC/MS/MS based on a published method, which offers the most effective RA detection with sensitivity and specificity [45].

Study the cellular uptake of BURAs in colon cancer cell lines: The cellular uptake efficiency of BURA in the colon cancer cells is qualitatively observed by confocal microscopy using the method described in our publication [41, 42]. HCT116 or Caco-2 cells is seeded and incubated with dye-labeled BURA for 1, 8, 16, and 24 hours followed by washing, fixation, and DNA staining using DAPI (4',6-diamidino-2-phenylindole). The intracellular uptake and subcellular localization of BURA are evaluated by confocal microscopy.

Study the anti-cancer effects of BURAs in colon cancer cell lines: The anti-cancer effects of BURA50 and BURA100, as well as the newly generated BURA250, 500, and 1000, are studied in at least two colon cancer cell lines to monitor the differentiation effect, which is unique for RA. PVA is used as a negative control. Free RA and/or butyrate are used as positive controls. We study the expression of genes encoding HOXA5, CDX1, SOX9, KLF4, and FOXO3A, which are transcriptionally induced by RA, and are the markers for intestinal development and differentiation [20, 21, 46-49]. Expression of stem cell markers including LGR5, CD133, CD44, and ALCAM are quantified in cells treated with and without the tested chemicals [21, 50]. MTT as well as TUNEL assay are performed to study anti-proliferative and apoptotic effects of BURAs. Moreover, a wound healing migration assay is done. All of these methods have been used previously [51]. Both time course and dose response studies are performed. The doses tested are within the range of the free chemicals that have an apoptotic effect on colon cancer cells as shown in our publications [11].

Results, Data Interpretation, and Alternative Approaches

We have extensive experience in the preparation of nanoparticles using different conjugation chemistry [41, 42, 52-55]. Additionally, we have already successfully generated nano BURA50 and BURA100. Nanoparticles generated from the 27-kDa PVA have shown good cell penetration

[41]. Optimization of nanoparticles can be achieved by varying the size of PVA, such as using PVA of 10 kDa. Another possibility is to change the esterification percentage of hydroxyl groups in PVA with butyric acid. Such modifications change the physiochemical properties of the nanoparticle, solubility, and size. To minimize the variation of nanoparticles from batch to batch, BURAs are produced at the same time and under the same conditions.

Toxicology: The LD50 of RA is 1.1 mg/g, oral, in Swiss mice [56]. When BURA50 that had 0.025 mg/g of RA was administered daily (1.34 mg/g, oral) for 4-weeks, we did not notice any apparent toxicity.

Bio-distribution: Cyanine5.5-labeled BURA is used for in vivo bio-distribution studies by optical imaging, with which we have extensive experience [41, 42, 57-59].

Anti-tumor animal trials: Animal trials are conducted using ApcΔ14/+ mice, which have tumors that develop only in the large intestine [60]. Such mice can be conveniently produced by breeding transgenic mice of carbonic anhydrase 1 (CA1)-driven Cre (Jackson Lab) with mice having LoxP sites inserted flanking exon14 of one Apc gene allele (APC580S/+ mice, NCI-Mouse Model of Human Cancers Consortium). CA1 expression is restricted to the colonic epithelial cells, in contrast to other models. Apcmin+/− female mice develop mammary tumors and Msh2 deletion mice develop lymphoma and skin tumors [61-63]. Another advantage of the ApcΔ14/+[CA1-Cre;APC580S/+] mice is that no mortality is reported even when they are 7.5 months of age, allowing study of long-term treatment effects [60].

Toxicology: Three-month-old C57BL/6 male and female mice are administered a BURA for 28 days consecutively (1.34 mg/g, oral). Free chemicals, i.e., butyrate and RA at the same molar ratio are used to compare the selected BURA. The following tests and assays are performed: (a) Body weight and food/water intake are recorded every 2 days. If mice have a 20% body weight loss or are not able to reach food or water for more than 24 hours, mice are euthanized. (b) The blood samples are collected for blood cell counts. In addition, serum and hepatic alanine aminotransferase (ALT), aspartate aminotransferase (AST) and alkaline phosphatase (ALP) levels are quantified to detect liver injury and lipopolysaccharide (LPS) level is quantified to determine inflammatory effect based on our publications [64, 65]. (c) Organs including brain, skin, bone, heart, lung, liver, colon, spleen, kidney, bladder, ovary, prostate, etc. are subjected to histological evaluation.

Bio-distribution: Using the same method describe above for RA, cyanine5.5 (a near-infrared dye) carboxylic acid is conjugated to BURA using DCC/DMAP coupling. Dye-labeled BURA is administered orally. After a pre-defined time, mice are sacrificed; organs as well as adipose and muscle tissue are excised. For the intestinal tract, extensive intraluminal flushing with saline is done to remove unbound nanoparticles. BURA uptake by organs and tissues is quantified using optical imaging with a Bioluminescence IVIS Imaging System (Caliper LifeSciences). Subsequently, tissue sections are prepared for confocal fluorescent microscopy to determine how far the cyanine-label PVA penetrates the tissues and in what cell types. This imaging method is described in our recent publications [41, 42, 66].

Figure 6:
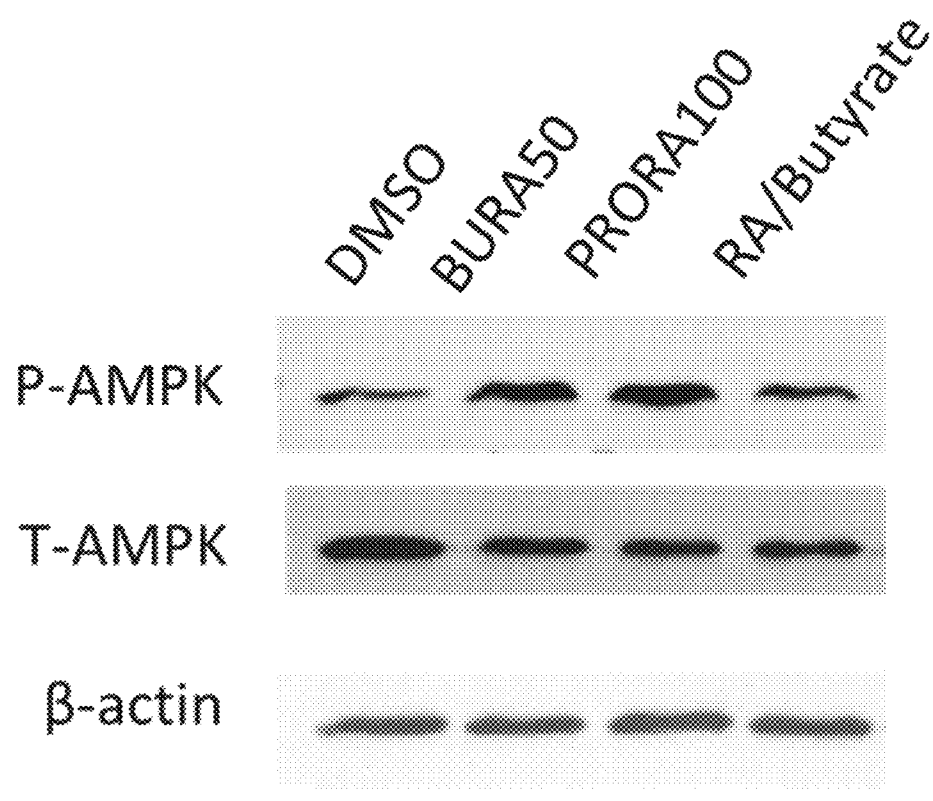
FIG. 6. BURA50 and PRORA100 activate AMPK in human liver cancer Huh7 cells, demonstrating their metabolic effects. Huh7 cells were treated by DMSO, BURA50 (100 μg/ml), PRORA100 (100 μg/ml), or a combination of retinoic acid (5 μM) plus butyrate (3 mM) for 48 h followed by western blot to detect the level of phospho-AMPK and total AMPK.

Anti-tumor animal trials: ApcΔ14/+ mice of both sexes are used. Visible gross tumors are expected when ApcΔ14/+ mice are 2.5 months old [60]. Mice are treated with and without BURA (1.34 mg/g, oral, daily) starting at 2.5 months of age for 4 weeks as we have done for BURA50 and BURA100, shown in FIG. 6. PVA will be used as a negative control. Butyrate and RA at the same molar ratio are used to compare the selected BURA. Body weight and food/water intake are recorded weekly. Tumor burden including incidence, multiplicity, and volume are determined. Whole-mount colons are stained by methylene blue (0.2%) to score the number and size of tumors under a dissecting microscope. Tumor load per mouse and per location are determined using tumor diameter to calculate the spherical volume.

Rigor, Reproducibility, Data Analysis, and Sample Size

The statistical analysis for each experiment follows a similar process for all quantitative outcome measures. Each measure is summarized descriptively by group (mean, standard deviation, histograms/box plots) and transformation applied if needed to address heteroscedasticity or non-normality. Comparisons between groups are conducted by two-way (or three-way) ANOVA tests. For statistical rigor, we protect the experiment-wise Type I error rate in our ANOVA tests by carrying out an overall F test first, and testing factor effects only if the F test is significant at 0.05. If so, we use structured contrasts to test for main effects and, where appropriate, for effect modification. Comparisons across more than two groups within a factor use Tukey's HSD correction for multiple comparisons. In addition, we use linear regression to explore the associations with covariates.

For mouse anti-cancer experiment, the primary endpoint is the tumor burden. To reduce variability, litter effects are controlled by taking mice from multiple dams to randomly assign the same number of male and female pups per litter to a group. Additionally, mice are housed 4 per cage to reduce cage effects. 12 mice are used per study group to reach appropriate power. Preliminary data support a mean reduction of at least 6.1 in tumor number due to BURA treatment, with at most SD=2.4 (FIG. 4). Twelve mice per group have at least 99% power to detect one SD difference between the groups.

Vertebrate animals: Transgenic mice of carbonic anhydrase 1 (CA1)-driven Cre (Jackson Lab) are crossed to mice having LoxP sites inserted flanking exon14 of the Apc gene (APC580S/+, NCI-Mouse Model of Human Cancers Consortium) to produce ApcΔ14/+ mice that have deletion of a single Apc gene allele. All mice are in a C57BL/6 background. CA1-Cre, Apc580S colonies are maintained. The estimated number of mice needed for each colony is 5 males and 10 females.

Mice are treated with PVA or BURA (1.34 mg/g body weight, oral gavage, daily). The number of mice used for the toxicity study is 72 mice=2 sexes×3 treatments×12 mice/group. The number of mice used for the bio-distribution study is 48 mice=2 sexes×2 treatments×12 mice/group. The number of mice used for the tumor treatment study is 72 mice=2 sexes×3 treatments×12 mice/group.

Results, Data Interpretation, and Alternative Approaches

When BURA250 (1.34 mg/g) is used, the amount of RA administered is only 0.005 mg/g based on the projected conjugation efficiency. Due to the metabolic effect of RA, one potential effect is weight loss. We also observed a blood sugar lowering effect when RA and butyrate were combined. Potentially, this can be beneficial because insulin resistance and obesity are risks for CRC [67, 68]. This possibility can be studied if BURA reduces body weight. If other toxicities are found, alternative approaches can include reducing the dose and frequency of treatment for the proposed anti-tumor animal experiment.

Via oral administration, BURA reaches the gut and liver to exert its transcriptional effect within a couple of hours (FIG. 3).

In some embodiments, BURA can be combined with other compounds such as PRORA.

BIBLIOGRAPHY AND REFERENCES CITED

[1] E. Kesse, F. Clavel-Chapelon, M. C. Boutron-Ruault, Dietary patterns and risk of colorectal tumors: a cohort of French women of the National Education System (E3N), Am J Epidemiol 164(11) (2006) 1085-93.

[2] F. A. Haggar, R. P. Boushey, Colorectal cancer epidemiology: incidence, mortality, survival, and risk factors, Clin Colon Rectal Surg 22(4) (2009) 191-7.

[3] P. Boyle, J. S. Langman, ABC of colorectal cancer: Epidemiology, BMJ 321(7264) (2000) 805-8.

[4] S. C. Larsson, A. Wolk, Meat consumption and risk of colorectal cancer: a meta-analysis of prospective studies, Int J Cancer 119(11) (2006) 2657-64.

[5] K. Wu, F. B. Hu, C. Fuchs, E. B. Rimm, W. C. Willett, E. Giovannucci, Dietary patterns and risk of colon cancer and adenoma in a cohort of men (United States), Cancer Causes Control 15(9) (2004) 853-62.

[6] J. Xiong, Q. Du, Z. Liang, Tumor-suppressive microRNA-22 inhibits the transcription of E-box-containing c-Myc target genes by silencing c-Myc binding protein, Oncogene 29(35) (2010) 4980-8.

[7] B. Ling, G. X. Wang, G. Long, J. H. Qiu, Z. L. Hu, Tumor suppressor miR-22 suppresses lung cancer cell progression through post-transcriptional regulation of ErbB3, J Cancer Res Clin Oncol 138(8) (2012) 1355-61.

[8] M. Yamakuchi, S. Yagi, T. Ito, C. J. Lowenstein, MicroRNA-22 regulates hypoxia signaling in colon cancer cells, PLoS One 6(5) (2011) e20291.

[9] J. Li, Y. Zhang, J. Zhao, F. Kong, Y. Chen, Overexpression of miR-22 reverses paclitaxel-induced chemoresistance through activation of PTEN signaling in p53-mutated colon cancer cells, Mol Cell Biochem 357(1-2) (2011) 31-8.

[10] N. Tsuchiya, M. Izumiya, H. Ogata-Kawata, K. Okamoto, Y. Fujiwara, M. Nakai, A. Okabe, A. J. Schetter, E. D. Bowman, Y. Midorikawa, Y. Sugiyama, H. Aburatani, C. C. Harris, H. Nakagama, Tumor suppressor miR-22 determines p53-dependent cellular fate through post-transcriptional regulation of p21, Cancer Res 71(13) (2011) 4628-39.

[11] Y. Hu, S. W. French, T. Chau, H. X. Liu, L. Sheng, F. Wei, J. Stondell, J. C. Garcia, Y. Du, C. L. Bowlus, Y. Y. Wan, RARbeta acts as both an upstream regulator and downstream effector of miR-22, which epigenetically regulates NUR77 to induce apoptosis of colon cancer cells, FASEB J 33(2) (2019) 2314-2326.

[12] F. Yang, Y. Hu, H. X. Liu, Y. J. Wan, MiR-22-silenced cyclin A expression in colon and liver cancer cells is regulated by bile acid receptor, J Biol Chem 290(10) (2015) 6507-15.

[13] H. Yang, Q. Zhan, Y. J. Wan, Enrichment of Nur77 mediated by retinoic acid receptor beta leads to apoptosis of human hepatocellular carcinoma cells induced by fenretinide and histone deacetylase inhibitors, Hepatology 53(3) (2011) 865-74.

[14] M. Iwata, A. Yokota, Retinoic acid production by intestinal dendritic cells, Vitam Horm 86 (2011) 127-52.

[15] V. Julia, L. Macia, D. Dombrowicz, The impact of diet on asthma and allergic diseases, Nat Rev Immunol 15(5) (2015) 308-22.

[16] A. Koh, F. De Vadder, P. Kovatcheva-Datchary, F. Backhed, From Dietary Fiber to Host Physiology: Short-Chain Fatty Acids as Key Bacterial Metabolites, Cell 165(6) (2016) 1332-1345.

[17] P. A. Gill, M. C. van Zelm, J. G. Muir, P. R. Gibson, Review article: short chain fatty acids as potential therapeutic agents in human gastrointestinal and inflammatory disorders, Aliment Pharmacol Ther 48(1) (2018) 15-34.

[18] G. den Besten, K. van Eunen, A. K. Groen, K. Venema, D. J. Reijngoud, B. M. Bakker, The role of short-chain fatty acids in the interplay between diet, gut microbiota, and host energy metabolism, J Lipid Res 54(9) (2013) 2325-40.

[19] Y. Hu, H. X. Liu, Y. He, Y. Fang, J. Fang, Y. J. Wan, Transcriptome profiling and genome-wide DNA binding define the differential role of fenretinide and all-trans RA in regulating the death and survival of human hepatocellular carcinoma Huh7 cells, Biochem Pharmacol 85(7) (2013) 1007-17.

[20] L. J. Gudas, J. A. Wagner, Retinoids regulate stem cell differentiation, J Cell Physiol 226(2) (2011) 322-30.

[21] P. Ordonez-Moran, C. Dafflon, M. Imajo, E. Nishida, J. Huelsken, HOXA5 Counteracts Stem Cell Traits by Inhibiting Wnt Signaling in Colorectal Cancer, Cancer Cell 28(6) (2015) 815-829.

[22] K. A. Sharow, B. Temkin, M. A. Asson-Batres, Retinoic acid stability in stem cell cultures, Int J Dev Biol 56(4) (2012) 273-8.

[23] W. H. Tolleson, S. H. Cherng, Q. Xia, M. Boudreau, J. J. Yin, W. G. Wamer, P. C. Howard, H. Yu, P. P. Fu, Photodecomposition and phototoxicity of natural retinoids, Int J Environ Res Public Health 2(1) (2005) 147-55.

[24] K. Hatake, M. Uwai, T. Ohtsuki, H. Tomizuka, T. Izumi, M. Yoshida, Y. Miura, Rare but important adverse effects of all-trans retinoic acid in acute promyelocytic leukemia and their management, Int J Hematol 66(1) (1997) 13-9.

[25] J. D. Bremner, K. D. Shearer, P. J. McCaffery, Retinoic acid and affective disorders: the evidence for an association, J Clin Psychiatry 73(1) (2012) 37-50.

[26] E. Patatanian, D. F. Thompson, Retinoic acid syndrome: a review, J Clin Pharm Ther 33(4) (2008) 331-8.

[27] S. W. Kim, J. M. Hooker, N. Otto, K. Win, L. Muench, C. Shea, P. Carter, P. King, A. E. Reid, N. D. Volkow, J. S. Fowler, Whole-body pharmacokinetics of HDAC inhibitor drugs, butyric acid, valproic acid and 4-phenylbutyric acid measured with carbon-11 labeled analogs by PET, Nucl Med Biol 40(7) (2013) 912-8.

[28] A. A. Miller, E. Kurschel, R. Osieka, C. G. Schmidt, Clinical pharmacology of sodium butyrate in patients with acute leukemia, Eur J Cancer Clin Oncol 23(9) (1987) 1283-7.

[29] A. Belcheva, T. Irrazabal, S. J. Robertson, C. Streutker, H. Maughan, S. Rubino, E. H. Moriyama, J. K. Copeland, A. Surendra, S. Kumar, B. Green, K. Geddes, R. C. Pezo, W. W. Navarre, M. Milosevic, B. C. Wilson, S. E. Girardin, T. M. S. Wolever, W. Edelmann, D. S. Guttman, D. J. Philpott, A. Martin, Gut microbial metabolism drives transformation of MSH2-deficient colon epithelial cells, Cell 158(2) (2014) 288-299.

[30] J. C. Arthur, E. Perez-Chanona, M. Muhlbauer, S. Tomkovich, J. M. Uronis, T. J. Fan, B. J. Campbell, T. Abujamel, B. Dogan, A. B. Rogers, J. M. Rhodes, A. Stintzi, K. W. Simpson, J. J. Hansen, T. O. Keku, A. A. Fodor, C. Jobin, Intestinal inflammation targets cancer-inducing activity of the microbiota, Science 338(6103) (2012) 120-3.

[31] G. Y. Chen, M. H. Shaw, G. Redondo, G. Nunez, The innate immune receptor Nod1 protects the intestine from inflammation-induced tumorigenesis, Cancer Res 68(24) (2008) 10060-7.

[32] S. I. Grivennikov, K. Wang, D. Mucida, C. A. Stewart, B. Schnabl, D. Jauch, K. Taniguchi, G. Y. Yu, C. H. Osterreicher, K. E. Hung, C. Datz, Y. Feng, E. R. Fearon, M. Oukka, L. Tessarollo, V. Coppola, F. Yarovinsky, H. Cheroutre, L. Eckmann, G. Trinchieri, M. Karin, Adenoma-linked barrier defects and microbial products drive IL-23/IL-17-mediated tumour growth, Nature 491 (7423) (2012) 254-8.

[33] S. Huber, N. Gagliani, L. A. Zenewicz, F. J. Huber, L. Bosurgi, B. Hu, M. Hedl, W. Zhang, W. O'Connor, Jr., A. J. Murphy, D. M. Valenzuela, G. D. Yancopoulos, C. J. Booth, J. H. Cho, W. Ouyang, C. Abraham, R. A. Flavell, IL-22BP is regulated by the inflammasome and modulates tumorigenesis in the intestine, Nature 491(7423) (2012) 259-63.

[34] E. S. Boroff, S. R. Gurudu, J. G. Hentz, J. A. Leighton, F. C. Ramirez, Polyp and adenoma detection rates in the proximal and distal colon, Am J Gastroenterol 108(6) (2013) 993-9.

[35] J. H. Cummings, E. W. Pomare, W. J. Branch, C. P. Naylor, G. T. Macfarlane, Short chain fatty acids in human large intestine, portal, hepatic and venous blood, Gut 28(10) (1987) 1221-7.

[36] E. E. Canfora, J. W. Jocken, E. E. Blaak, Short-chain fatty acids in control of body weight and insulin sensitivity, Nat Rev Endocrinol 11(10) (2015) 577-91.

[37] N. Singh, A. Gurav, S. Sivaprakasam, E. Brady, R. Padia, H. Shi, M. Thangaraju, P. D. Prasad, S. Manicassamy, D. H. Munn, J. R. Lee, S. Offermanns, V. Ganapathy, Activation of Gpr109a, receptor for niacin and the commensal metabolite butyrate, suppresses colonic inflammation and carcinogenesis, Immunity 40(1) (2014) 128-39.

[38] M. Iwata, A. Hirakiyama, Y. Eshima, H. Kagechika, C. Kato, S. Y. Song, Retinoic acid imprints gut-homing specificity on T cells, Immunity 21(4) (2004) 527-38.

[39] D. Ahmed, P. W. Eide, I. A. Eilertsen, S. A. Danielsen, M. Eknaes, M. Hektoen, G. E. Lind, R. A. Lothe, Epigenetic and genetic features of 24 colon cancer cell lines, Oncogenesis 2 (2013) e71.

[40] L. Peng, R. Liu, M. *Andrei*, W. Xiao, K. S. Lam, In vivo optical imaging of human lymphoma xenograft using a library-derived peptidomimetic against alpha4beta1 integrin, Mol Cancer Ther 7(2) (2008) 432-7.

[41] Y. Luo, H. Wu, C. Feng, K. Xiao, X. Yang, Q. Liu, T. Y. Lin, H. Zhang, J. H. Walton, Y. Ajena, Y. Hu, K. S. Lam, Y. Li, "One-Pot" Fabrication of Highly Versatile and Biocompatible Poly(vinyl alcohol)-porphyrin-based Nanotheranostics, Theranostics 7(16) (2017) 3901-3914.

[42] L. Zhang, D. Jing, L. Wang, Y. Sun, J. J. Li, B. Hill, F. Yang, Y. Li, K. S. Lam, Unique Photochemo-Immuno-Nanoplatform against Orthotopic Xenograft Oral Cancer and Metastatic Syngeneic Breast Cancer, Nano Lett 18(11) (2018) 7092-7103.

[43] M. Ashjari, S. Khoee, A. R. Mandavian, R. Rahmatolahzadeh, Self-assembled nanomicelles using PLGA-PEG amphiphilic block copolymer for insulin delivery: a physicochemical investigation and determination of CMC values, J Mater Sci Mater Med 23(4) (2012) 943-53.

[44] E. Mendes, B. G. Acetturi, A. M. Thomas, F. D. S. Martins, A. R. Crisma, G. Murata, T. T. Braga, N. O. S. Camara, A. Franco, J. C. Setubal, W. R. Ribeiro, C. J. Valduga, R. Curi, E. Dias-Neto, W. Tavares-de-Lima, C. M. Ferreira, Prophylactic Supplementation of *Bifidobacterium longum* 5(1A) Protects Mice from Ovariectomy-Induced Exacerbated Allergic Airway Inflammation and Airway Hyperresponsiveness, Front Microbiol 8 (2017) 1732.

[45] M. A. Kane, J. L. Napoli, Quantification of endogenous retinoids, Methods Mol Biol 652 (2010) 1-54.

[46] J. P. Katz, N. Perreault, B. G. Goldstein, C. S. Lee, P. A. Labosky, V. W. Yang, K. H. Kaestner, The zinc-finger transcription factor Klf4 is required for terminal differentiation of goblet cells in the colon, Development 129 (11) (2002) 2619-28.

[47] M. Houle, P. Prinos, A. Iulianella, N. Bouchard, D. Lohnes, Retinoic acid regulation of Cdx1: an indirect mechanism for retinoids and vertebral specification, Mol Cell Biol 20(17) (2000) 6579-86.

[48] J. H. Shi, B. Zheng, S. Chen, G. Y. Ma, J. K. Wen, Retinoic acid receptor alpha mediates all-trans-retinoic acid-induced Klf4 gene expression by regulating Klf4 promoter activity in vascular smooth muscle cells, J Biol Chem 287(14) (2012) 10799-811.

[49] Y. Wang, C. Tian, J. C. Zheng, FoxO3a contributes to the reprogramming process and the differentiation of induced pluripotent stem cells, Stem Cells Dev 22(22) (2013) 2954-63.

[50] Z. Kozovska, V. Gabrisova, L. Kucerova, Colon cancer: cancer stem cells markers, drug resistance and treatment, Biomed Pharmacother 68(8) (2014) 911-6.

[51] Y. Hu, T. Chau, H. X. Liu, D. Liao, R. Keane, Y. Nie, H. Yang, Y. J. Wan, Bile acids regulate nuclear receptor (Nur77) expression and intracellular location to control proliferation and apoptosis, Mol Cancer Res 13(2) (2015) 281-92.

[52] Y. Li, T. Y. Lin, Y. Luo, Q. Liu, W. Xiao, W. Guo, D. Lac, H. Zhang, C. Feng, S. Wachsmann-Hogiu, J. H. Walton, S. R. Cherry, D. J. Rowland, D. Kukis, C. Pan, K. S. Lam, A smart and versatile theranostic nanomedicine platform based on nanoporphyrin, Nat Commun 5 (2014) 4712.

[53] K. Xiao, Q. Liu, N. Al Awwad, H. Zhang, L. Lai, Y. Luo, J. S. Lee, Y. Li, K. S. Lam, Reversibly disulfide cross-linked micelles improve the pharmacokinetics and facilitate the targeted, on-demand delivery of doxorubicin in the treatment of B-cell lymphoma, Nanoscale 10(17) (2018) 8207-8216.

[54] Q. Long, T. Y. Lin, Y. Huang, X. Li, A. H. Ma, H. Zhang, R. Carney, S. Airhart, K. S. Lam, R. W. deVere White, C. X. Pan, Y. Li, Image-guided photo-therapeutic nanoporphyrin synergized HSP90 inhibitor in patient-derived xenograft bladder cancer model, Nanomedicine 14(3) (2018) 789-799.

[55] W. Xiao, N. Suby, K. Xiao, T. Y. Lin, N. Al Awwad, K. S. Lam, Y. Li, Extremely long tumor retention, multi-responsive boronate crosslinked micelles with superior therapeutic efficacy for ovarian cancer, J Control Release 264 (2017) 169-179.

[56] E. J. Hixson, E. P. Denine, Comparative subacute toxicity of all-trans- and 13-cis-retinoic acid in Swiss mice, Toxicol Appl Pharmacol 44(1) (1978) 29-40.

[57] L. Peng, R. Liu, J. Marik, X. Wang, Y. Takada, K. S. Lam, Combinatorial chemistry identifies high-affinity peptidomimetics against alpha4beta1 integrin for in vivo tumor imaging, Nat Chem Biol 2(7) (2006) 381-9.

[58] W. Xiao, T. Li, F. C. Bononi, D. Lac, I. A. Kekessie, Y. Liu, E. Sanchez, A. Mazloom, A. H. Ma, J. Lin, J. Tran, K. Yang, K. S. Lam, R. Liu, Discovery and characterization of a high-affinity and high-specificity peptide ligand LXY30 for in vivo targeting of alpha3 integrin-expressing human tumors, EJNMMI Res 6(1) (2016) 18.
[59] W. Xiao, J. Luo, T. Jain, J. W. Riggs, H. P. Tseng, P. T. Henderson, S. R. Cherry, D. Rowland, K. S. Lam, Biodistribution and pharmacokinetics of a telodendrimer micellar paclitaxel nanoformulation in a mouse xenograft model of ovarian cancer, Int J Nanomedicine 7 (2012) 1587-97.
[60] Y. Xue, R. Johnson, M. Desmet, P. W. Snyder, J. C. Fleet, Generation of a transgenic mouse for colorectal cancer research with intestinal cre expression limited to the large intestine, Mol Cancer Res 8(8) (2010) 1095-104.
[61] A. R. Moser, E. M. Mattes, W. F. Dove, M. J. Lindstrom, J. D. Haag, M. N. Gould, ApcMin, a mutation in the murine Apc gene, predisposes to mammary carcinomas and focal alveolar hyperplasias, Proc Natl Acad Sci USA 90(19) (1993) 8977-81.
[62] A. R. Moser, C. Luongo, K. A. Gould, M. K. McNeley, A. R. Shoemaker, W. F. Dove, ApcMin: a mouse model for intestinal and mammary tumorigenesis, Eur J Cancer 31A(7-8) (1995) 1061-4.
[63] M. H. Kucherlapati, K. Lee, A. A. Nguyen, A. B. Clark, H. Hou, Jr., A. Rosulek, H. Li, K. Yang, K. Fan, M. Lipkin, R. T. Bronson, L. Jelicks, T. A. Kunkel, R. Kucherlapati, W. Edelmann, An Msh2 conditional knockout mouse for studying intestinal cancer and testing anticancer agents, Gastroenterology 138(3) (2010) 993-1002 e1.
[64] L. Sheng, P. K. Jena, Y. Hu, H. X. Liu, N. Nagar, K. M. Kalanetra, S. W. French, S. W. French, D. A. Mills, Y. Y. Wan, Hepatic inflammation caused by dysregulated bile acid synthesis is reversible by butyrate supplementation, J Pathol 243(4) (2017) 431-441.
[65] P. K. Jena, L. Sheng, H. X. Liu, K. M. Kalanetra, A. Mirsoian, W. J. Murphy, S. W. French, V. V. Krishnan, D. A. Mills, Y. Y. Wan, Western Diet-Induced Dysbiosis in Farnesoid X Receptor Knockout Mice Causes Persistent Hepatic Inflammation after Antibiotic Treatment, Am J Pathol 187(8) (2017) 1800-1813.
[66] L. Zhang, T. Yin, B. Li, R. Zheng, C. Qiu, K. S. Lam, Q. Zhang, X. Shuai, Size-Modulable Nanoprobe for High-Performance Ultrasound Imaging and Drug Delivery against Cancer, ACS Nano 12(4) (2018) 3449-3460.
[67] A. P. Ortiz, C. L. Thompson, A. Chak, N. A. Berger, L. Li, Insulin resistance, central obesity, and risk of colorectal adenomas, Cancer 118(7) (2012) 1774-81.
[68] P. J. Limburg, R. Z. Stolzenberg-Solomon, R. A. Vierkant, K. Roberts, T. A. Sellers, P. R. Taylor, J. Virtamo, J. R. Cerhan, D. Albanes, Insulin, glucose, insulin resistance, and incident colorectal cancer in male smokers, Clin Gastroenterol Hepatol 4(12) (2006) 1514-21.
[69] C. Bernstein, H. Holubec, A. K. Bhattacharyya, H. Nguyen, C. M. Payne, B. Zaitlin, H. Bernstein, Carcinogenicity of deoxycholate, a secondary bile acid, Arch Toxicol 85(8) (2011) 863-71.

Example 2. Synthesis of BURA100 and BURA50

(A) Polyvinyl alcohol (PVA, 6.0 g, MW: 27,000 Daltons, containing 136.2 mmol of OH groups) was dissolved in anhydrous dimethyl sulfoxide (DMSO, 150 ml) at 650° C. At room temperature, 4-dimethylaminopyridine (DMAP, 0.333 g, 2.725 mmol) used for esterification catalyst was added to the DMSO solution. Once it was dissolved, butyryl chloride (5.66 ml, 54.5 mmol) was added dropwise under argon gas flow. The resulting solution was stirred at room temperature for 2-5 hours until HCl gas could not be detected.

(B) All trans-retinoic acid (RA, 164 mg, 0.546 mmol) was dissolved in a mixture solvent of anhydrous of N,N-dimethylformamide (DMF, 1.2 ml) and anhydrous dichloromethane (4.0 ml) at 40° C., then N,N'-dicyclohexylcarbodiimide (DCC, 117 mg, 0.567 mmol) was added as a coupling reagent. The solution was stirred for 15 minutes.

(C) (A) and (B) were mixed in presence of additional DMAP (6.7 mg, 0.0548 mmol). Under argon gas atmosphere and in the dark, the reaction mixture was stirred at room temperature for 2 days. Then, acetonitrile (1 liter) was added for precipitation. The precipitate was collected after centrifugation and decanting, followed by washing 3 times with acetonitrile. The precipitate was suspended in water and filtered using 0.2 μm filter. The water solution was dialyzed in large amount of water (molecular cut-off size 6000-8000) for 2 days. Water was changed 5 times during dialysis. Then, solution was filtered and lyophilized to generate a light brown solid.

BURA50 was synthesized using the same procedure as BURA100, but half the amount of butyryl chloride (2.83 ml) was used.

Example 3. Synthesis of PRORA100

(A) Polyvinyl alcohol (PVA, 8.0 g, MW: 27,000 Daltons, containing 181.6 mmol of OH groups) was dissolved in anhydrous dimethyl sulfoxide (DMSO, 300 ml) at 650° C. At room temperature, DMAP (0.444 g, 3.634 mmol) used for esterification catalyst was added. Once it was dissolved, propionyl chloride (6.35 ml, 72.68 mmol) was added dropwise under argon gas flow. The resulting solution was stirred at room temperature for 2-5 hours until HCl gas could not be detected.

(B) All trans-retinoic acid (RA, 219 mg, 0.729 mmol) was dissolved in a mixture solvent of anhydrous of N,N-dimethylformamide (DMF, 1.6 ml) and anhydrous dichloromethane (5.0 ml) at 40° C., then N,N'-dicyclohexylcarbodiimide (DCC, 156 mg, 0.756 mmol) were added as a coupling reagent. The solution was stirred for 15 minutes.

(C) (A) and (B) were mixed in the presence of additional DMAP (9.0 mg, 0.0737 mmol). Under argon gas atmosphere and in the dark, the reaction mixture was stirred at room temperature for 2 days. Then, acetonitrile (1.2 liter) was added for precipitation. The precipitate was collected after centrifugation and decanting, followed by washing 3 times with acetonitrile. The precipitate was suspended in water and filtered using 0.2 μm filter. The water solution was dialyzed in large amount of water (molecular cut-off size 6000-8000) for 2 days. Water was changed 5 times during dialysis. Then, the solution was filtered and lyophilized to generate a light brown solid.

Example 4. Treatment of Colon Tumors in Azoxymethane (AOM) and Dextran Sodium Sulfate (DSS) Mouse Models C57BL/6 mice were treated with azoxymethane (AOM) (10 mg/kg body weight, ip), followed by 3 cycles of 2% dextran sodium sulfate (DSS) administration in drinking water. Each cycle lasted 7 days. Between the DSS cycles, mice were provided with 2 weeks of normal drinking water. The treatment of BURA50 or BURA100 were initiated 1 week after the last DSS cycle. BURA50 (n=12) or BURA100 (n=3) at 1.34 mg/g body weight (daily, oral) were used for 4 weeks. Colon sections were stained with specific antibodies by immunohistochemistry.

The results, shown in FIG. 4, indicate that both BURA50 and BURA100 produced a decrease in the number of tumors relative to controls.

Example 5. BURA100 and miR-22 Inhibitors in Diet-Induced Obese Mice

Figure 7A:
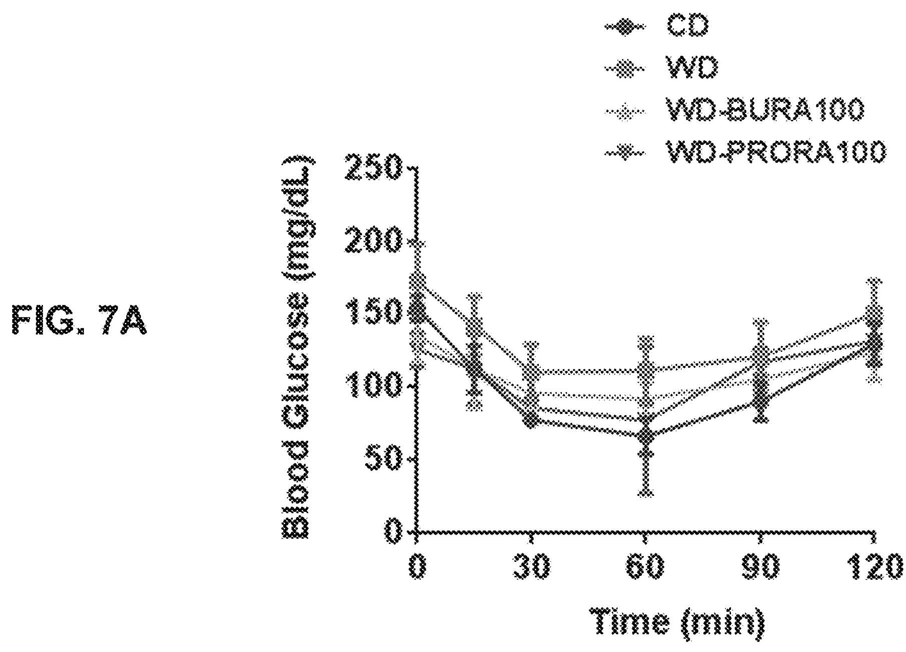
FIGS. 7A-7B. BURA100 and PRORA100 improve insulin sensitivity in diet-induced obese mice. PRORA100 reduces fasting blood glucose in diet-induced obese mice. C57BL/6 male mice were on a Western diet (WD) since weaning. When mice were 4-months old, they received BURA100 or PRORA100 (1.34 mg/g body weight, five doses per week by oral gavage) for 3 weeks followed by insulin tolerance test (ITT) (FIG. 7A) and measuring fasting blood glucose level (FIG. 7B). Age- and sex-matched control diet (CD)-fed mice without any treatment were used as baseline controls. *$p<0.05$, **$p<0.01$. n=4/group.
Figure 7B:
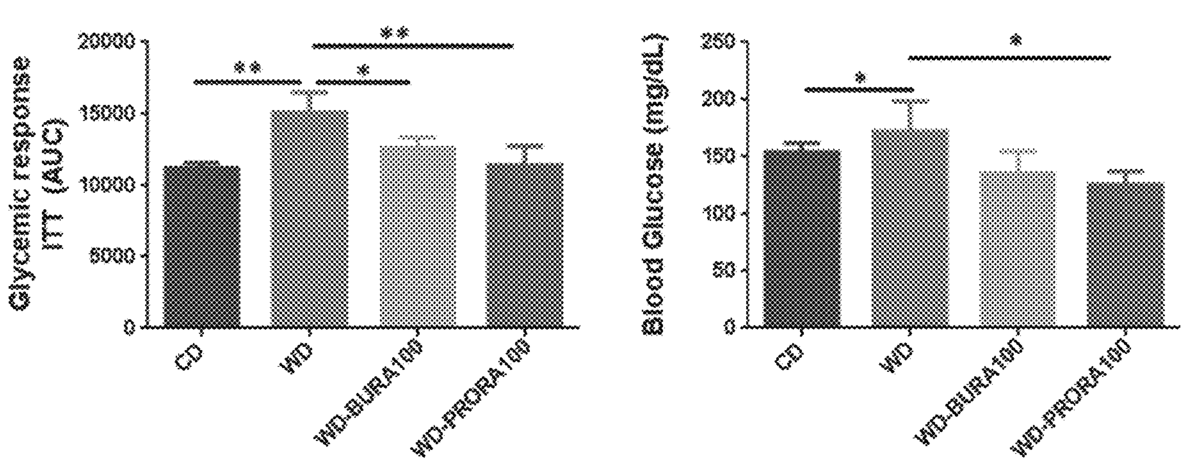
Figure 8A:
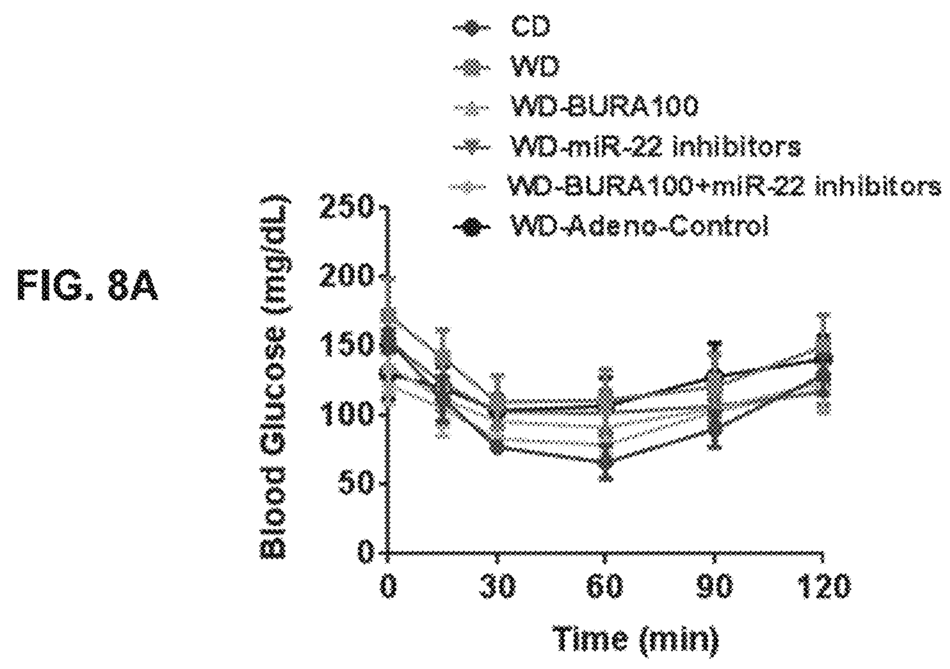
FIGS. 8A-8B. BURA100 and miR-22 inhibitors improve insulin sensitivity and reduce fasting blood glucose level in diet-induced obese mice. C57BL/6 male mice were on a Western diet (WD) since weaning. When mice were 4-months old, they received BURA100 (1.34 mg/g body weight, five doses per week by oral gavage), adenovirus serving as negative control, miR-22 inhibitors (1×109 PFU, tail vein injection, once a week), or a combination of BURA100 plus miR-22 inhibitors for 3 weeks followed by insulin tolerance test (ITT) (FIG. 8A) and measuring fasting blood glucose level (FIG. 8B). Age- and sex-matched control diet (CD)-fed mice without any treatment were used as baseline controls. *$p<0.05$, **$p<0.01$. N=4/group.
Figure 8B:
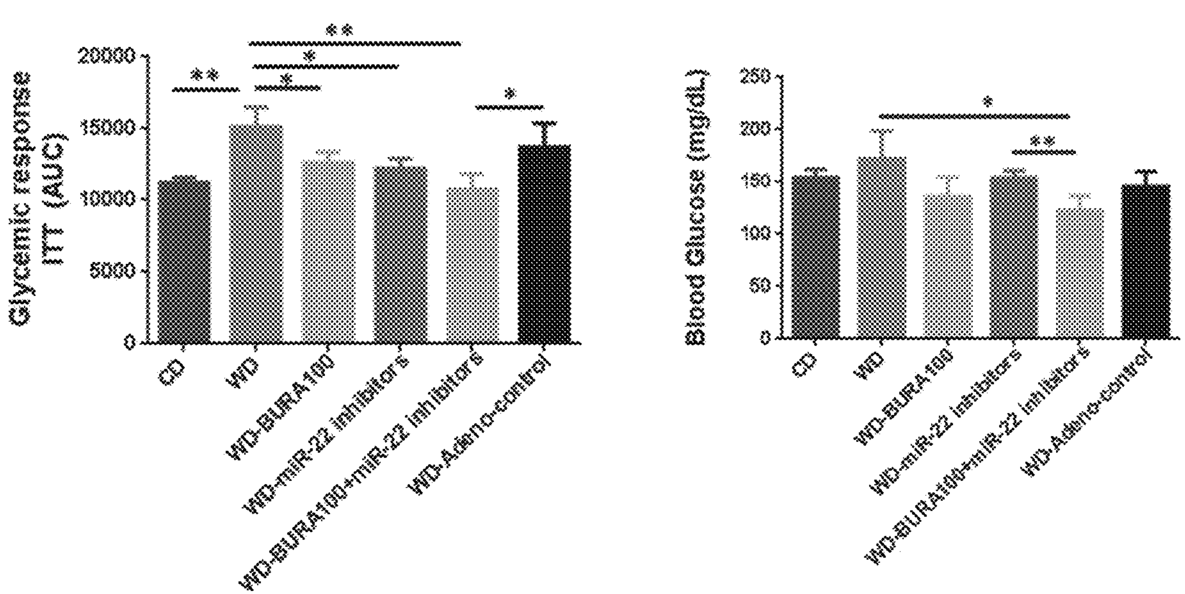

C57BL/6 male mice were put on a Western diet (WD) since weaning. When mice were 4-months old, they received BURA100 (1.34 mg/g body weight, five doses per week by oral gavage), with adenovirus serving as negative control, miR-22 inhibitors ($1\times10^9$ PFU, tail vein injection, once a week), or a combination of BURA100 plus miR-22 inhibitors for 3 weeks followed by insulin tolerance test (ITT). The results, shown in FIGS. 7A and 7B, showed that BURA100 and miR-22 inhibitors improved insulin sensitivity and reduced fasting blood glucose level in diet-induced obese mice.

Example 6. Investigating Possible Mechanisms of Action of BURA100 and PRORA100

C57BL/6 mice were treated with azoxymethane (AOM) (10 mg/kg body weight, ip), followed by 3 cycles of 2% dextran sodium sulfate (DSS) administration in drinking water. Each cycle lasted 7 days. Between the DSS cycles, mice were provided with 2 weeks of normal drinking water. The treatment with BURA50 or BURA100 was initiated 1 week after the last DSS cycle. BURA50 (n=12) or BURA100 (n=3) at 1.34 mg/g body weight (daily, oral) were used for 4 weeks. Colon sections were stained with specific antibodies by immunohistochemistry.

The results showed that the compounds increased the recruitment of T cells and B cells to the tumors. For example, BURA50 and BURA100 increased the recruitment of CD3+T lymphocytes in the colon of AOM/DSS mouse model, they increased the recruitment of $CD4^+$ helper T cells in the colon, they increased the recruitment of $CD8^+$ T cells in the colon, they increased the recruitment of B cells in the colon, and they increased PDL-1 in AOM/DSS-induced colon cancer.

Figures 13A, 13B, 13C, 13D:
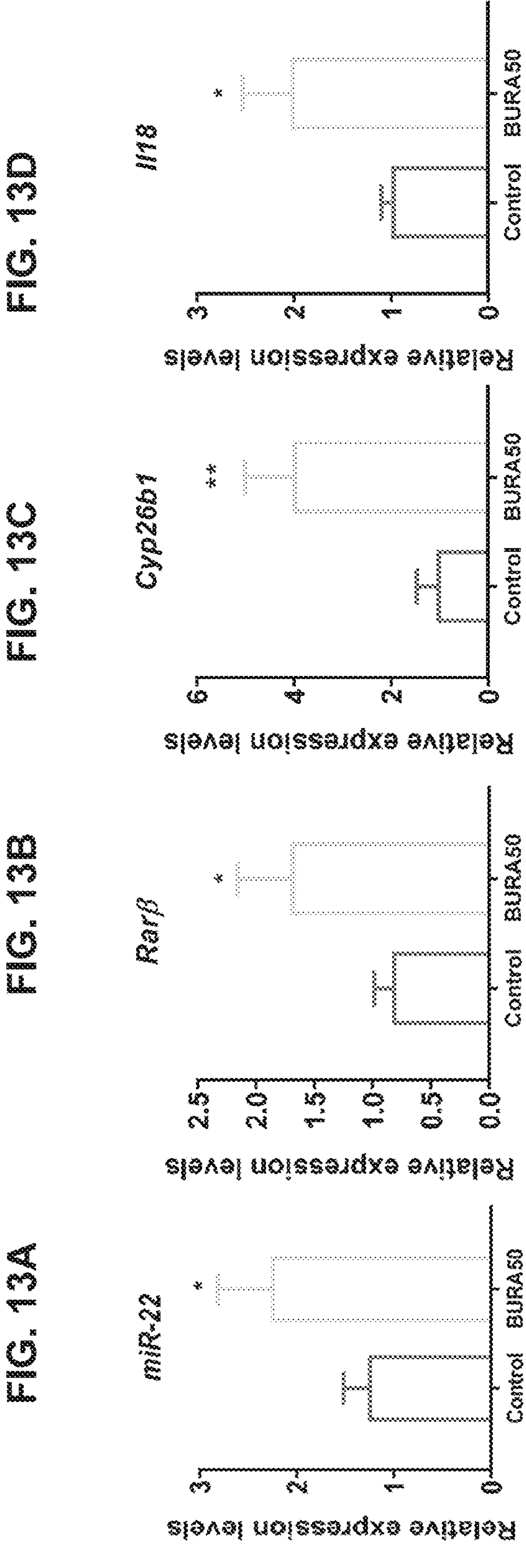
FIGS. 13A-13D. BURA50 induces miR-22 (FIG. 13A) as well as RA and butyrate signaling evidenced by the induction of Rarβ (FIG. 13B), Cyp26b1 (FIG. 13C) and 1118 (FIG. 13D) in the colons of AOM and DSS mouse models. The mRNA levels of indicated genes in AOM/DSS mouse models treated with PVA or BURA50 (n=3 per group) at 1.34 mg/g body weight by daily oral gavage for 4 weeks. BURA100 treatment started after tumors had already formed. *$p<0.05$, **$p<0.01$.

BURA100 also induced miR-22 in the colons of the mouse models (FIG. 13A). miR-22 is known to silence protein deacetylases HDAC1, HDAC4, and SIRT-1, leading to NUR77 and RARβ induction and nuclear export to induce apoptosis (FASEB J. 2019 February; 33(2):2314-2326. Epub 2018 Sep. 25. PMID: 30252536). miR-22 induction also silences Cyclin A2 (J Biol Chem. 2015 Mar. 6; 290 (10):6507-15. PMCID: PMC4358284). In addition, BURA100 induces RA and butyrate-regulated signaling (FIGS. 13B-13D), indicating that it has the free chemical effects. BURA100 and PRORA100 were also observed to have metabolic effects.

Example 7. Colon Cancer Treatment Using BURA100 or PRORA100

Figure 14A:
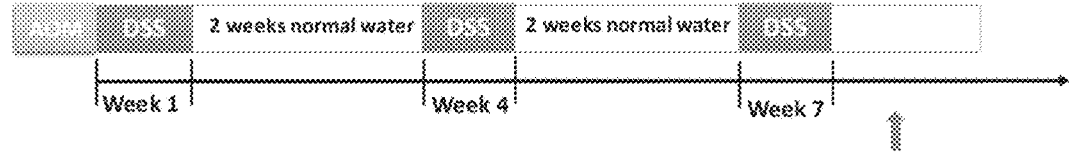
FIGS. 14A-14D.
Figure 14B:
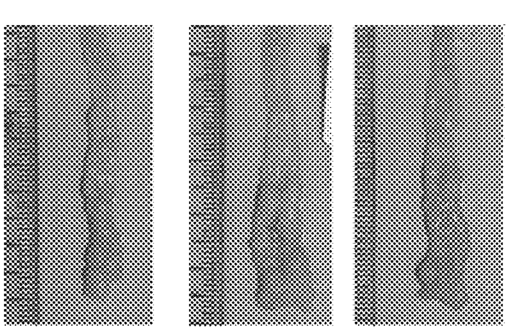
Figure 14B:
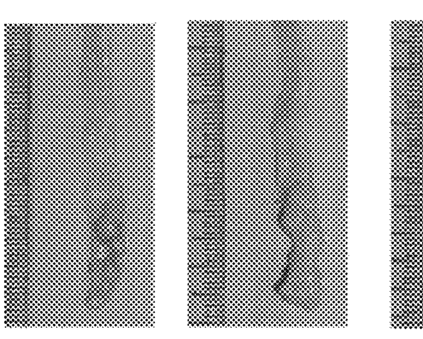
Figure 14C:
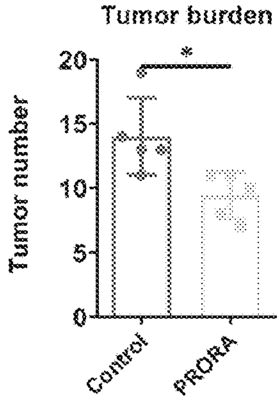
Figure 14D:
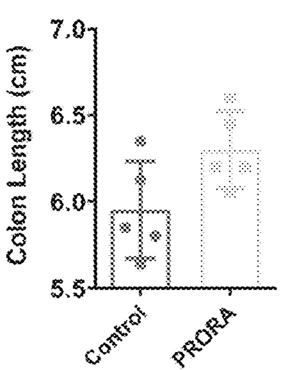

The protocol used is shown in FIG. 14A. AOM was administered at 10 mg AOM/kg body weight. DSS was administered at 2% DSS in drinking water (3 Cycles of 7-days DSS administration, 36-50 kDa). PRORA was administered at 134 mg/g body weight, by daily gavage for 4 weeks. The results showed that the compounds were effective at treating colon tumors using azoxymethane (AOM) and dextran sodium sulfate (DSS) mouse models (FIGS. 14B-14D).

Example 8. Metabolic Studies Using BURA100 or PRORA100

C57BL/6 male mice were given a control healthy control diet (5% fat, 12% sucrose, 0.01% cholesterol) or a Western diet (21% fat, 34% sucrose, 0.2% cholesterol) after weaning (3-weeks old). When Western diet-fed mice were 5-months old, they were randomly assigned into control or treatment groups. The treated groups received BURA100 or PRORA100 (134 mg/g, daily gavage, 4 weeks). All the mice were euthanized when they were 6 months old.

Figures 15A, 15B, 15C, 15D, 15E, 15F:
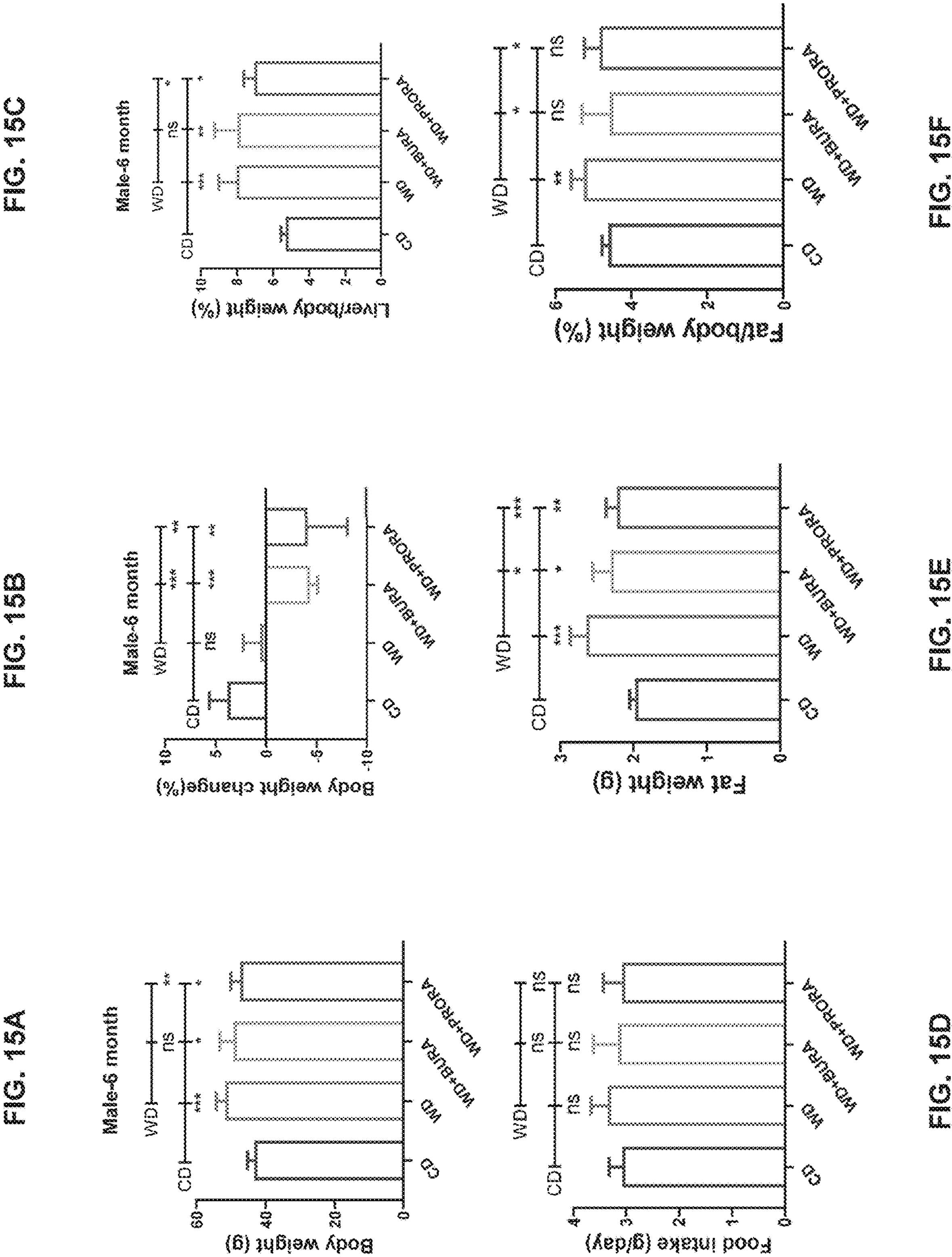
FIGS. 15A-15F. BURA100 and PRORA100 are effective in treating diet-induced body weight gain and fat weight. PRORA reduces the liver/body weight ratio, indicating its effectiveness in treating diet-induced hepatomegaly. C57BL/6 male mice were given a healthy control diet (CD)
Figure 16:
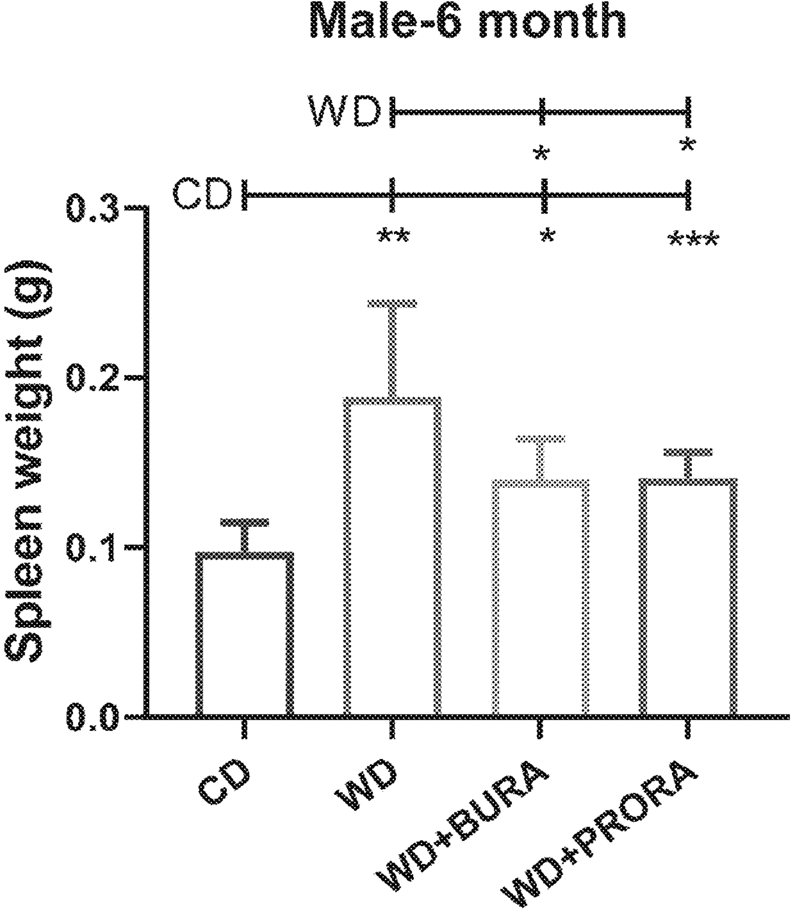
FIG. 16. Western diet intake induces splenomegaly, and BURA100 and PRORA100 reverse it. Mice were given a Control diet (CD) or Western diet (WD) and then treated with BURA100 or PRORA100 as described in FIGS. 15A-15F.
Figure 17A:
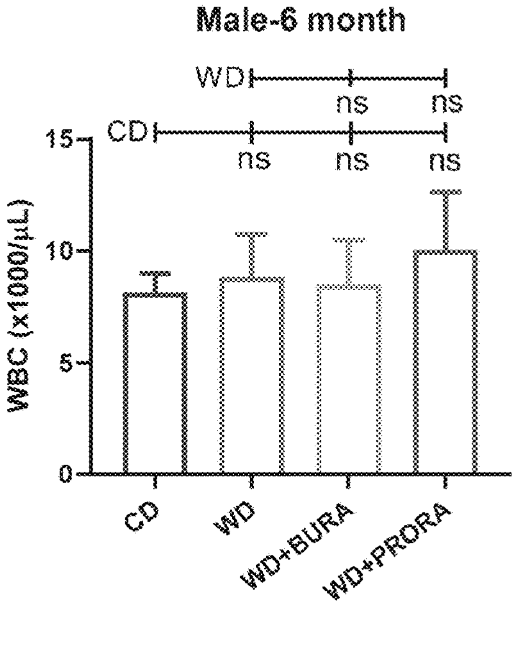
FIGS. 17A-D. The effect of Western diet intake as well as BURA100 and PRORA100 treatment on blood count. Mice were given a Control diet (CD) or Western diet (WD) and then treated with BURA100 or PRORA100 as described in FIGS. 15A-15F. Different blood cell types were quantified, including white blood cells (FIG. 17A; normal range: 4.45-13.96×1000/μL), lymphocytes (FIG. 17B; normal range: 3.24-11.15×1000/μL), monocytes (FIG. 17C; normal range: 0.15-0.94×1000/μL), and granulocytes (granular) (FIG. 17D; normal ranges: EOS: 0.01-0.42×1000/μL; BASO: 0.00-0.13×1000/μL; NEUT: 0.53-3.09×1000/μL).
Figure 17B:
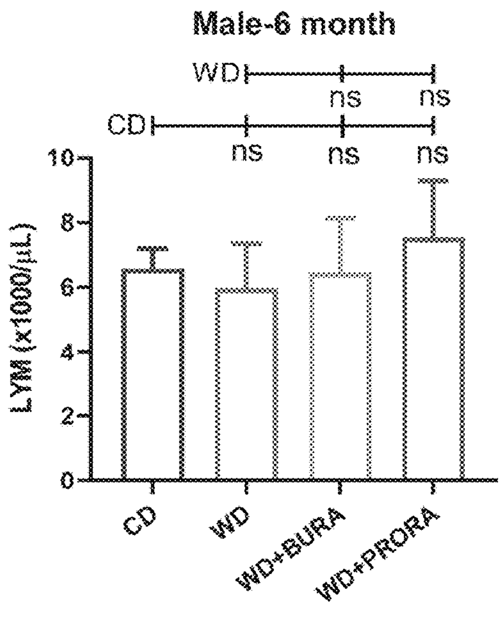
Figure 17C:
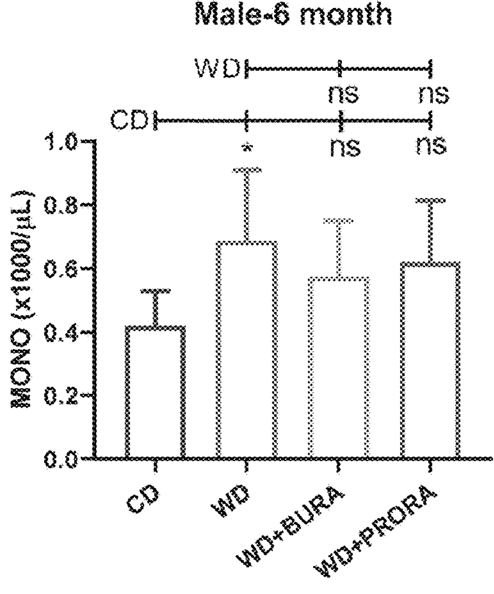
Figure 17D:
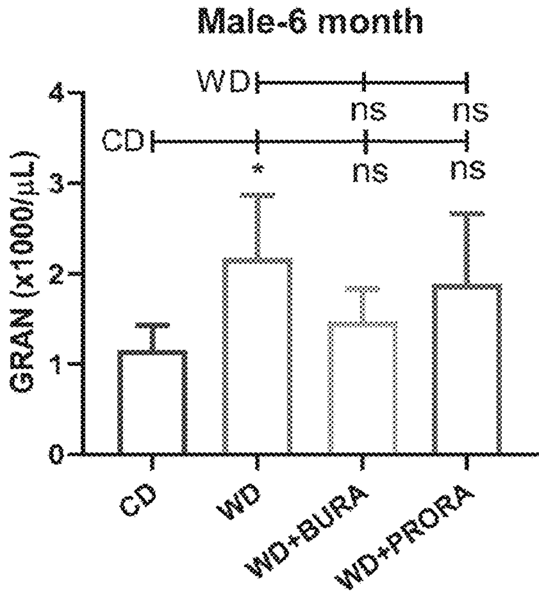

The results showed that BURA100 and PRORA100 are effective in treating diet-induced body weight gain (FIGS. 15A-15B) and fat weight (FIG. 15E). PRORA also reduces the liver/body weight ratio (FIG. 15C), indicating its effectiveness in treating diet-induced hepatomegaly. In addition, Western diet intake induces splenomegaly, and BURA100 and PRORA100 reverse it (FIG. 16).

The effects of Western diet intake as well as BURA100 and PRORA100 treatment on blood count were also studied (FIGS. 17A-17D, 18A-18D, 19A-19I). The used doses had no toxicity based on blood cell count. The data also indicated that Western diet induced inflammation and that BURA100 as well as PRORA100 have anti-inflammatory effects.

Figure 19A:
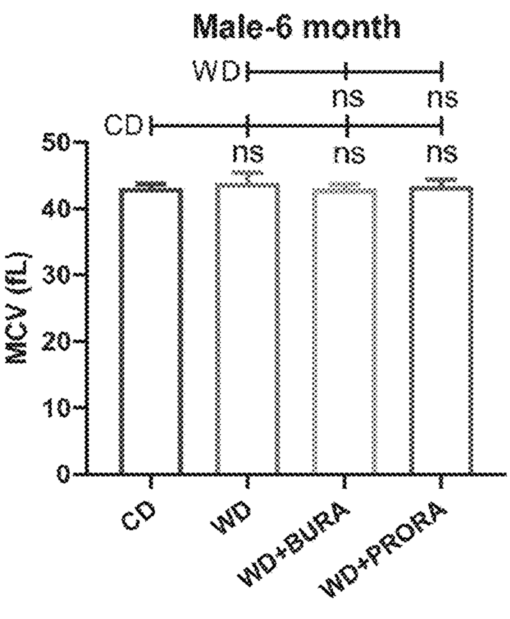
FIGS. 19A-19I. The effect of Western diet intake as well as BURA100 and PRORA100 treatment on blood count. Mice were given a Control diet (CD) or Western diet (WD) and then treated with BURA100 or PRORA100 as described in FIGS. 15A-15F. FIG. Properties of different blood cell types were determined, including the mean corpuscular volume (FIG. 19A; normal range: 42.7-56.0 fL), the red blood cell distribution (FIG. 19B), the amount of hemoglobin in red blood cells (FIG. 19C; normal range: 10.8-19.2 g/dL), the distribution of red blood cell width (FIG. 19D; normal range: 15.9-20.3%), the mean corpuscular hemoglobin concentration (FIG. 19E; normal range: 24.6-34.9 μg/dL), the mean corpuscular hemoglobin (FIG. 19F; normal range: 11.7-16.3 μg); red blood cell count in blood (FIG. 19G; normal range: 7.14-12.20 millions/μL); the number of platelets (FIG. 19H; normal range 841-2159×1000), and the mean platelet volume (FIG. 19I; normal range 4.3-6.1 fL).
Figure 19B:
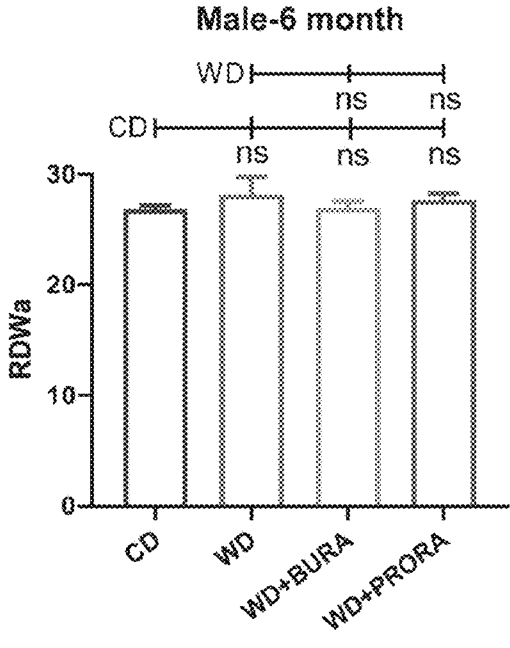
Figure 19C:
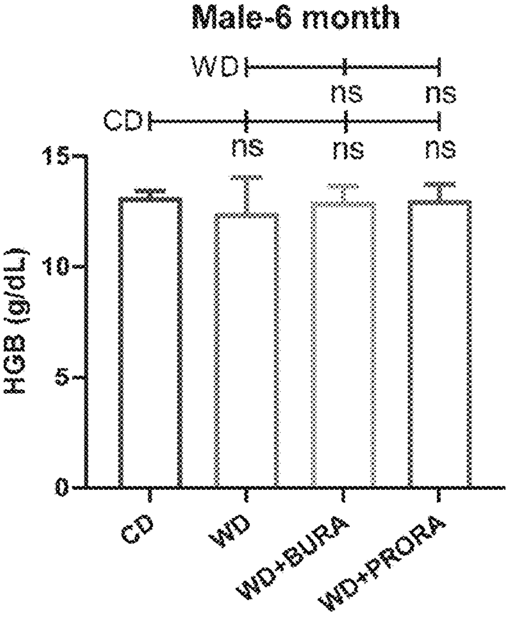
Figure 19D:
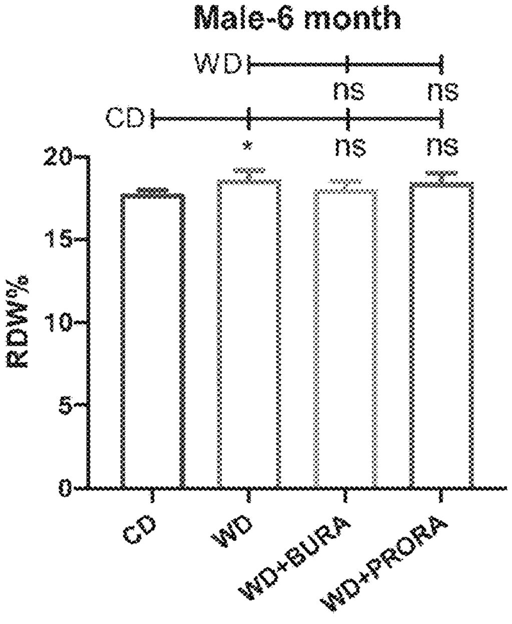
Figure 19E:
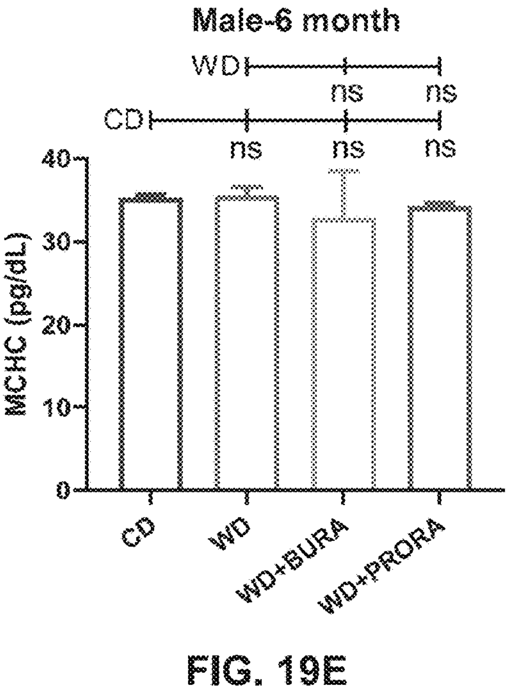
Figure 19F:
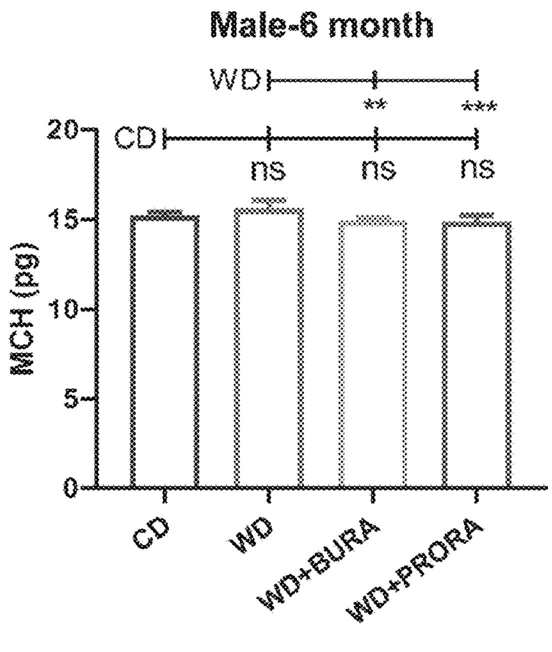
Figure 19G:
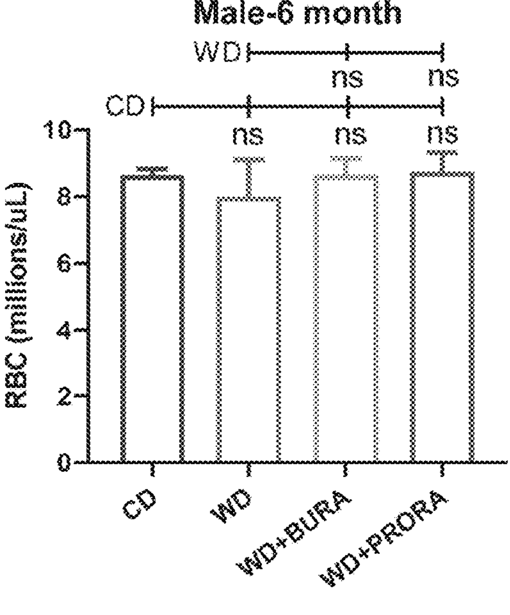
Figure 19H:
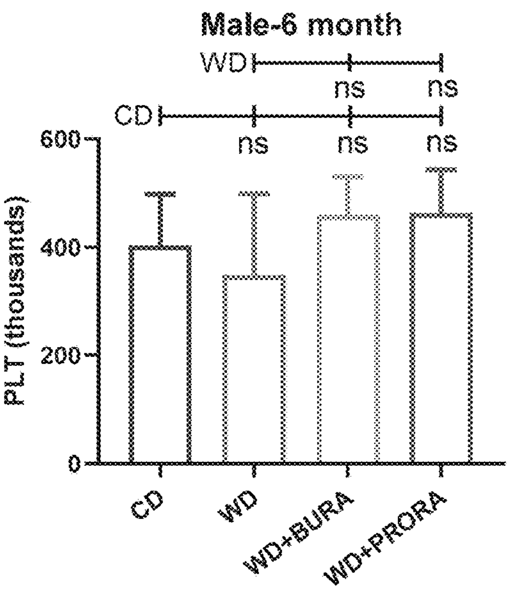
Figure 19I:
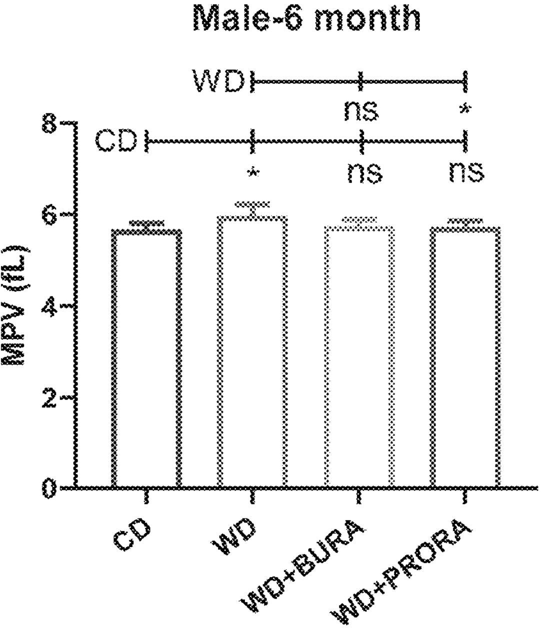

Both BURA and PRORA significantly reversed the decrease (vs. control diet) caused by Western diet on the percentage of blood made up by lymphocytes (FIG. 18A), on the increase (vs. control diet) caused by Western diet on the percentage of blood made up by monocytes (FIG. 18B), and on the increase (vs. control diet) caused by Western diet on the percentage of blood made up by granulocytes (FIG. 18C). BURA and PRORA also produced a significant decrease (vs. Western diet) in mean corpuscular hemoglobin, i.e., the calculation of the average amount of hemoglobin contained in each blood cell (FIG. 19F). PRORA also produced a significant decrease (vs. Western diet) in mean platelet volume, i.e., a test that measures the average size of platelets (FIG. 19I).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING

| SEQ ID NO: | Sequence | Description |
|---|---|---|
| 1 | 5'-AAGCUGCCAGUUGAAGAACUGU-3' | hsa-miR-22-3p sequence |
| 2 | 5'-ACAGTTCTTCAACTGGCAGCTT-3' | hsa-miR-22-3p inhibitor sequence |

What is claimed is:

1. A conjugate comprising: (a) a histone deacetylase (HDAC) inhibitor; (b) a retinoid; and (c) a polymer containing a plurality of hydroxyl groups, wherein the HDAC inhibitor and the retinoid are covalently attached to the polymer via the plurality of hydroxyl groups, and wherein the conjugate forms nanomicelles; wherein the HDAC inhibitor and the retinoid are covalently attached to the polymer at a molar ratio of from about 2,000:1 to about 5,000:1 HDAC inhibitor: retinoid.

2. The conjugate of claim 1, wherein the HDAC inhibitor is a short-chain fatty acid (SCFA).

3. The conjugate of claim 2, wherein the SCFA is selected from the group consisting of butyrate, propionate, isobutyrate, valerate, isovalerate, and a combination thereof.

4. The conjugate of claim 1, wherein the retinoid is selected from the group consisting of retinoic acid (RA), retinol, retinal, isotretinoin, alltretinoin, etretinate, acitretin, tazarotene, bexarotene, adapalene, seletinoid G, a retinyl ester, fenretinide, derivatives thereof, and a combination thereof.

5. The conjugate of claim 1, wherein the polymer is polyvinyl alcohol (PVA).

6. The conjugate of claim 1, wherein the HDAC inhibitor is butyrate, the retinoid is RA, the polymer is PVA.

7. The conjugate of claim 1, wherein the HDAC inhibitor is propionate, the retinoid is RA, the polymer is PVA.

8. The conjugate of claim 1, wherein the nanomicelles are about 5-50 nm in diameter.

9. A method for treating or preventing cancer or a metabolic disease in a subject, the method comprising administering to the subject a therapeutically effective amount of the conjugate of claim 1.

10. The method of claim 9, wherein the cancer is colon cancer or liver cancer.

11. The method of claim 9, wherein the administration of the conjugate to the subject improves one or more symptoms of cancer in the subject.

12. The method of claim 9, wherein the administration of the conjugate increases the recruitment of B or T cells to tumors in the subject.

13. The method of claim 12, wherein the T cells comprise $CD3^+$ lymphocytes, $CD4^+$ helper cells, $CD8^+$ T cells, or combinations thereof.

14. The method of claim 9, wherein the metabolic disease is selected from the group consisting of alcoholic steatohepatitis (ASH), non-alcoholic steatohepatitis (NASH), non-alcoholic fatty liver disease (NAFLD), diabetes, obesity, dyslipidemia, and a combination thereof.

15. The method of claim 9, wherein the administration of the conjugate to the subject leads to an increase in insulin sensitivity and/or a decrease in fasting blood glucose level in the subject.

16. The method of claim 9, wherein the administration of the conjugate to the subject leads to a change in expression or activity of a gene, protein, or molecule targeted by a retinoid and/or an HDAC inhibitor selected from the group consisting of Rarβ, Cyp26b1, Gpr109a, miR-22, HOX A5, AMPK, IL18, PDL-1, and combinations thereof.

17. The method of claim 9, wherein the administration of the conjugate to the subject leads to an increase in expression and/or activity of PDL-1.

18. The method of claim 9, wherein the administration of the conjugate to the subject leads to a downregulation of a gene or protein selected from the group consisting of CYCLIN A2, HDAC1, HDAC4, SIRT1, HDAC6, HDAC8, HDAC11, a protein deacetylase, and combinations thereof.

19. The method of claim 9, wherein the administration of the conjugate to the subject leads to the export of nuclear NUR77 to the cytosol.

20. The conjugate of claim 6, wherein the butyrate and the RA at a molar ratio of from about 2500:1 to about 4000:1 butyrate: RA.

21. The conjugate of claim 20, wherein the butyrate and the RA at a molar ratio of about 3000:1 butyrate: RA.

22. The conjugate of claim 7, wherein the propionate and the RA at a molar ratio of from about 3000:1 to about 5000:1 propionate: RA.

23. The conjugate of claim 22, wherein the propionate and the RA at a molar ratio of about 4000:1 propionate: RA.

24. The conjugate of claim 1, wherein the nanomicelles are about 5-30 nm in diameter.

25. The conjugate of claim 1, wherein the nanomicelles are about 15-30 nm in diameter.

* * * * *

SEQUENCE LISTING

```
<160> NUMBER OF SEQ ID NOS: 2

<210> SEQ ID NO 1
<211> LENGTH: 22
<212> TYPE: RNA
<213> ORGANISM: Homo sapiens

<400> SEQUENCE: 1

aagcugccag uugaagaacu gu                                          22


<210> SEQ ID NO 2
<211> LENGTH: 22
<212> TYPE: DNA
<213> ORGANISM: Homo sapiens

<400> SEQUENCE: 2

acagttcttc aactggcagc tt                                          22
```